US009358381B2

(12) United States Patent
Simon et al.

(10) Patent No.: US 9,358,381 B2
(45) Date of Patent: *Jun. 7, 2016

(54) NON-INVASIVE VAGAL NERVE STIMULATION TO TREAT DISORDERS

(71) Applicant: ElectroCore, LLC, Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: Electrocore, LLC, Basking Ridge, NJ (US)

( * ) Notice: Subject to any disclaimer, the term of this patent is extended or adjusted under 35 U.S.C. 154(b) by 54 days.

This patent is subject to a terminal disclaimer.

(21) Appl. No.: 14/286,218

(22) Filed: May 23, 2014

(65) Prior Publication Data

US 2014/0257437 A1 Sep. 11, 2014

Related U.S. Application Data

(63) Continuation of application No. 13/603,799, filed on Sep. 5, 2012, now Pat. No. 8,918,178, which is a continuation-in-part of application No. 13/222,087, filed on Aug. 31, 2011, which is a continuation-in-part (Continued)

(51) Int. Cl.
*A61N 1/36* (2006.01)
*A61N 1/04* (2006.01)

(52) U.S. Cl.
CPC .......... *A61N 1/0456* (2013.01); *A61N 1/36014* (2013.01); *A61N 1/36053* (2013.01)

(58) Field of Classification Search
CPC .................. A61N 1/36014; A61N 1/0456
See application file for complete search history.

(56) References Cited

U.S. PATENT DOCUMENTS

| | | | |
|---|---|---|---|
| 4,196,737 | A | 4/1980 | Bevilacqua |
| 5,458,141 | A | 10/1995 | Neil |
| 5,983,131 | A | 11/1999 | Weaver et al. |
| 6,341,236 | B1 | 1/2002 | Osorio et al. |

(Continued)

FOREIGN PATENT DOCUMENTS

| | | |
|---|---|---|
| WO | WO 93/01862 | 2/1993 |
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Christopher D Koharski
*Assistant Examiner* — Natasha Patel
(74) *Attorney, Agent, or Firm* — Dentons US LLP

(57) ABSTRACT

Devices, systems and methods are disclosed for treating a variety of diseases and disorders that are primarily or at least partially driven by an imbalance in neurotransmitters in the brain, such as asthma, COPD, depression, anxiety, epilepsy, fibromyalgia, and the like. The invention involves the use of an energy source comprising magnetic and/or electrical energy that is transmitted non-invasively to, or in close proximity to, a selected nerve to temporarily stimulate, block and/or modulate the signals in the selected nerve such that neural pathways are activated to release inhibitory neurotransmitters in the patient's brain.

26 Claims, 20 Drawing Sheets

Related U.S. Application Data of application No. 13/183,765, filed on Jul. 15, 2011, now Pat. No. 8,874,227, application No. 14/286,218, filed on May 23, 2014, which is a continuation-in-part of application No. 13/183,721, filed on Jul. 15, 2011, now Pat. No. 8,676,324, application No. 14/286,218, which is a continuation-in-part of application No. 13/109,250, filed on May 17, 2011, now Pat. No. 8,676,330, application No. 14/286,218, which is a continuation-in-part of application No. 13/075,746, filed on Mar. 30, 2011, now Pat. No. 8,874,205.

(60) Provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011.

(56) References Cited

U.S. PATENT DOCUMENTS

| | | | |
|---|---|---|---|
| 6,463,327 | B1 | 10/2002 | Lurie et al. |
| 6,587,719 | B1 | 7/2003 | Barrett et al. |
| 6,610,713 | B2 | 8/2003 | Tracey |
| 7,797,041 | B2 | 9/2010 | Libbus et al. |
| 2002/0099417 | A1 | 7/2002 | Naritoku et al. |
| 2002/0183237 | A1 | 12/2002 | Puskas |
| 2004/0243182 | A1 | 12/2004 | Cohen et al. |
| 2004/0249416 | A1 | 12/2004 | Yun et al. |
| 2005/0021092 | A1 | 1/2005 | Yun et al. |
| 2005/0065574 | A1 | 3/2005 | Rezai |
| 2005/0137644 | A1 | 6/2005 | Bojeva et al. |
| 2006/0074284 | A1 | 4/2006 | Juola et al. |
| 2006/0100668 | A1 | 5/2006 | Ben-David et al. |
| 2006/0100671 | A1 | 5/2006 | Ridder |
| 2006/0173510 | A1 | 8/2006 | Besio et al. |
| 2006/0178703 | A1 | 8/2006 | Huston et al. |
| 2007/0027496 | A1 | 2/2007 | Parnis et al. |
| 2007/0066997 | A1* | 3/2007 | He .................. A61N 1/372 607/3 |
| 2007/0123952 | A1 | 5/2007 | Strother et al. |
| 2007/0142886 | A1 | 6/2007 | Fischell et al. |
| 2007/0150006 | A1 | 6/2007 | Libbus et al. |
| 2007/0156182 | A1* | 7/2007 | Castel .............. A61N 1/36014 607/2 |
| 2007/0255085 | A1* | 11/2007 | Kishawi ............ A61N 2/002 600/9 |
| 2007/0276449 | A1 | 11/2007 | Gunter et al. |
| 2008/0021512 | A1 | 1/2008 | Knudson et al. |
| 2008/0027513 | A1 | 1/2008 | Carbunaru |
| 2008/0045776 | A1 | 2/2008 | Fischell et al. |
| 2008/0051852 | A1 | 2/2008 | Dietrich et al. |
| 2008/0091256 | A1* | 4/2008 | Libbus .............. A61N 1/36017 607/149 |
| 2008/0177190 | A1 | 7/2008 | Libbus et al. |
| 2008/0208266 | A1 | 8/2008 | Lesser et al. |
| 2008/0306325 | A1 | 12/2008 | Burnett et al. |
| 2009/0157149 | A1 | 6/2009 | Wahlgren et al. |
| 2009/0234419 | A1 | 9/2009 | Maschino et al. |
| 2009/0287035 | A1 | 11/2009 | Dietrich et al. |
| 2010/0286553 | A1 | 11/2010 | Feler et al. |
| 2011/0046432 | A1 | 2/2011 | Simon et al. |
| 2011/0152967 | A1 | 6/2011 | Simon et al. |
| 2011/0213295 | A1 | 9/2011 | Henley et al. |
| 2011/0224749 | A1 | 9/2011 | Ben-David et al. |
| 2011/0230701 | A1 | 9/2011 | Simon et al. |
| 2012/0029601 | A1 | 2/2012 | Simon et al. |
| 2012/0283697 | A1 | 11/2012 | Kim et al. |
| 2012/0303080 | A1 | 11/2012 | Ben-David et al. |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

* cited by examiner

■ Histamine
□ Histamine + VNS

■ Histamine
□ Histamine + VNS

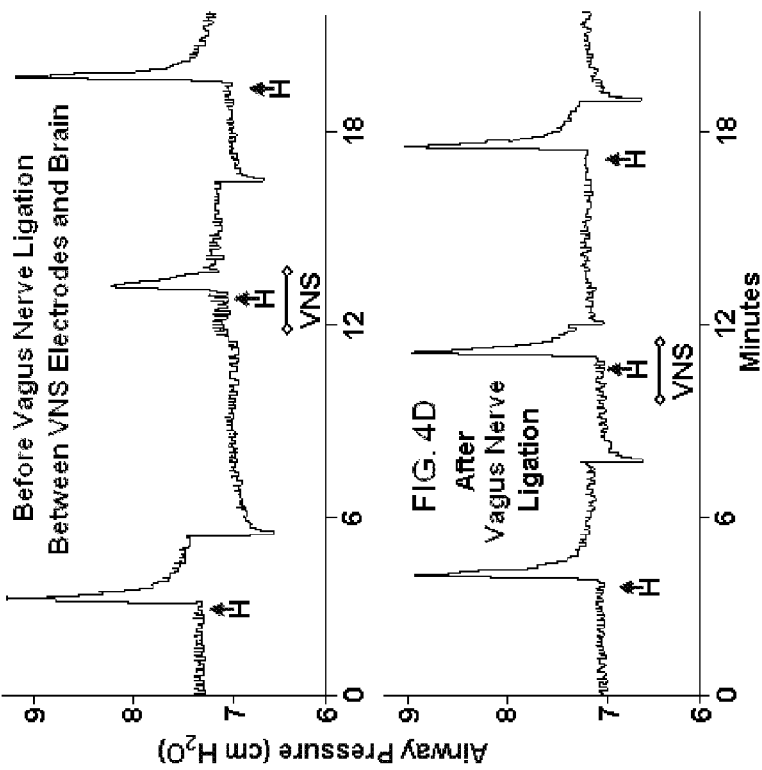
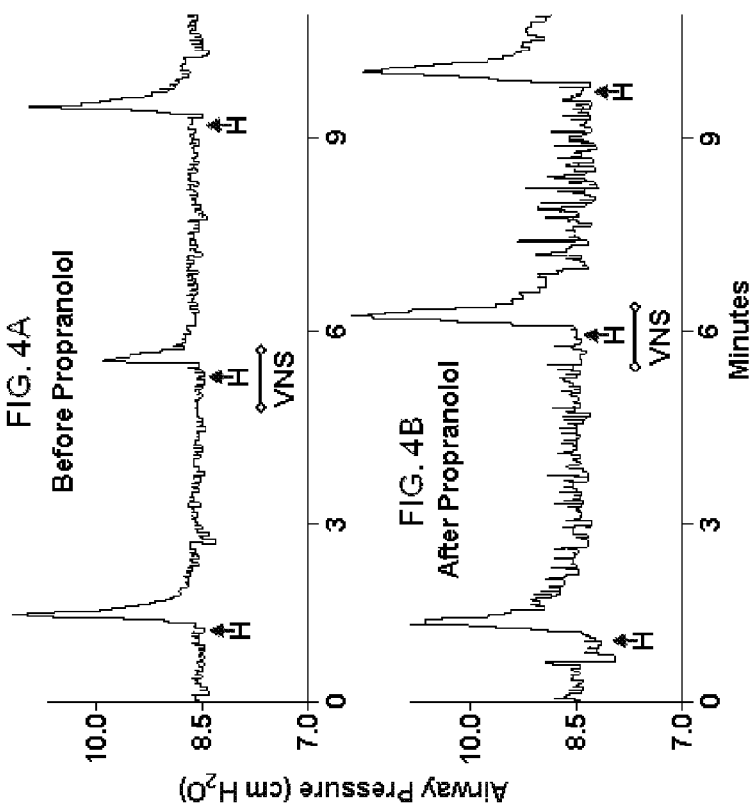

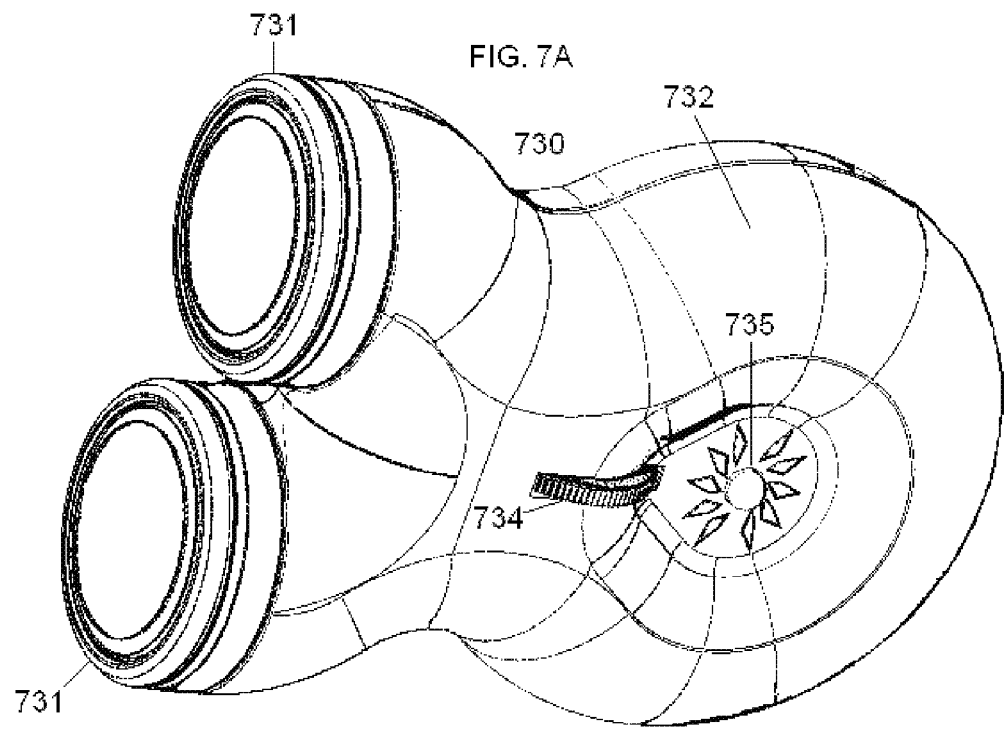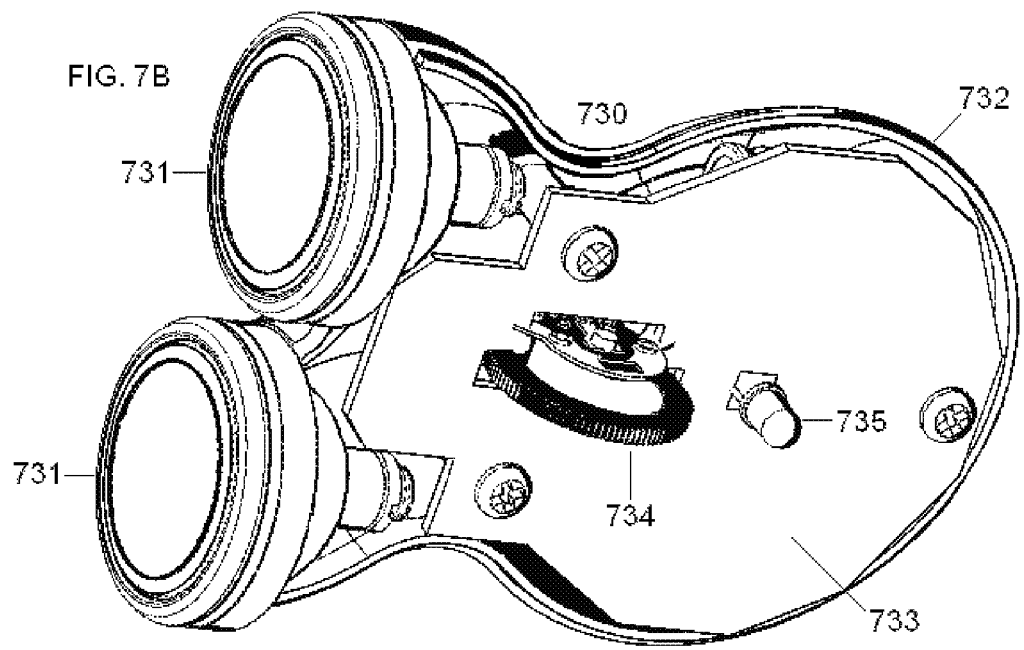

FIG. 13

| Subject ID | Medication | Administered | Indication | Dose | Freq. | Route |
|---|---|---|---|---|---|---|
| 03-001 | Ventolin[1] | Pre and post stim | Bronchospasm | 5 | x 2 | Inhaled |
| 02-001 | Berotec[2] | Post stim | Wheeze/tight chest | 1.25 mg | x 1 | Inhaled |
| 02-002 | Perfalgan[3] | Pre stim | Pain management | 1g | x 1 | IV |
|  | Atrovent[4] | Post stim | Asthma | 0.5mg | x 1 | Inhaled |
|  | Berotec[2] | Post stim | Asthma | 1.25mg | x 1 | Inhaled |
|  | Aminophylline[5] | Post stim | Asthma | No data | x 1 | IV |
| 02-003 | Atrovent[4] | Pre and post stim | Asthma | 0.5 mg | x 2 | Inhaled |
|  | Berotec[2] | Pre and post stim | Asthma | 1.25 mg | x 2 | Inhaled |
| 04-001 | Combivent[1] | Pre stim | Bronchospasm | 0.5/25mg | x 1 | Inhaled |
|  | Pulmicort[5] | No data | Bronchospasm | 0.5 mg | x 1 | Inhaled |
|  | Solu-cortef[6] | Post stim | Bronchospasm | 200 mg | x 1 | IV |
|  | Berotec[2] | Post stim | Bronchospasm | 1.25 mg | x 1 | Inhaled |
|  | Aminophylline[5] | Post stim | Bronchospasm | 250 mg | x 1 | IV |
| 01-001 | Atrovent | Post stim | Asthma | 1.25 mg | x 1 | Inhaled |
|  | Berotec | Post stim | Asthma | 0.5 mg | x 1 | Inhaled |
|  | Solucortef | Pre stim | Asthma | 200 mg | x 1 | IV |

[1]Albuterol, [2]Beta 2-agonist, [3]Pain killer (Paracetamol), [4]Ipatropium, [5]Bronchodialtor, [6]Corticosteriod FIG. 16A
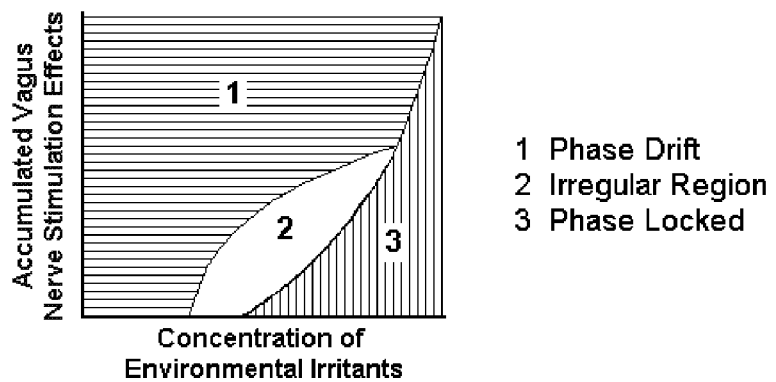
1 Phase Drift
2 Irregular Region
3 Phase Locked
FIG. 16B
1 Phase Drift
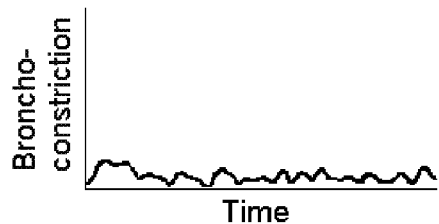
2 Irregular Region
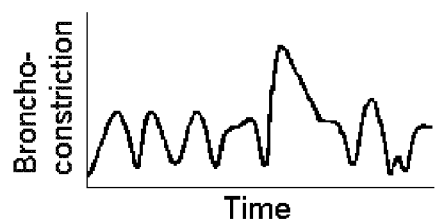
3. Phase Locked (in same potential well)
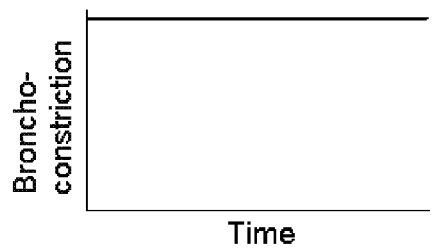

NON-INVASIVE VAGAL NERVE STIMULATION TO TREAT DISORDERS

CROSS REFERENCE TO RELATED APPLICATIONS

The present application is a continuation of U.S. application Ser. No. 13/603,799 filed Sep. 5, 2012; which is a continuation-in-part of U.S. application Ser. No. 13/222,087 filed Aug. 31, 2011, which is a continuation-in-part of U.S. application Ser. No. 13/183,765 filed Jul. 15, 2011 which claims the benefit of U.S. Provisional Application No. 61/488,208 filed May 20, 2011.

The present application also is a continuation-in-part of U.S. application Ser. No. 13/183,721 filed Jul. 15, 2011, which claims the benefit of U.S. Provisional Application No. 61/487,439 filed May 18, 2011.

The present application also is a continuation-in-part of U.S. application Ser. No. 13/109,250 filed May 17, 2011, now U.S. Pat. No. 8,676,324 issued Mar. 18, 2014, which claims the benefit of U.S. Provisional Application No. 61/471,405 filed Apr. 4, 2011.

The present application also is a continuation-in-part of U.S. application Ser. No. 13/075,746 filed Mar. 30, 2011, which claims the benefit of U.S. Provisional Application No. 61/451,259 filed Mar. 10, 2011.

BACKGROUND OF THE INVENTION

The field of the present invention relates to the delivery of energy impulses (and/or fields) to bodily tissues for therapeutic purposes. The invention relates more specifically to devices and methods for treating conditions associated with bronchial constriction, including: asthma, anaphylaxis, chronic obstructive pulmonary disease (COPD), exercise-induced bronchospasm and post-operative bronchospasm. The energy impulses (and/or fields) that are used to treat those conditions comprise electrical and/or electromagnetic energy, delivered non-invasively to the patient.

The use of electrical stimulation for treatment of medical conditions is well known. For example, electrical stimulation of the brain with implanted electrodes has been approved for use in the treatment of various conditions, including pain and movement disorders such as essential tremor and Parkinson's disease. Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; U.S. Pat. No. 6,871,099 entitled Fully implantable microstimulator for spinal cord stimulation as a therapy for chronic pain, to Whitehurst, et al].

Another example of electrical stimulation for treatment of medical conditions is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES D A, Brown V J. Vagal nerve stimulation: a review of its applications and potential mechanisms that mediate its clinical effects. Neurosci Biobehav Rev 29 (2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4; ANDREWS, R. J. Neuromodulation. I. Techniques-deep brain stimulation, vagus nerve stimulation, and transcranial magnetic stimulation. Ann. N.Y. Acad. Sci. 993 (2003): 1-13; LABINER, D. M., Ahern, G. L. Vagus nerve stimulation therapy in depression and epilepsy: therapeutic parameter settings. Acta. Neurol. Scand. 115(2007): 23-33].

Many such therapeutic applications of electrical stimulation involve the surgical implantation of electrodes within a patient. In contrast, devices used for the medical procedures that are disclosed herein do not involve surgery. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18 (2, 2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin. In what follows, comparison is sometimes made between the disclosed noninvasive methods, versus comparable invasive methods, for purposes of demonstrating feasibility and/or validation of the noninvasive methods.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. In contrast, the magnetic stimulators that are disclosed herein are relatively simpler devices that use considerably smaller currents within the stimulator coils. Accordingly, they are intended to satisfy the need for simple-to-use and less expensive non-invasive magnetic stimulation devices, for use in treating bronchoconstriction, as well as use in treating other conditions.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In the present application, the non-invasive delivery of energy is intended ultimately to dilate constricted bronchial passages of the lung, by relaxing bronchial smooth muscle and/or inhibit mucous production by the mucous glands. The smooth muscles that line the bronchial passages are controlled by a confluence of vagus and sympathetic nerve fiber plexuses. Spasms of the bronchi during asthma attacks, anaphylactic shock, and other pulmonary disorders can often be directly related to pathological signaling within these plexuses, as described below.

Asthma, and other airway occluding disorders resulting from immune responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated to be more than a hundred million people worldwide. Asthma's associated morbidity and mortality are rising in most countries despite the increasing use of anti-asthma drugs.

Asthma is characterized as a chronic inflammatory condition of the airways. Typical symptoms are coughing, wheezing, tightness of the chest and shortness of breath. Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

In general, there are three mechanisms that may be triggered in acute asthma (and other conditions, such as anaphylaxis, as described below). First, allergens induce smooth muscle bronchoconstriction through Ig-E dependent release of mast cell mediators such as histamines, prostaglandins, and leukotrienes. Second, airway hyper-responsiveness resulting from local and central neural reflex stimulation and by mediators of inflammation can increase bronchoconstriction. A third mechanism may stimulate mucosal thickening and edematous swelling of the bronchial walls through increased microvascular permeability and leakage.

In the case of asthma, it appears that the airway tissue has both (i) a hypersensitivity to an allergen that causes the overproduction of the cytokines that stimulate the cholinergic receptors of the nerves and/or (ii) a baseline high parasympathetic tone or a high ramp-up to a strong parasympathetic tone when confronted with any level of cholinergic cytokine. The combination can be lethal. Anaphylaxis appears to be mediated predominantly by the hypersensitivity to an allergen causing the massive overproduction of cholinergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. Publications cited below show that severing the vagus nerve (an extreme version of reducing the parasympathetic tone) has an effect similar to that of epinephrine on heart rate and bronchial diameter, in that the heart begins to race (tachycardia) and the bronchial passageways dilate.

Asthma is typically managed with inhaled medications that are taken after the onset of symptoms, or by injected and/or oral medications that are taken chronically. The medications typically fall into two categories: those that treat the inflammation, and those that treat the smooth muscle constriction. A first strategy is to provide anti-inflammatory medications, like steroids, to treat the airway tissue, reducing the tendency of the airways to over-release the molecules that mediate the inflammatory process. A second strategy is to provide a smooth muscle relaxant (e.g., an anticholinergic) to reduce the ability of the muscles to constrict. As treatments, anticholinergics improve lung function by modifying neural reflexes and parasympathetic vagal tone. While inferior to beta2-agonists as a primary treatment, inhaled anticholinergics are effective as an adjunct to beta2-agonists and the combination offers an advantage in reducing hospital admissions.

It is sometimes advised that patients rely on anti-inflammatory medications and avoidance of triggers, rather than on the bronchodilators, as their first line of treatment. For some patients, however, these medications, and even the bronchodilators are insufficient to stop the constriction of their bronchial passages. Tragically, more than five thousand people suffocate and die every year as a result of asthma attacks [NHLBI National Asthma Education and Prevention Program. Expert Panel Report 3 (EPR-3): Guidelines for the Diagnosis and Management of Asthma (NIH Publication No. 07-4051, Revised August 2007). pp 1-417. NHLBI Health Information Center, P.O. Box 30105. Bethesda, Md. 20824-0105; Padmaja SUBBARAO, Piush J. Mandhane, Malcolm R. Sears. Asthma: epidemiology, etiology and risk factors. CMAJ 181 (9, 2009): E181-E190; Lee MADDOX and David A. Schwartz. The pathophysiology of asthma. Annu. Rev. Med. 53(2002):477-98; ANDERSON G P. Endotyping asthma: new insights into key pathogenic mechanisms in a complex, heterogeneous disease. Lancet 372 (9643, 2008): 1107-1119; CAIRNS CB. Acute asthma exacerbations: phenotypes and management. Clin Chest Med. 27 (1, 2006):99-

108; RODRIGO G J. Predicting response to therapy in acute asthma. Curr Opin Pulm Med. 15 (1, 2009):35-38; Barbara P YAWN. Factors accounting for asthma variability: achieving optimal symptom control for individual patients. Primary Care Respiratory Journal 17 (3, 2008): 138-147].

Anaphylaxis ranks among the other airway occluding disorders as the most deadly, claiming many deaths in the United States every year. Anaphylaxis (the most severe form of which is anaphylactic shock) is a severe and rapid systemic allergic reaction to an allergen. Minute amounts of allergens may cause a life-threatening anaphylactic reaction. Anaphylaxis may occur after ingestion, inhalation, skin contact or injection of an allergen. Anaphylactic shock usually results in death in minutes if untreated. It is a life-threatening medical emergency because of rapid constriction of the airway, resulting in brain damage through oxygen deprivation.

The triggers for anaphylactic reactions range from foods (nuts and shellfish), to insect stings (bees), to medication (radio contrasts and antibiotics). It is estimated that 1.3 to 13 million people in the United States are allergic to venom associated with insect bites; 27 million are allergic to antibiotics; and 5-8 million suffer food allergies. In addition, anaphylactic shock can be brought on by exercise. Yet all such reactions are mediated by a series of hypersensitivity responses that result in uncontrollable airway occlusion driven by smooth muscle constriction, and dramatic hypotension that leads to shock. Cardiovascular failure, multiple organ ischemia, and asphyxiation are the most dangerous consequences of anaphylaxis.

Anaphylactic shock requires immediate advanced medical care. Current emergency measures include rescue breathing, administration of epinephrine, and/or intubation if possible. Rescue breathing may be hindered by the closing airway but can help if the victim stops breathing on his own. Clinical treatment typically includes administration of antihistamines (which inhibit the effects of histamine at histamine receptors, but which are usually not sufficient in anaphylaxis), and high doses of intravenous corticosteroids. Hypotension is treated with intravenous fluids and sometimes vasoconstrictor drugs. For bronchospasm, bronchodilator drugs such as salbutamol are administered [Phil LIEBERMAN. Epidemiology of anaphylaxis. Current Opinion in Allergy and Clinical Immunology 8(2008):316-320; Hugh A. SAMPSON et al. Second symposium on the definition and management of anaphylaxis: Summary report—Second National Institute of Allergy and Infectious Disease/Food Allergy and Anaphylaxis Network symposium. J Allergy Clin Immunol 117(2006):391-397; Angela W TANG. A practical guide to anaphylaxis. Am Fam Physician 68(2003):1325-1332 and 1339-1340].

The number of people who are susceptible to anaphylactic responses is estimated to be more than 40 million in the United States. Given the common mediators of both asthmatic and anaphylactic bronchoconstriction, it is not surprising that asthma sufferers are at higher than average risk for anaphylaxis. Tragically, many of these patients are fully aware of the severity of their condition, but nevertheless die while struggling in vain to manage the attack medically. Many of these fatal incidents occur in hospitals or in ambulances, in the presence of highly trained medical personnel who are powerless to break the cycle of inflammation and bronchoconstriction (and life-threatening hypotension in the case of anaphylaxis) affecting their patient. Unfortunately, prompt medical attention for anaphylactic shock and asthma are not always available. For example, epinephrine is not always available for immediate injection. Even in cases where medication and attention is available, life-saving measures are often frustrated because of the nature of the symptoms. Constriction of the airways frustrates resuscitation efforts, and intubation may be impossible because of swelling of tissues. Typically, the severity and rapid onset of anaphylactic reactions does not render the pathology amenable to chronic treatment, but requires more immediately acting medications. Epinephrine is among the most popular medications for treating anaphylaxis, commonly marketed in so-called "Epipen" formulations and administering devices, which potential sufferers carry with them at all times. In addition to serving as an extreme bronchodilator, epinephrine raises the patient's heart rate dramatically in order to offset the hypotension that accompanies many reactions. This cardiovascular stress can result in tachycardia, heart attacks and strokes.

Chronic obstructive pulmonary disease (COPD) is a major cause of disability and is the fourth leading cause of death in the United States. More than 12 million people are currently diagnosed with COPD. An additional 12 million likely have the disease but are unaware of their condition. COPD is a progressive disease that makes it increasingly difficult for the patient to breathe. COPD can cause coughing that produces large amounts of mucus, wheezing, shortness of breath, chest tightness and other symptoms. Cigarette smoking is the leading cause of COPD, although long term exposure to other lung irritants, such as air pollution, chemical fumes or dust may also contribute to COPD. In COPD, there is abnormally low air flow within the bronchial airways for a variety of reasons, including loss of elasticity in the airways and/or air sacs, inflammation and/or destruction of the walls between many of the air sacs and overproduction of mucus within the airways.

The term COPD includes two primary conditions: emphysema and chronic obstructive bronchitis. In emphysema, the walls between many of the air sacs are damaged, causing them to lose their shape and become floppy. This damage can also destroy the walls of the air sacs, leading to fewer and larger air sacs instead of many small ones. In chronic obstructive bronchitis, the patient suffers from permanently irritated and inflamed bronchial tissue that is slowly and progressively dying. This causes the lining to thicken and form thick mucus, making it difficult to breathe. Many of these patients also experience periodic episodes of acute airway reactivity (i.e., acute exacerbations), wherein the smooth muscle surrounding the airways goes into spasm, resulting in further constriction and inflammation of the airways. Acute exacerbations occur, on average, between two and three times a year in patients with moderate to severe COPD and are the most common cause of hospitalization in these patients, with mortality rates of approximately 11%. Frequent acute exacerbations of COPD cause lung function to deteriorate quickly, and patients never recover to the condition they were in before the last exacerbation. As with asthma, current medical management of these acute exacerbations is often insufficient [Dick D. BRIGGS Jr. Chronic obstructive pulmonary disease overview: prevalence, pathogenesis, and treatment. J Manag Care Pharm 10 (4 suppl S-a, 2004):S3-S10; Marc DECRAMER, Wim Janssens, Marc Miravitlles. Chronic obstructive pulmonary disease. Lancet 379(2012): 1341-1351].

Exercise-induced bronchospasm (EIB) results from a transient increase in airway resistance that occurs five to ten minutes after initiation of exercise. It produces symptoms such as shortness of breath, cough, wheezing, chest tightness, or pain. Eighty to ninety percent of patients with asthma also have EIB, but up to a quarter of non-asthmatic athletes may also experience EIB. The condition is usually treated with short-acting bronchodilator medication, with or without the addition of anti-inflammatory agents, taken 15 to 30 minutes before initiation of exercise. However, many patients do not respond to those treatments, or they experience unwanted side effects. Accordingly, one objective of the present invention is to provide an alternative to pharmacological treatment, through the use of noninvasive vagal nerve stimulation before and/or after exercise [Taru SINHA and Alan K. David. Recognition and management of exercise-induced bronchospasm. Am Fam Physician 67(2003):769-774].

Bronchospasm is one of the most significant respiratory complications that can occur during surgical anesthesia, and asthmatic patients, as well as some patients with COPD, are at elevated risk for it. Because the beneficial effects of steroids on airway reactivity occurs over a period of hours, patients at risk of experiencing bronchospasm during surgery are sometimes treated with steroids starting 24-48 h before surgery. The patients who are actually wheezing before surgery also receive treatment with inhaled beta-2 adrenergic agents and corticosteroids. Such wheezing may also be experienced by patients without pre-existing reactive airway disease, due to pulmonary edema, pneumothorax, drug reactions, aspiration, and endobronchial intubation. If the pharmacological treatment does not stop or prevent the wheezing, the surgery may be deferred, but this is not always practical or possible in view of the need for surgery. Accordingly, one objective of the present invention is to provide an alternative to pharmacological treatment, through the use of noninvasive vagal nerve stimulation before surgery.

Despite precautions and pre-treatments, bronchospasm may nevertheless occur during surgery, in which case, beta-2 adrenergic agents may also be administered through an endotracheal tube. For some patients, those agents may not be effective or are otherwise contraindicated, and the bronchospasm may continue even after the surgery is completed. Accordingly, another objective of the present invention is to provide an alternative to pharmacological treatment for bronchospasm that occurs during and after surgery, through the use of noninvasive vagus nerve stimulation [Peter ROCK and Preston B. Rich. Postoperative pulmonary complications. Current Opinion in Anaesthesiology 16(2003): 123-132].

Unlike cardiac arrhythmias, which can be treated chronically with pacemaker technology, or in emergent situations with defibrillators (implantable and external), there is no commercially available medical equipment that can chronically reduce the baseline sensitivity of the smooth muscle tissue in the airways, to reduce the predisposition to asthma attacks, to reduce the symptoms of COPD or to break the cycle of bronchial constriction associated with an acute asthma attack or anaphylaxis. Therefore, there is a need in the art for new products and methods for treating the immediate symptoms of bronchial constriction resulting from pathologies such as anaphylactic shock, asthma, COPD, exercise-induced bronchospasm, and post-operative bronchospasm. In particular, there is a need in the art for non-invasive devices and methods to treat the immediate symptoms of bronchial constriction.

Although energy has been applied previously to patients in such a way as to bring about bronchodilation, those investigations involve methods that are invasive. For example, U.S. Pat. No. 7,740,017, entitled Method for treating an asthma attack, to DANEK et al., discloses an invasive method for directing radio frequency energy to the lungs to bring about bronchodilation. U.S. Pat. No. 7,264,002, entitled Methods of treating reversible obstructive pulmonary disease, to DANEK et al., discloses methods of treating an asthmatic lung invasively, by advancing a treatment device into the lung and applying energy. Those invasive methods attempt to dilate the bronchi directly, rather than to stimulate nerve fibers that in turn bring about bronchodilation.

In contrast, the present invention discloses the use of noninvasive electrical stimulation of the vagus nerve (VNS) to dilate constricted bronchi. U.S. Pat. No. 6,198,970, entitled Method and apparatus for treating oropharyngeal respiratory and oral motor neuromuscular disorders with electrical stimulation, to FREED et al., describes noninvasive electrical stimulation methods for the treatment of asthma and COPD, but they involve direct stimulation of muscles instead of the vagus nerve. The present invention is unexpected because previous reports teach away from the use of (invasive or noninvasive) VNS to treat bronchoconstriction. Thus, in most subjects with asthma, vagal nerve activity contributes in varying degree to bronchoconstriction [OKAYAMA M, Yafuso N, Nogami H, et al. A new method of inhalation challenge with propranolol: comparison with methacholine-induced bronchoconstriction and role of vagal nerve activity. J Allergy Clin Immunol. 80(1987):291-9]. In fact, a clinical report suggests that vagal nerve stimulation may cause bronchoconstriction [BIJWADIA J S, Hoch R C, Dexter D D. Identification and treatment of bronchoconstriction induced by a vagus nerve stimulator employed for management of seizure disorder. Chest 127 (1, 2005):401-402]. Yet other reports list dyspnea or shortness of breath as common side effects of VNS, which is contrary to the objectives of the present invention [MORRIS G L 3rd, Mueller W M. Long-term treatment with vagus nerve stimulation in patients with refractory epilepsy. The Vagus Nerve Stimulation Study Group E01-E05. Neurology 53(1999):1731-5; Su Jeong Y O U, Hoon-Chul Kang, Heung Dong Kim, Tae-Sung Ko, Deok-Soo Kim, Yong Soon Hwang, Dong Suk Kim, Jung-Kyo Lee, Sang Keun Park. Vagus nerve stimulation in intractable childhood epilepsy: a Korean multicenter experience. J Korean Med Sci 22(2007):442-445; RUSH A J, Sackeim H A, Marangell L B, et al. Effects of 12 months of vagus nerve stimulation in treatment-resistant depression: a naturalistic study. Biol Psychiatry 58(2005): 355-363]. These clinical reports that VNS produces symptoms of bronchoconstriction may be understood from animal experiments that also teach away from the use of VNS to treat bronchoconstriction [BLABER L C, Fryer A D, Maclagan J. Neuronal muscarinic receptors attenuate vagally-induced contraction of feline bronchial smooth muscle. Br J Pharmacol 86(1985):723-728].

The vagus nerve innervates the heart, which raises additional concerns that even if VNS could be used to dilate bronchi, such vagus nerve stimulation could trigger cardiac or circulatory problems, including bradycardia, hypotension, and arrhythmia, particularly if the right vagus nerve is stimulated [SPUCK S, Tronnier V, Orosz I, Schonweiler R, Sepehrnia A, Nowak G, Sperner J. Operative and technical complications of vagus nerve stimulator implantation. Neurosurgery 67 (2 Suppl Operative, 2010):489-494; SPUCK S, Nowak G, Renneberg A, Tronnier V, Sperner J. Right-sided vagus nerve stimulation in humans: an effective therapy? Epilepsy Res 82 (2008):232-234; THOMPSON G W, Levett J M, Miller S M, Hill M R, Meffert W G, Kolata R J, Clem M F, Murphy D A, Armour J A. Bradycardia induced by intravascular versus direct stimulation of the vagus nerve. Ann Thorac Surg 65 (3, 1998):637-42; SRINIVASAN B, Awasthi A. Transient atrial fibrillation after the implantation of a vagus nerve stimulator. Epilepsia 45 (12, 2004):1645]. In fact, vasovagal reactions are classically brought about by a triggering stimulus to the vagus nerve, resulting in simultaneous enhancement of parasympathetic nervous system (vagal) tone and withdrawal of sympathetic nervous system tone.

Accordingly, we performed experiments, which are described herein, showing first that invasive electrical stimulation of the vagus nerve can in fact produce bronchodilation without first producing bronchoconstriction [Thomas J. HOFFMANN, Steven Mendez, Peter Staats, Charles W. Emala, Puyun Guo. Inhibition of Histamine-Induced Bronchoconstriction in Guinea Pig and Swine by Pulsed Electrical Vagus Nerve Stimulation. Neuromodulation 12 (4, 2009): 261-269]. The success of those and subsequent experiments motivated the present disclosure that noninvasive methods and devices can also produce bronchodilation in humans, provided that the disclosed special devices and stimulation methods are used. Those devices and methods address not only the problems of producing bronchodilation and avoiding the production of abnormal heart rate or blood pressure, but also the problem of stimulating at the skin of the patient in such a way that a vagus nerve is selectively modulated, and in such a way that side effects including muscle twitching and stimulation pain are minimized or avoided.

SUMMARY OF THE INVENTION

The present invention involves devices and methods for the treatment of a variety of diseases and disorders that are primarily or at least partially driven by an imbalance in neurotransmitters in the brain, such as asthma, COPD, depression, anxiety, epilepsy, fibromyalgia, and the like. The invention involves the use of an energy source comprising magnetic and/or electrical energy that is transmitted non-invasively to, or in close proximity to, a selected nerve to temporarily stimulate, block and/or modulate the signals in the selected nerve.

In one aspect of the invention, a method of treating a disorder comprises positioning a device adjacent to a skin surface of the patient, generating one or more electrical impulses with said device and transmitting the electrical impulses to a vagus nerve in the patient. The electrical impulses are sufficient to generate an electric field at the vagus nerve above a threshold for generating action potentials within fibers of the vagus nerve responsible for activating neural pathways causing release of inhibitory neurotransmitters within a brain of the patient. In a preferred embodiment, the inhibitory neurotransmitters are one or more of the following: GABA, serotonin and/or norepinephrine.

The applicant has discovered that many seemingly disparate disorders may, in fact, have common causes that manifest into different symptoms or disorders in different individuals. Specifically, the applicant has discovered that in certain individuals who may suffer from disorders, such as depression, asthma, COPD, migraine, cluster headache, anxiety, fibromyalgia, epilepsy and the like, certain areas of the brain are prone to periodic or continuous excessive excitatory neurotransmitter levels. These periodic excessive excitatory neurotransmitter levels can be caused by certain "triggers", such as noxious substances entering the lungs that cause airway reactivity or other triggers, such as chocolate or seafood that can cause migraines in certain individuals. In other cases, the patient may have pathologically high excitatory neurotransmitter levels on a continuous basis without any particular trigger. One example, of an excitatory neurotransmitter is glutamate, which is known to be associated with migraines.

The excessive excitatory neurotransmitter levels in a patient's brain can be caused by inaccurate signals from the body transmitted through the vagus nerve or other nerves or these excessive levels can be caused by the brain overreacting to normal signals coming from the body. In some cases, these excessive excitatory neurotransmitter levels may be caused by inappropriate inactivity in the production and/or release of inhibitory neurotransmitters, such as GABA, serotonin and/or norepinephrine. A reduced level of these inhibitory neurotransmitter levels can result in excessive levels of the excitatory neurotransmitters that they are meant to balance.

The present invention seeks to address this inbalance in neurotransmitters in the brain that can result in many of the disorders mentioned above. Specifically, afferent nerve fibers in the vagus nerve are stimulated with the devices, signals and methods described above to heighten activity in areas of the brain (e.g., the periaqueducatal gray, locus ceruleus and/or raphe nuclei) resulting in the release of inhibitory neurotransmitter levels, such as GABA, norephinephrine and/or serotonin). For example, as discussed above, heightened activity in the locus coeruleus will result in a release of norephinephrine or an increase the release of norephinephrine. This release of inhibitory neurotransmitters suppresses the excessive excitatory neurotransmitters and creates balance in the brain such that the brain either does not overreact to certain stimuli and/or to modulate the pathologically high level of excitatory neurotransmitters.

Another of the key advantages with the present invention is that the electrical field is above the threshold for generating action potentials within A and B fibers of the vagus nerve but below the threshold for the C fibers. Thus, the A and B fibers are selectively stimulated without stimulating the C fibers of the vagus nerve. The method of the present invention allows for selective stimulation of nerves responsible for activating neural pathways that will cause the release of inhibitory neurotransmitters within the brain to treat a variety of disorders in a patient. At the same time, the stimulation has substantially no effect on heart rate or blood pressure and it will not cause bronchoconstriction.

In a preferred embodiment, the electric field at the vagus nerve is between about 10 to 600 V/m and more preferably less than 100 V/m. The electrical field gradient is preferably greater than 2 V/m/mm. The electrical impulses are substantially constrained from modulating the nerves between the outer skin surface of the patient and the vagus nerve. The electric field is preferably not sufficient to produce substantial movement of the skeletal muscles of the patient.

In one embodiment of the invention, the stimulator comprises a source of electrical power and two or more remote electrodes that are configured to stimulate a deep nerve relative to the nerve axis. In one embodiment, the stimulator comprises two electrodes that lie side-by-side within separate stimulator heads, wherein the electrodes are separated by electrically insulating material. Each electrode is in continuous contact with an electrically conducting medium that extends from the interface element of the stimulator to the electrode. The interface element also contacts the patient's skin when the device is in operation.

Current passing through an electrode may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and an electrical field gradient of greater than 2 V/m/mm. The electric fields produced by the present invention at the vagus nerve are generally sufficient to excite all myelinated A and B fibers, but not the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient, such as bronchodilation. Such a suitable waveform and parameters are simultaneously selected to avoid substantially stimulating nerves and tissue other than the target nerve, particularly avoiding the stimulation of nerves that produce pain.

In one embodiment, the present invention is particularly useful for the acute relief of symptoms associated with bronchial constriction, e.g., asthma attacks, COPD exacerbations and/or anaphylactic reactions. The teachings of the present invention provide an emergency response to such acute symptoms, by producing an almost immediate airway dilation, enabling subsequent adjunctive measures (such as the administration of epinephrine) to be effectively employed. The invention may be useful for treating bronchoconstriction in patients who cannot tolerate the side effects of albuterol or other short acting β-agonists, who do not gain sufficient benefit from anticholinergic medications including tioproprium bromide, or whose airway resistance is too high to get adequate benefit from inhaled medications. In preferred embodiments, the disclosed methods and devices do not produce clinically significant side effects, such as changes in heart rate or blood pressure.

One aspect of the method includes stimulating, inhibiting, blocking or otherwise modulating nerves that directly or indirectly modulate parasympathetic ganglia transmission, by stimulation or inhibition of preganglionic to postganglionic transmissions. According to this feature of the invention, noninvasive vagus nerve stimulation with the disclosed devices can activate pathways causing release of norepinephrine, serotonin and GABA (inhibitory neurotransmitters) onto airway-related vagal preganglionic neurons (AVPNs), thereby preventing release of acetylcholine in the airways, and resulting in bronchorelaxation. These neural pathways also innervate the mucous glands in the lungs and other airway passages. Thus, the activation of these neural pathways also inhibits mucous production in the airways, increasing airflow to and from the patient's lungs.

In yet another aspect of the present invention, the selected nerve fibers comprise those that send an afferent vagal signal to the brain, which then triggers an efferent sympathetic signal to stimulate the release of catecholamines (comprising endogenous beta-agonists, epinephrine and/or norepinephrine) from the adrenal glands and/or from nerve endings that are within the lung or distributed throughout the body.

The stimulating step is preferably carried out without substantially stimulating excitatory nerve fibers, such as parasympathetic cholinergic nerve fibers, that are responsible for increasing the magnitude of constriction of smooth muscle. In this manner, the activity of the nerve fibers responsible for bronchodilation are increased without increasing the activity of the cholinergic fibers, which would otherwise induce further constriction of the smooth muscle. Alternatively, the method may comprise the step of actually inhibiting or blocking these cholinergic nerve fibers such that the nerves responsible for bronchodilation are stimulated while the nerves responsible for bronchial constriction are inhibited or completely blocked. This blocking/inhibiting signal may be separately applied to the inhibitory nerves; or it may be part of the same signal that is applied to the nerve fibers directly responsible bronchodilation.

The method of treating bronchial constriction includes applying an energy impulse to a target region in the patient, preferably over a period of less than two minutes, and acutely reducing the magnitude of bronchial constriction in the patient. Preferably, the bronchodilation effect lasts from about 2 to 8 hours.

The novel systems, devices and methods for treating disorders are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

This application refers to the following patents and patent applications, the entire disclosures of which are hereby incorporated by reference for all purposes: U.S. patent application Ser. No. 13/005,005 filed Jan. 12, 2011, which is a continuation-in-part of U.S. patent application Ser. No. 12/964,050 filed Dec. 9, 2010, which claims the benefit of priority of U.S. Provisional Patent Application No. 61/415,469 filed Nov. 19, 2010 and is a continuation-in-part of U.S. patent application Ser. No. 12/859,568 filed Aug. 9, 2010, which is a continuation-in-part of U.S. patent application Ser. No. 12/408,131 filed Mar. 20, 2009 and a continuation-in-part application of U.S. patent application Ser. No. 12/612,177 filed Nov. 9, 2009 the entire disclosures of which are hereby incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIGS. 4A-4D is data from a guinea pig experiment showing that without propranolol pretreatment, the effect of vagus nerve stimulation was to reduce the magnitude of bronchoconstriction produced by histamine, but when propranolol was administered as a pretreatment, the VNS-mediated attenuation of bronchoconstriction was blocked (FIGS. 4A-4B); and ligating vagus nerves between the stimulator electrodes and the brainstem blocks the attenuation of bronchoconstriction, as compared with the situation prior to ligation (FIGS. 4C-4D).

FIGS. 7A-7D illustrate a dual-electrode stimulator according to an embodiment of the present invention, which is shown to house the stimulator's electrodes and electronic components (FIGS. 7A-7B), as well as showing details of the head of the dual-electrode stimulator (FIGS. 7C-7D).

FIG. 13 is a table showing the medications take prior to and after noninvasive vagus nerve stimulation, among six bronchoconstricted patients who appeared in an emergency department and who were stimulated two times, 30 minutes apart, for 90 seconds each.

FIGS. 16A-16B illustrate a phase diagram according to the present invention, which circumscribes regions where coupled nonlinear bronchial oscillators exhibit qualitatively different types of dynamics, as a function of the concentration of environmental irritants and of the cumulative magnitude of vagus nerve stimulation.

DETAILED DESCRIPTION OF THE PREFERRED EMBODIMENTS

Figure 1:
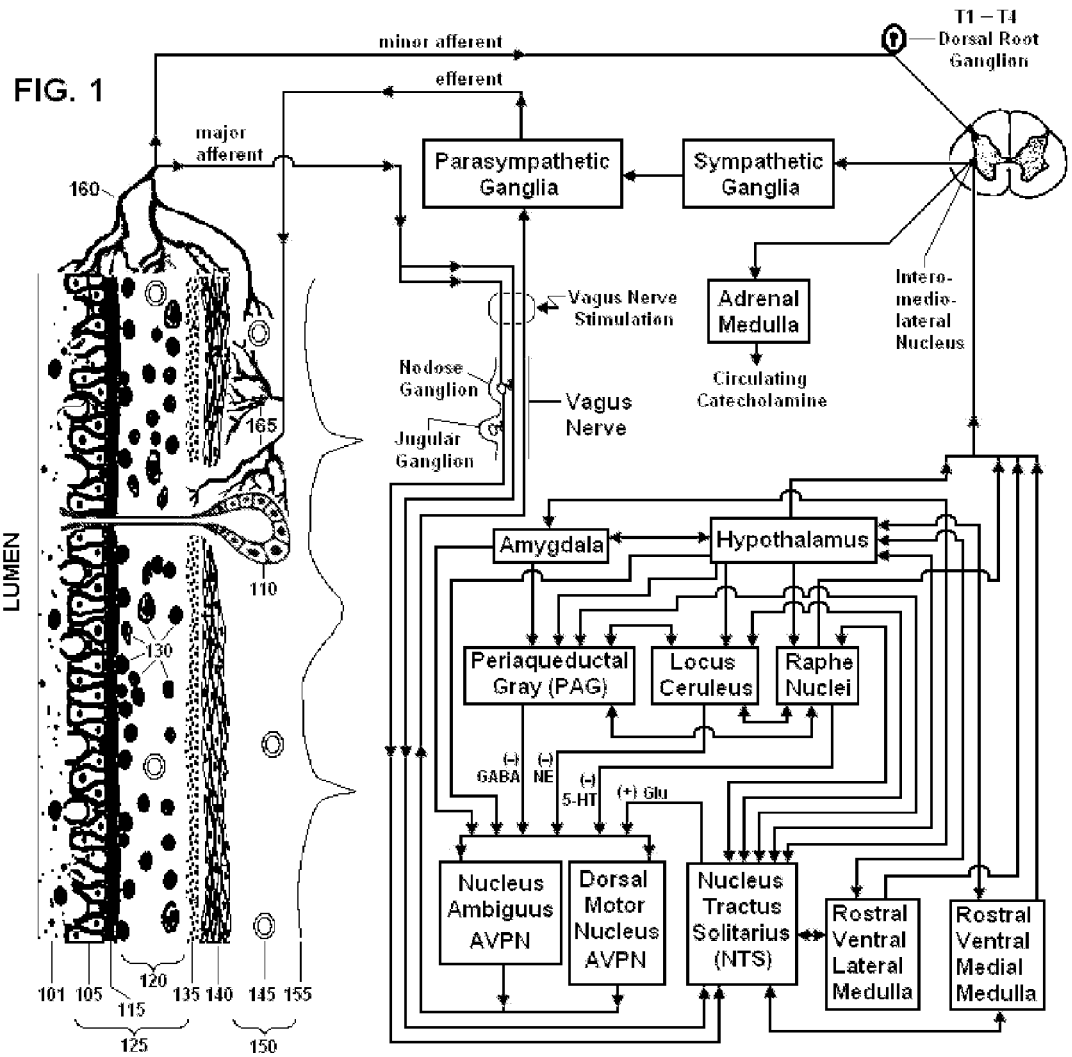
FIG. 1 shows a cross-section of a bronchial lumen that is innervated by afferent and efferent nerve fibers of a vagus nerve that is electrically stimulated in the present invention, as well as a diagram of brain/brainstem structures that participate in the nervous control of bronchial smooth muscle.

Once air is inhaled through the mouth or nose, it travels through the trachea and a progressively bifurcating system of bronchi (containing cartilage) and bronchioles (which contain little or no cartilage), until it finally reaches the alveoli, where the gas exchange of carbon dioxide and oxygen takes place. Through constriction or relaxation of smooth muscle within their walls, the bronchioles change diameter to either reduce or increase air flow. The bronchioles between the fourth and eighth bifurcation are thought to be most important in that regard. Normally, an increase in diameter (bronchodilation) to increase air flow is stimulated by circulating epinephrine (adrenaline) or sympathetic nerve fibers or so-called iNANC nerve fibers, and a decrease in diameter (bronchoconstriction) is stimulated by parasympathetic cholinergic nerve fibers, histamine, cold air, and chemical irritants. Reflexes have evolved to regulate the caliber of bronchioles, in which afferent nerves send state-dependent sensory signals to the central nervous system, which in turn sends efferent controlling signals back to the bronchi and bronchioles, thereby allowing smooth muscle (and other components) in the bronchi to adapt their caliber as needed to respond to such things as exercise, air-borne irritants, and infectious agents.

The present invention teaches non-invasive devices and methods for treating abnormal bronchial constriction, by stimulating selected nerve fibers that are responsible for reducing the magnitude of constriction of smooth bronchial muscle, such that the activity of those selected nerve fibers is increased and smooth bronchial muscle is dilated. In particular, the present invention provides methods and devices for immediate relief of acute symptoms associated with bronchial constriction such as asthma attacks, COPD exacerbations, anaphylactic reactions, exercise-induced bronchospasm, and post-operative bronchospasm. The stimulated nerve fibers are particularly those associated with a vagus nerve (tenth cranial nerve).

In a preferred embodiment, electrodes applied to the skin of the patient generate currents within the tissue of the patient. An objective of the invention is to produce and apply electrical impulses that interact with the signals of one or more nerves to achieve the therapeutic result of bronchodilation. Much of the disclosure will be directed specifically to treatment of a patient by stimulation in or around a vagus nerve, with devices positioned non-invasively on or near a patient's neck. In particular, the present invention can be used to directly or indirectly stimulate or otherwise modulate nerves that innervate bronchial smooth muscle. However, it will be appreciated that the devices and methods of the present invention can be applied to other tissues and nerves of the body, including but not limited to other parasympathetic nerves, sympathetic nerves, spinal or cranial nerves.

The methods described herein of applying an impulse of energy to a selected region of a vagus nerve may be refined to propagate signals directly, or indirectly via the central nervous system, to at least one of the anterior bronchial branches of a vagus nerve, or alternatively to at least one of the posterior bronchial branches thereof. Preferably the propagated impulse is provided to at least one of the anterior pulmonary or posterior pulmonary plexuses aligned along the exterior of the lung. As necessary, the impulse may be directed to nerves innervating only the bronchial tree and lung tissue itself. In addition, the impulse may be directed to a region of the vagus nerve to stimulate, block and/or modulate both the cardiac and bronchial vagal branches. As recognized by those having skill in the art, this embodiment should be carefully evaluated prior to use in patients known to have preexisting cardiac issues.

Topics that are presented below in connection with the disclosure of the invention include the following:

Overview of physiological mechanisms by which vagus nerve stimulation may modulate bronchial smooth muscle, e.g., bring about bronchodilation;

Description of Applicant's magnetic and electrode-based nerve stimulating/modulating devices, describing in particular the electrical waveform that is used to stimulate a vagus nerve;

Applicant's animal experiments demonstrating that the disclosed stimulation waveform and devices may bring about bronchodilation by particular physiological mechanisms;

Preferred embodiments of the magnetic stimulator;

Preferred embodiments of the electrode-based stimulator;

Application of the stimulators to the neck of the patient;

Measurements that are used to evaluate the state of a patient's bronchoconstriction;

Clinical experiments demonstrating that the disclosed stimulation waveform and devices bring about bronchodilation in humans without significant adverse events;

Use of the devices with feedback and feedforward to improve bronchodilation of individual patients;

Nonlinear feedforward model of bronchial oscillations, and the use of VNS to reverse bronchial-closing avalanches in asthma.

Overview of Physiological Mechanisms by which Vagus Nerve Stimulation May Bring about Bronchodilation A vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

A vagus nerve in man consists of over 100,000 nerve fibers (axons), mostly organized into groups. The groups are contained within fascicles of varying sizes, which branch and converge along the nerve, and which are surrounded by perineurium, epineurium, and fibrotic connective tissue. Each fiber normally conducts electrical impulses only in one direction, which is defined to be the orthodromic direction, and which is opposite the antidromic direction. Besides efferent output fibers that convey signals to the various organs in the body from the central nervous system, the vagus nerve conveys sensory information about the state of the body's organs back to the central nervous system. Some 80-90% of the nerve fibers in the vagus nerve are afferent (sensory) nerves communicating the state of the viscera to the central nervous system.

The largest nerve fibers within a left or right vagus nerve are approximately 20 µm in diameter and are heavily myelinated, whereas only the smallest nerve fibers of less than about 1 µm in diameter are completely unmyelinated. When the distal part of a nerve is electrically stimulated, a compound action potential is recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 µm diameter), A-beta fibers (afferent or efferent fibers, 5-12 µm), A-gamma fibers (efferent fibers, 3-7 µm), A-delta fibers (afferent fibers, 2-5 µm), B fibers (1-3 µm) and C fibers (unmyelinated, 0.4-1.2 µm). The diameters of group A and group B fibers include the thickness of the myelin sheaths.

In mammals, two vagal components have evolved in the brainstem to regulate peripheral parasympathetic functions. The dorsal vagal complex (DVC), consisting of the dorsal motor nucleus (DMNX) and its connections, controls parasympathetic function primarily below the level of the diaphragm, while the ventral vagal complex (VVC), comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, bronchodilation, vocalization and contraction of the facial muscles in relation to emotional states. Generally speaking, this portion of the vagus nerve regulates parasympathetic tone. The VVC inhibition is released (turned off) in states of alertness. This, in turn, causes cardiac vagal tone to decrease and airways to open, to support responses to environmental challenges.

The parasympathetic tone is balanced in part by sympathetic innervations, which generally speaking supplies signals tending to relax the bronchial muscles, so that over-constriction does not occur. Overall, airway smooth muscle tone is dependent on several factors, including parasympathetic input, inhibitory influence of circulating epinephrine, iNANC nerves and sympathetic innervations of the parasympathetic ganglia. Stimulation of certain nerve fibers of the vagus nerve (up-regulation of tone), such as occurs in asthma or COPD attacks or anaphylactic shock, results in airway constriction and a decrease in heart rate. In general, the pathology of severe asthma, COPD and anaphylaxis appear to be mediated by inflammatory cytokines that overwhelm receptors on the nerve cells and cause the cells to massively upregulate the parasympathetic tone.

The role of a vagus nerve in controlling the caliber of a bronchus or bronchiole lumen is illustrated in FIG. 1. The bronchus or bronchiole is tubular in shape, and the left side of FIG. 1 shows a cross-section of its anatomy, viewed left-to-right from its central air-containing lumen to its periphery. The figure as drawn is a composite of structures that are found in large bronchi to small bronchioles, and it is not intended to be a complete representation of the bronchioles and their control. The air in the lumen is in contact with a layer of mucus 101. That layer comprises water and various macromolecular glycoproteins disposed in a gel/sol structure. It may also contain trapped inhaled particles and cells that participate in an immune response to inhaled viruses, bacteria and other antigens. The mucus is produced by cells in and near the epithelial layer 105 that lines the inner surface of the airway. The epithelium of the larger airways comprises ciliated, basal, goblet, brush, and small-granule cells, among which the goblet cells are responsible for much of the mucus. Larger airways also contain glands 110 that contain two secretory cell types: the serous and the mucous cell, secretions from which reach the lumen via a duct inserted through the epithelium 105. The epithelium of the distal airways consists mainly of ciliated and bronchiolar exocrine (Clara) cells, and the latter cells produce much of the mucus there. Transport of the mucus to the mouth is due to ciliary beating of ciliated cells of the epithelium 105 and to airflow.

A basement membrane 115 anchors the epithelium 105 to loose connective tissue that lies beneath the membrane. The lamina propria 120 is the layer of connective tissue that lies immediately beneath the epithelium, which together with the epithelium constitutes the mucosa (or mucous membrane) 125.

Cells that participate in host defense are present in the lamina propria 120, such as cells of the innate- and adaptive-immune systems, including macrophages, neutrophils, eosinophils, dendritic cells, mast cells, natural killer cells, and lymphocytes. Those immune cells 130, interacting with the epithelial cells 105, are responsible for much of the defensive properties of the airways [Nicholas A. EISELE and Deborah M. Anderson. Host defense and the airway epithelium: frontline responses that protect against bacterial invasion and pneumonia. Journal of Pathogens 2011:249802, pp. 1-15; Laurent P. NICOD. Pulmonary defense mechanisms. Respiration 66(1999):2-11].

Variable amounts of elastin may also be present in the lamina propria 120, or the elastin may appear as a layer 135 under a generally separated or discontinuous circumferential layer of smooth muscle 140. Contraction and relaxation of the smooth muscle 140 modulates the diameter of the bronchiole and its lumen, which thereby modulates the flow of air between the trachea and the alveoli, where gas exchange occurs.

Capillaries or other small blood vessels 145 are also present in the lamina propria 120, and blood vessels 145 (arteries and veins, e.g. venules) occupy the region of adventitia 150 between the smooth muscle layer 140 and the peripheral site of bronchiolar attachment 155 to alveoli or other lung structure such as cartilage [John WIDDICOMBE. The airway vasculature. Experimental Physiology 78(1993):433-452].

Afferent nerve fibers 160 within the bronchi and bronchioles sense the status of the airways and send that information towards the central nervous system. The brainstem and other central nervous tissue in turn process and integrate that information, along with information sensed from other lung structures and other organs (e.g., respiratory muscles, vasculature, heart, etc.), then send control signals along efferent nerve fibers 165 to directly or indirectly modulate the activity of structures within the bronchi and bronchioles. Those neuronally-modulated structures are primarily the smooth muscle 140 and the secretion glands 110, but the blood vessels 145, the immune cells 130 within the lamina propria, and cells within the epithelium 105 may be modulated as well.

Although both the sympathetic and parasympathetic branches of the autonomic nervous system innervate the airways, the parasympathetic branch dominates, especially with respect to control of airway smooth muscle and secretions. Parasympathetic tone in the airways is regulated by reflex activity often initiated by activation of airway stretch receptors and polymodal nociceptors, as now described [Marie-Claire MICHOUD. Neurohumoral control of the airways. Chapter 30, pp. 363-370 In: Physiologic Basis of Respiratory Disease. Q Hamid, S Shannon and J Martin, eds. Hamilton, Ontario: B C Decker, 2005; BARNES P J. Modulation of neurotransmission in airways. Physiol Rev 1992; 72:699-729].

The afferent parasympathetic nerve fibers are typically subclassified as low threshold mechanosensors and nociceptive-like fibers (slow-conducting, capsaicin-sensitive bronchopulmonary C fibers). The low threshold mechanosensors can be further subclassified as slowly (SAR) and rapidly (RAR) adapting stretch receptors. Less populous receptor types, e.g. those that respond particularly to punctate mechanical stimulation or rapid changes in pH, also exist [Michael J. CARR and Bradley J. Undem. Bronchopulmonary afferent nerves. Respirology 8(2003):291-301; Thomas TAYLOR-CLARK and Bradley J. Undem. Transduction mechanisms in airway sensory nerves. J Appl Physiol 101 (2006):950-959; Giuseppe Sant' AMBROGIO. Nervous receptors of the tracheobronchial tree. Ann. Rev. Physiol. 49(1987):611-627].

SARs lie in close association with airway smooth muscle and respond to stretch of the airway wall. Some fire throughout the respiratory cycle and others burst in response to lung inflation, with progressive increases in discharge rate as a function of lung volume.

RARs are found throughout the tracheobronchial tree, primarily in and under the epithelium and in close approximation to bronchial venules. They are exquisitely sensitive to mechanical stimuli and respond with a rapidly adapting discharge to large and rapid lung inflations and deflations. RARs are also stimulated or sensitized by intraluminal chemical irritants, smoke, dust, and environmental toxins. Because of the latter properties they are also known as irritant receptors.

Bronchial C-fiber receptors, which are innervated by non-myelinated vagal afferent fibers, lie in the walls of the conducting airways. Their endings extend into the space between epithelial cells or form a plexus immediately beneath the basement membrane. The nociceptive nerves are more responsive to chemical mediators than the stretch-sensitive RAR and SAR fibers (e.g., nicotine, acids, histamine, serotonin, bradykinin, and other mediators of inflammation). The C fibers are often referred to as "polymodal" fibers, because they respond to a broad range of stimuli. Activation of sensory C fiber receptors in the airways mucosa sets up axon reflexes with release of sensory neuropeptides. These neuropeptides cause vasodilatation, possibly with edema and plasma exudation, submucosal gland secretion, structural and functional changes in the epithelium, and possibly airway smooth muscle contraction [M. KOLLARIK, F. Rua, M. Brozmanova. Vagal afferent nerves with the properties of nociceptors. Autonomic Neuroscience: Basic and Clinical 153(2010): 12-20].

The majority of afferent parasympathetic innervation to the lower airways is carried by the vagus nerves (See FIG. 1). The vagal afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 1). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra.

Terminations of each group of fibers (SAR, RAR, and C) are found in largely non-overlapping regions of the nucleus of the solitary tract (NTS, See FIG. 1). Second order neurons in the pathways from these receptors innervate neurons located in respiratory-related regions of the medulla, pons, and spinal cord. Those pathways control not only the bronchiole structures shown in FIG. 1, but also the rate and depth of respiration and cardiopulmonary activity more generally [Leszek KUBIN, George F. Alheid, Edward J. Zuperku, and Donald R. McCrimmon. Central pathways of pulmonary and lower airway vagal afferents. J Appl Physiol 101 (2006): 618-627; Jeffrey C. SMITH, Ana P. L. Abdala, Ilya A. Rybak and Julian F. R. Paton. Structural and functional architecture of respiratory networks in the mammalian brainstem. Phil. Trans. R. Soc. B 364(2009): 2577-2587].

Both afferent and efferent parasympathetic fibers traverse or skirt the nodose and jugular ganglia (See FIG. 1). With regard to the efferent parasympathetic fibers 165, which send control signals back to the bronchioles, preganglionic motor fibers (ganglionic branches) from the dorsal motor nucleus of the vagus and the special visceral efferents from the nucleus ambiguus descend to the nodose (inferior) vagal ganglion and form a band that skirts the ganglion. Thus, signals that are processed in the nucleus of the solitary tract (NTS) are sent to airway-related vagal preganglionic neurons (AVPNs), located in the most rostral parts of the dorsal vagal nucleus and in the rostral nucleus ambiguus. From these preganglionic neurons, cholinergic outflow is sent via descending efferent intramural parasympathetic ganglia and then to tracheobronchial effector systems. In particular, postganglionic efferent cholinergic fibers profusely innervate the smooth muscle 140 and the submucosal glands 110. In humans, there is comparatively little innervation of the airway epithelium 105, airway blood vessels 145, or lamina propria 120. Because the lamina propria is poorly innervated by efferent parasympathetic nerves in humans, cells of inflammatory and immune systems that are contained therein, such as macrophages, may receive little direct control there from those efferent nerves, although such control may be more significant in non-human species [CZURA C J, Tracey K J. Autonomic neural regulation of immunity. J Intern Med 257 (2, 2005): 156-66].

The acetylcholine that is released from the preganglionic and postganglionic nerve fibers acts on target cell membranes through muscarinic receptors, including M2 and M3. The M3 receptors are found on bronchial airway smooth muscle 140 and submucosal glands 110, causing smooth muscle contraction and secretion, when activated. Thus, contraction of airway smooth muscle is mediated by acetylcholine-induced activation of M3 receptors, which couple to the heterotrimeric G protein Gq/11, resulting in stimulation of phospholipase C and an increase in intracellular calcium. M3 receptors are also possibly found on endothelial cells 105 and vascular smooth muscle 145. M2 receptors are also found on airway smooth muscle and submucosal glands. However, M2 activation by acetylcholine does not cause smooth muscle contraction, but instead antagonizes smooth muscle relaxation that is induced by beta-adrenoceptors (see below). Thus, activation of M2 receptors inhibits the generation and accumulation of cyclic adenosine monophosphate (cAMP), thereby preventing bronchodilation. Other mechanisms may also modulate the contraction of the smooth muscle cells. For example, histamine that is released from activated mast cells may also cause bronchoconstriction. This is because H1-receptors are located in human bronchial muscle and are linked to transduction systems that cause increased intracellular Ca2+, which leads to muscle contraction.

The M2 receptors also play a significant role in the endings of the nerve fibers that transmit acetylcholine across the neuromuscular junction. M2 receptors in those fibers self-limit the transmission of acetylcholine, i.e., some of the transmitted acetylcholine activates those M2 receptors so as to then inhibit that same transmission. When this feedback inhibition becomes dysfunctional, excessive acetylcholine is transmitted to the smooth muscle, leading to hyper-responsiveness to allergens and excessive bronchoconstriction. Allergen-induced M2 receptor dysfunction is dependent upon selective recruitment of eosinophils to the airway nerves. Activated eosinophils release major basic protein, which binds to M2 receptors and prevents binding of acetylcholine. The binding of a virus may also affect the structure of the M2 receptor itself, or viruses may act via activation of inflammatory cells, in particular macrophages and T lymphocytes, leading to similar changes in receptor function that bring about similar dysfunction [FRYER A D and Jacoby D B. Muscarinic receptors and control of airway smooth muscle. Am J Respir Crit Care Med 158 (5, Pt 3, 1998):S154-60; BELMONTE K E. Cholinergic pathways in the lungs and anticholinergic therapy for chronic obstructive pulmonary disease. Proc Am Thorac Soc 2 (4, 2005):297-304].

Noncholinergic parasympathetic nerves also innervate the airways. Noncholinergic parasympathetic transmitters are not co-released with acetylcholine from a single population of postganglionic parasympathetic nerves. Instead, an anatomically and functionally distinct parasympathetic pathway regulates nonadrenergic, noncholinergic relaxations of airway smooth muscle. The preganglionic nerves innervating airway noncholinergic, parasympathetic ganglia may be unmyelinated and may originate from a distinct location in nucleus ambiguus or may be derived from the dorsal motor nuclei of the vagus nerves (See FIG. 1). Unlike cholinergic contractions of the airway smooth muscle, which can reach a near maximum within about 30 seconds and can nearly completely reverse at the same rate, noncholinergic parasympathetic nerve-mediated relaxations are both slow in onset and reversal, requiring several minutes to reach equilibrium.

Noncholinergic parasympathetic neurotransmitters include the vasoactive intestinal peptide (VIP), the peptide pituitary adenylate cyclase-activating peptide (PACAP), peptide histidine-isoleucine, peptide histidine-methionine, and nitric oxide (NO). Fibers with those neurotramsmitters are primarily under parasympathetic control, although sympathetic nerves in the airways have also been shown to include such fibers [MATSUMOTO K, Aizawa H, Takata S, Inoue H, Takahashi N, Hara N. Nitric oxide derived from sympathetic nerves regulates airway responsiveness to histamine in guinea pigs. J Appl Physiol 83 (5, 1997):1432-1437]. Both VIP and NO synthase have been localized to nerve fibers innervating airway smooth muscle and to parasympathetic ganglia in the airways. Because such non-adrenergic, noncholinergic nerve fibers inhibit activities such as smooth muscle contraction, they are known as iNANC fibers. Excitatory non-adrenergic, non-cholinergic (eNANC) nerve fibers also exist. Responses to those fibers are mediated by the release of tachykinins such as substance P. In the presence of muscarinic blockade, vagal stimulation causes dilatation of preconstricted airways via noncholinergic neurotransmitters, demonstrating the dominance or overabundance of iNANC fibers relative to eNANC fibers.

It should be noted that a number of nonbronchiolar afferent nerve subtypes may also induce a withdrawal of cholinergic tone, including baroreceptors, skeletal muscle and diaphragmatic afferents, and pulmonary stretch receptors, some of which are also conveyed by the vagus nerve. These disparate afferent inputs may be simultaneously recruited, for example, during exercise. It should also be noted that although FIG. 1 shows a reflex loop involving afferent and efferent nerve fibers sending signals from and to a single bronchiole, in reality signals from the afferent fibers emanating from one bronchiole may result in efferent signals that are sent to another bronchiole. This is particularly important as it relates to the cooperative behavior of smooth muscle throughout the airways, as described later in connection with avalanches of bronchoconstriction and bronchodilation.

Turning now to control of the airways by the sympathetic nervous system, it is known that some sympathetic pulmonary afferent nerves exist. However, unlike the well-characterized parasympathetic afferent nerve fibers described above, the sympathetic afferent fibers have been described only as capsaicin-sensitive, substance P-containing spinal afferent neurons in the upper thoracic (T1-T4) dorsal root ganglia (DRG) that innervate the airways and lung [KOSTREVA D R, Zuperku E J, Hess G L, Coon R L, Kampine J P. Pulmonary afferent activity recorded from sympathetic nerves. J Appl Physiol 39 (1, 1975):37-40; Eun Joo O H, Stuart B. Mazzone, Brendan J. Canning and Daniel Weinreich. Reflex regulation of airway sympathetic nerves in guinea-pigs. J Physiol 573 (2, 2006): 549-564].

With regard to the efferent sympathetic nerves, human airway smooth muscle is largely devoid of sympathetic adrenergic efferent innervation (in contrast to some other mammals), with relatively few fibers reaching the level of secondary bronchi and terminal bronchioles. Nevertheless, some sympathetic fibers do innervate the glands, vasculature, and parasympathetic ganglia of the human bronchial tree. Furthermore, recent evidence has suggested asthma patients do have such sympathetic innervations within the bronchial smooth muscle. Alpha-adrenergic receptors are localized on pulmonary and bronchial blood vessels, bronchial epithelial cells, submucosal glands, in parasympathetic ganglia, and on cholinergic and C afferent nerve fibers, where limited sympathetic innervation may occur. Beta-adrenergic receptors are numerous on airway smooth muscle, despite a lack of significant sympathetic innervation there, the significance of which is that beta-adrenergic control may be via circulating catecholamines rather than by the release of neurotransmitters from local nerve fibers.

In fact, the most significant parts of the sympathetic nervous system in regards to control of the airways may be within the parasympathetic ganglia and in the adrenal medulla. Postganglionic sympathetic nerve fibers intermingle with cholinergic nerves in parasympathetic ganglia, where sympathetic fibers may modulate cholinergic neurotransmission [Allen C MYERS. Transmission in autonomic ganglia. Respiration Physiology 125 (1-2, 2001): 99-111;

BAKER, D. G., Basbaum, C. B., Herbert, D. A., Mitchell, R. A. Transmission in airway ganglia of ferrets: Inhibition by norepinephrine. Neurosci. Lett. 41(1983):139-43; Richardson J and Beland J. Nonadrenergic inhibitory nervous system in human airways. J Appl Physiol 41: 764-771, 1976]. FIG. 1 shows fibers emanating from sympathetic ganglia that impinge upon the parasympathetic ganglia. Some of those fibers may terminate in the parasympathetic ganglia to modulate the parasympathetic fibers that reach the bronchi, and a small number of the sympathetic fibers may actually pass through or near the parasympathetic ganglia to reach the bronchi.

Epinephrine acts as a circulating hormone to participate in the regulation of bronchomotor tone through the stimulation of beta-2 receptors. Beta-adrenergic receptors are numerous on airway smooth muscle, and their stimulation by circulating catecholamines produces bronchodilatation. Epinephrine is derived mostly from the adrenal medulla, which is under the control of the sympathetic nervous system (See FIG. 1). The cells of the adrenal medulla are innervated directly by fibers from intermediolateral nucleus (IML, in the thoracic spinal cord from T5-T11). Because it is innervated by preganglionic nerve fibers, the adrenal medulla can be considered to be a specialized sympathetic ganglion. It is ordinarily only during strenuous exercise that epinephrine concentrations are raised sufficiently to cause significant bronchodilation, e.g., to counteract bronchospasm that is induced by exercise in asthma [BERKIN K E, Inglis G C, Ball S G, et al. Airway responses to low concentrations of adrenaline and noradrenaline in normal subjects. Q J Exp Physiol 70 (1985):203-209; Neil C THOMSON, Kenneth D Dagg, Scott G Ramsay. Humoral control of airway tone. Thorax 51(1996):461-464]. Repeated stimulation of some vagus nerve fibers may cause the repeated pulsatile systemic release of epinephrine (and/or other catecholamies), leading eventually to circulating steady state concentrations of catecholamines that are determined by the stimulation frequency as well as the half-life of circulating catecholamines.

The preceding paragraphs describe the efferent and afferent nerve fibers that respectively send signals to and from the bronchi and bronchioles. The paragraphs that follow describe the processing of the afferent sensory signals within the central nervous system to produce the efferent controlling signals (see FIG. 1). The neurons of this central respiratory network drive two functionally and anatomically distinct pools of motoneurons. Both groups have to be precisely coordinated to ensure efficient ventilation. One set, located within the spinal cord, innervates the diaphragm and intercostal muscles that force air into the lungs. A second group of motoneurons, with which this discussion is primarily concerned, is located within the nucleus ambiguus and to a lesser extent within the dorsal motor nucleus of the vagus. The latter group projects via the vagus nerve to coordinate the activity of laryngeal and bronchial muscle so as to control airway resistance and airflow.

The relevant interconnected centers shown in FIG. 1 are located in the medulla (nucleus tractus solitarius, nucleus ambiguus and dorsal motor nucleus of the vagus, rostral ventral lateral medulla, rostral ventral medial medulla, medullary raphe nuclei), the pons/midbrain (periaqueducatal gray, locus ceruleus, raphe nuclei—e.g. dorsal), the diencephalon (hypothalamic nuclei, particularly the paraventricular nucleus of the hypothalamus), and the telencephalon (amygdala and its connections to the brain cortex). These same centers are involved more generally in the integration of cardiopulmonary functions and the regulation of body fluids (e.g., baroreflex and pH or CO2 chemoreception reflexes) [David JORDAN. Central nervous pathways and control of the airways. Respiration Physiology 125(2001): 67-81; Leszek KUBIN, George F. Alheid, Edward J. Zuperku, and Donald R. McCrimmon. Central pathways of pulmonary and lower airway vagal afferents. J Appl Physiol 101(2006): 618-627; Musa A. HAXHIU, Prabha Kc, Constance T. Moore, Sandra S. Acquah, Christopher G. Wilson, Syed I. Zaidi, V. John Massari, and Donald G. Ferguson. Brain stem excitatory and inhibitory signaling pathways regulating bronchoconstrictive responses. J Appl Physiol 98(2005): 1961-1982; K C P, Martin R J. Role of central neurotransmission and chemoreception on airway control. Respir Physiol Neurobiol 173 (3, 2010):213-22; Bradley J. UNDEM and Carl Potenzieri. Autonomic Neural Control of Intrathoracic Airways. Comprehensive Physiology 2(2012):1241-1267; R. A. L. DAMPNEY. Functional organization of central pathways regulating the cardiovascular system. Physiological Reviews 74:323-364].

Consider first the input to the central pathways. Vagal afferents traverse the brainstem in the solitary tract, with some eighty percent of the terminating synapses being located in the nucleus of the tractus solitarius (NTS). The NTS projects to a wide variety of structures, as shown in FIG. 1, including the amygdala, raphe nuclei, periaqueductal gray, nucleus ambiguus and the hypothalamus. The NTS also projects to the parabrachial nucleus, which in turn projects to the hypothalamus, the thalamus, the amygdala, the anterior insular, and infralimbic cortex, lateral prefrontal cortex, and other cortical regions. [JEAN A. The nucleus tractus solitarius: neuroanatomic, neurochemical and functional aspects. Arch Int Physiol Biochim Biophys 99 (5, 1991):A3-A52].

A subset of NTS neurons receiving afferent input from SARs (termed pump or P-cells) mediates the Breuer-Hering reflexes and inhibits neurons receiving afferent input from RARs. Those reflexes are related to the control of spontaneous breathing rate and depth, especially in children and exercising adults, and they are also related to respiratory sinus arrhythmia, in which the heart rate is modulated by the respiratory rate and depth.

P-cells and second order neurons in the RAR pathway provide inputs to regions of the ventrolateral medulla involved in control of respiratory motor pattern. The core circuit components that constitute the neural machinery for generating respiratory rhythm and shaping inspiratory and expiratory motor patterns are distributed among three adjacent structural compartments in the ventrolateral medulla: the Bötzinger complex, pre-Bötzinger complex and rostral ventral respiratory group.

Axon collaterals from both P-cells and RAR interneurons, and likely from NTS interneurons in the C-fiber pathway, project to the parabrachial pontine region where they may contribute to plasticity in respiratory control, as well as integration of respiratory control with other systems, including those that provide for voluntary control of breathing, sleep-wake behavior, and emotions.

Consider now the output from the central pathways. Airway-related vagal preganglionic neurons (AVPNs) are the final common pathway from the central nervous system to the airways and transmit signals to the intrinsic bronchial ganglia that are part of the network for automatic feedback control. In most mammals, the motor preganglionic component of the network innervating the airways arises mainly from the nucleus ambiguus and to a lesser extent from the dorsal motor nucleus of the vagus (DMV). Of these two groups of neurons, AVPNs within the rostral nucleus ambiguus play a greater role in generating cholinergic outflow to airway smooth muscle.

Acetylcholine release at the bronchial smooth muscle is triggered by the activation of AVPNs, resulting in bronchoconstriction. Such activation of AVPNs is typically triggered by vagal C fibers via the activation of the NTS, wherein glutamate is released into the AVPNs. This C fiber activation may be in response to irritants, allergens, trauma, or idiopathic mechanisms associated with hypersensitivity. The activation may also be via A-delta fibers whose cell bodies reside in the jugular ganglia, which (like the C fibers) resemble the nociceptive fibers of the somatosensory system in that they have relatively high thresholds to mechanical stimuli and respond to classic nociceptive fiber-selective stimuli such as capsaicin and bradykinin [Michael J. CARR and Bradley J. Undem. Bronchopulmonary afferent nerves. Respirology 8(2003):291-301].

Thus, the simplest feedback loop shown in FIG. 1 is one in which signals from afferent fibers to the NTS result in subsequent direct activation of the AVPNs by the NTS, resulting in a level of broncho-constriction that is a function of the magnitude of the C or jugular A-delta fiber activation. It is understood that this level of constriction is largely a balance between the effects of cholinergic stimulation, iNANC relaxation, and relaxation due to circulating catecholamines. Mechanistically, the preganglionic nerves innervating airway noncholinergic, parasympathetic ganglia may originate from a distinct location in nucleus ambiguus or may be derived from the dorsal motor nuclei of the vagus nerves (dmnX).

However, AVPNs receive connections from multiple sites within the brain, not just the NTS, and these additional connections may inhibit glutamate-mediated activation of the AVPNs. Such additional connections have been demonstrated by retrograde transneuronal labeling with pseudorabies virus in C8 cord-transected rats. They include connections of the AVPNs to the amygdala, hypothalamus, periaqueductal grey matter of the midbrain (PAG), locus ceruleus, and raphe nuclei (see FIG. 1) [HADZIEFENDIC S, Haxhiu M A. CNS innervation of vagal preganglionic neurons controlling peripheral airways: a transneuronal labeling study using pseudorabies virus. J Auton Nervous Syst. 76 (2-3, 1999):135-145; HAXHIU M A, Jansen A S P, Cherniack N S, Loewy A D. CNS innervation of airway-related parasympathetic preganglionic neurons: a transneuronal labeling study using pseudorabies virus. Brain Res 618 (1, 1993):115-134].

Thus, the response of the AVPNs to excitatory inputs also depends on the inhibitory inflow to the AVPNs. Many inhibitory cell groups projecting to the AVPNs are linked to the hypothalamus, and a function of those projections is related in part to the control of respiration during sleep, maintenance of attention, motivation, and arousal states [Musa A. HAXHIU, Serdia O. Mack, Christopher G. Wilson, Pingfu Feng, and Kingman P. Strohl. Sleep networks and the anatomic and physiologic connections with respiratory control. Frontiers in Bioscience 8 (2003): d946-962]. When activated, GABA- and galaninergic cells inhibit histamine-containing neurons of the tuberomamillary nucleus (TMN) and the orexin-producing cells of the lateral hypothalamic area (LHA). This inhibition causes withdrawal of excitatory inputs from TMN and LHA neurons to serotonin (5-HT) expressing cells of raphe nuclei (RN) and the locus coeruleus (LC) norepinephrine-synthesizing cells. In addition, activation of neurons within the ventrolateral preoptic area directly inhibits LC and RN neurons, as well as GABA-containing cells of the ventrolateral periaqueductal gray (PAG), which project to AVPNs. Stimulation of the LC noradrenergic cell group and activation of parabrachial nucleus is known induce centrally mediated airway smooth muscle relaxation [Michele BAROFFIO, Giovanni Barisione, Emanuele Crimi and Vito Brusasco. Noninflammatory mechanisms of airway hyper-responsiveness in bronchial asthma: an overview. Ther Adv Respir Dis 3 (4, 2009): 163-174; Musa A. HAXHIU, Bryan K. Yamamoto, Ismail A. Dreshaj and Donald G. Ferguson. Activation of the midbrain periaqueductal gray induces airway smooth muscle relaxation. J Appl Physiol 93 (2002):440-449; HAXHIU, Musa A., Prabha Kc, Burim Neziri, Bryan K. Yamamoto, Donald G. Ferguson, and V. John Massari. Catecholaminergic microcircuitry controlling the output of airway-related vagal preganglionic neurons. J Appl Physiol 94 (2003): 1999-2009]. Such inhibitory mechanisms may be dysfunctional in patients with airway disease such as asthma [Christopher G. WILSON, Shamima Akhter, Catherine A. Mayer, Prabha Kc, Kannan V. Balan, Paul Ernsberger, and Musa A. Haxhiu. Allergic lung inflammation affects central noradrenergic control of cholinergic outflow to the airways in ferrets. J Appl Physiol 103(2007): 2095-2104].

Thus, acting in opposition to glutamate-mediated (and possibly substance P) activation of the AVPNs by the NTS are GABA, and/or serotonin, and/or norepinephrine from the periaqueductal gray, raphe nuclei, and locus coeruleus, respectively. As shown in FIG. 1, control of the inhibitory influence by the PAC, LC, and RN on the AVPNs may be exerted directly at sites within the nucleus ambiguus or dorsal motor nucleus. The inhibitory influence may also be on the nucleus tractus solitarius (NTS), which is connected bidirectionally to these centers. Thus, the inhibition may decrease the activation of the AVPNs by the NTS rather than simply inhibiting an already-existing activation of the AVPNs by the NTS. Alternatively, the inhibitory influence on the NTS may occur indirectly via the hypothalamus owing to bidirectional connections between the NTS and hypothalamus.

The activation of inhibitory circuits in the periaqueductal gray, raphe nucei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 1 [PUDOVKINA O L, Cremers T I, Westerink B H. The interaction between the locus coeruleus and dorsal raphe nucleus studied with dual-probe microdialysis. Eur J Pharmacol 7(2002); 445 (1-2):37-42; REICHLING D B, Basbaum A I. Collateralization of periaqueductal gray neurons to forebrain or diencephalon and to the medullary nucleus raphe magnus in the rat. Neuroscience 42 (1, 1991): 183-200; BEHBEHANI M M. The role of acetylcholine in the function of the nucleus raphe magnus and in the interaction of this nucleus with the periaqueductal gray. Brain Res 252 (2, 1982):299-307; de Souza MORENO V, Bícego K C, Szawka R E, Anselmo-Franci J A, Gargaglioni L H. Serotonergic mechanisms on breathing modulation in the rat locus coeruleus. Pflugers Arch 459 (3, 2010):357-68].

Another structure also has a significant influence on AVPN activity, namely, the amygdala. The prefrontal cortex innervates the amygdala, which projects to multiple targets regulating autonomic functions, including the PAG, the NTS, and the nucleus ambiguus. Projections from the amygdala to the PAG are significant because the PAG neurons coordinate functions of multiple visceral organs involved in responses to stress, including those involving the airway. The effects of amygdala activity transmitted via the PAG to the AVPNs may be inhibitory or stimulatory, depending upon whether the patient is experiencing active or passive coping responses. As shown in FIG. 1, such control of AVPN activity via the amygdala may be modulated by connections to the NTS, either directly or via the hypothalamus.

Finally, consider central modulation of the airways via the sympathetic nervous system. Only a limited number of discrete regions within the supraspinal central nervous system project to sympathetic preganglionic neurons in the intermediolateral column (see FIG. 1). The most important of these regions are the rostral ventral lateral medulla (RVLM), the rostral ventromedial medulla (RVMM), the midline raphe, the paraventricular nucleus (PVN) of the hypothalamus, the medullocervical caudal pressor area (mCPA), and the A5 cell group of the pons. The first four of these connections to the intermediolateral nucleus are shown in FIG. 1 [STRACK A M, Sawyer W B, Hughes J H, Platt K B, Loewy A D. A general pattern of CNS innervation of the sympathetic outflow demonstrated by transneuronal pseudorabies viral infections. Brain Res. 491 (1, 1989): 156-162].

The rostral ventral lateral medulla (RVLM) is the primary regulator of the sympathetic nervous system, sending excitatory fibers (glutamatergic) to the sympathetic preganglionic neurons located in the intermediolateral nucleus of the spinal cord. Afferents affecting cardiopulmonary function synapse in the NTS, and their projections reach the RVLM via the caudal ventrolateral medulla. However, resting sympathetic tone also comes from sources above the pons, from hypothalamic nuclei, various hindbrain and midbrain structures, as well as the forebrain and cerebellum, which synapse in the RVLM. Only the hypothalamic projection to the RVLM is shown in FIG. 1 [K C P, Dick T E. Modulation of cardiorespiratory function mediated by the paraventricular nucleus. Respir Physiol Neurobiol 174 (1-2, 2010): 55-64].

The RVLM shares its role as a primary regulator of the sympathetic nervous system with the rostral ventromedial medulla (RVMM) and medullary raphe. Differences in function between the RVLM versus RVMM/medullary raphe have been elucidated in the case of cardiovascular control. In that case, barosensitive sympathetic efferents appear to be regulated primarily through the RVLM, whereas the cutaneous circulation is regulated predominantly through the RVMM and medullary raphe. In the case of respiratory control, less is known, although it is thought that nociceptive sympathetic efferents are regulated through the RVMM and serotonin-containing medullary raphe. Differential control of the RVLM by the hypothalamus may also occur via circulating hormones such as vasopressin. The RVMM contains at least three populations of nitric oxide synthase neurons that send axons to innervate functionally similar sites in the NTS and nucleus ambiguus. Circuits connecting the RVMM and RVLM may be secondary, via the NTS and hypothalamus [Paul M. PILOWSKY, Mandy S. Y. Lung, Darko Spirovski and Simon McMullan. Differential regulation of the central neural cardiorespiratory system by metabotropic neurotransmitters. Phil. Trans. R. Soc. B 364(2009): 2537-2552].

FIG. 1 shows the afferent and efferent limbs of neural control to a single bronchiole, in which afferent signals from a bronchiole result in efferent controlling signals to that same bronchiole. The figure does not show how afferent signals originating from one bronchiole generate efferent signals to other bronchioles, which may be at the same or different levels of bronchial bifurcation. If the smooth muscle in all bronchia and bronchioles were to constrict and dilate in unison, then the depiction in FIG. 1 would reflect the circuitry of the lung as a whole. However, individual normal bronchioles actually undergo constant constriction and dilation, such that the diameters of their lumens may vary considerably over the course of even a few minutes. Normally, some bronchioles are constricting while others are dilating, but the time-varying heterogeneity of airway caliber throughout the lung is normally sufficient to bring air to all the alveoli, because any constricted bronchiole would reopen in a relatively short period of time. This oscillation of constriction and dilation of individual bronchioles throughout the lung leads to physiological fluctuations in airway resistance at the level of the whole lung [QUE C L, Kenyon C M, Olivenstein R, Macklem P T, Maksym G N. Homeokinesis and short-term variability of human airway caliber. J Appl Physiol 91 (3, 2001):1131-

41; MUSKULUS M, Slats A M, Sterk P J, Verduyn-Lunel S. Fluctuations and determinism of respiratory impedance in asthma and chronic obstructive pulmonary disease. J Appl Physiol 109 (6, 2010):1582-91; FREY U, Maksym G, Suki B. Temporal complexity in clinical manifestations of lung disease. J Appl Physiol 110 (6, 2011):1723-31].

Accordingly, the present invention considers bronchiole segments to be oscillators, in which a mathematical variable corresponding to each bronchiole segment represents the time-varying radius of a bronchiole lumen, relative to a value representing a time-averaged radius of that bronchiole. Because segments of the bronchial tree are fluctuating according to the invention, the oscillating branches collectively give rise to fluctuations in overall respiratory impedance. It is thought that an asthma attack (or other bronchoconstrictive exacerbation) may correspond to an avalanche of airway constrictions, in which the constriction in one bronchiole segment increases the likelihood that another bronchiole branch in the same tree structure of the lung will constrict. The mechanisms linking one bronchiole segment to another include: the shared airflow in the lumens that connect one bronchiole to another; and neural connections to multiple bronchioles. As a result of the interconnected bronchiole fluctuations, some initial heterogeneity of airway constriction within different regions of the lung, which might seem to be of little physiological consequence, may actually become amplified by avalanches of airway constrictions, such that eventually large heterogeneous regions of the lung become unavailable for normal respiration.

Models have been constructed to explain such heterogeneity and avalanches (of closure and of reopening), but they have been used only to assess the risk of an asthma attack, rather than to explain or predict the actual occurrence of an asthma attack. A model of lung dynamics that is disclosed towards the end of this application is intended to make such a prediction for use in a feedforward controller. It does so by making oscillation of any one bronchiole oscillator be a function of the state of other bronchiole oscillators, as well as a function of external conditions such as the presence of inhaled irritants and the accumulated effects of electrical stimulation of a vagus nerve. In one aspect of the present invention, the stimulation of a vagus nerve randomizes (e.g., through the quasi-random stimulation of individual fibers within the vagus nerve) afferent neural signals sent to the central nervous system, thereby resetting the phase relations between bronchiole oscillators, and consequently allowing for an avalanche-type reopening of bronchioles within regions of the lung that had been poorly ventilated, or for an inhibition of an avalanche-type bronchiolar closing. Quasi-random stimulation of efferent fibers by VNS may also be involved in such avalanche-type reopening [ALENCAR A M, Arold S P, Buldyrev S V, Majumdar A, Stamenovic D, Stanley H E, Suki B. Physiology: Dynamic instabilities in the inflating lung. Nature 417 (6891, 2002):809-11; SUKI B, Frey U. Temporal dynamics of recurrent airway symptoms and cellular random walk. J Appl Physiol 95 (5, 2003):2122-7; VENEGAS J G, Winkler T, Musch G, Vidal Melo M F, Layfield D, Tgavalekos N, Fischman A J, Callahan R J, Bellani G, Harris R S. Self-organized patchiness in asthma as a prelude to catastrophic shifts. Nature 434 (7034, 2005):777-82; FREY U, Brodbeck T, Majumdar A, Taylor D R, Town G I, Silverman M, Suki B. Risk of severe asthma episodes predicted from fluctuation analysis of airway function. Nature 438 (7068, 2005):667-70; FREY U. Predicting asthma control and exacerbations: chronic asthma as a complex dynamic model. Curr Opin Allergy Clin Immunol 7 (3, 2007):223-30; MULLALLY W, Betke M, Albert M, Lutchen K. Explaining clustered ventilation defects via a minimal number of airway closure locations. Ann Biomed Eng 37 (2, 2009):286-300; POLITI A Z, Donovan G M, Tawhai M H, Sanderson M J, Lauzon A M, Bates J H, Sneyd J. A multi-scale, spatially distributed model of asthmatic airway hyper-responsiveness. J Theor Biol 266 (4, 2010):614-24; TAWHAI M H, Bates J H. Multi-scale lung modeling. J Appl Physiol 110 (5, 2011):1466-72; SUKI B, Bates J H. Emergent behavior in lung structure and function. J Appl Physiol 110 (4, 2011):1109-10; KACZKA D W, Lutchen K R, Hantos Z. Emergent behavior of regional heterogeneity in the lung and its effects on respiratory impedance. J Appl Physiol 110 (5, 2011):1473-81].

FIG. 1 also shows a vagus nerve being electrically stimulated according to the present invention, which in general would modulate the activity of both afferent and efferent vagal nerve fibers. The particular structures within the patient that will be affected by the stimulation depend upon the details of the stimulation protocol. As described below, depending on whether the stimulation voltage is high or low, the stimulation may either constrict or dilate bronchial smooth muscle. As taught below in this disclosure, particular electrical stimulation waveforms bring about the dilation of constricted bronchi and bronchioles and also produce a minimum of unwanted side effects. The absence or minimization of unwanted side effects is also made possible by the use of noninvasive electrical stimulation devices that are disclosed herein, which shape the electrical stimulation in such a way as avoid the stimulation of tissue near the vagus nerve that would cause pain, unwanted muscle twitching, or other unwanted non-selective effects. Thus, the method of vagal nerve stimulation that is disclosed below uses parameters (intensity, pulse-width, frequency, duty cycle, etc.) that selectively activate certain structures shown in FIG. 1. The stimulation waveform parameters are different from those used to treat other diseases with vagus nerve stimulation, such as epilepsy [Jeong-Ho CHAE, Ziad Nahas, Mikhail Lomarev, Stewart Denslow, Jeffrey P. Lorberbaum, Daryl E. Bohning, Mark S. George. A review of functional neuroimaging studies of vagus nerve stimulation (VNS). Journal of Psychiatric Research 37 (2003) 443-455; G. C. Albert, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009): 1042-1060].

Mention was made above of a phase-resetting mechanism, wherein stimulation of the vagus nerve blocks a bronchial-closing avalanche or promotes a re-opening bronchial avalanche. In view of the foregoing discussion of ways in which the vagus nerve can affect the bronchi, a large number of additional physiological mechanisms can be envisaged, many of which are not mutually exclusive. Depending on the details of the stimulation waveform and stimulation devices, the vagal nerve stimulation may stimulate, block, or otherwise modulate particular types of nerve fibers within the vagus nerve (e.g., afferent vs. efferent, nerve fiber types A, B, and/or C, parasympathetic or sympathetic, etc.). The stimulation may generate action potentials that propagate in orthodromal or in antidromal directions. More particular mechanisms may also be envisaged. For example, parasympathetic efferent cholinergic fibers could be blocked directly, thereby inhibiting bronchoconstriction. Such inhibition could involve muscarinic receptors M2 or M3 or both. As another example, the VNS could result in the stimulation of efferent iNANC nerve fibers that promote bronchodilation. Alternatively, small numbers of sympathetic efferent fibers could directly cause relaxation of bronchial smooth muscle, or fibers from sympathetic ganglia could stimulate parasympathetic ganglia, thereby indirectly stimulating iNANC fibers to cause relaxation of bronchial smooth muscle. Alternatively, fibers from sympathetic ganglia could inhibit parasympathetic ganglia, thereby inhibiting parasympathetic cholinergic fibers from constricting smooth muscle. Alternatively, norepinephrine outflow from the sympathetic-innervated pulmonary vasculature could promote bronchodilation, or fibers from the interomediolateral nucleus could stimulate the adrenal gland, producing circulating epinephrine that relaxes bronchial smooth muscle. Furthermore, stimulation of the vagus nerve could directly inhibit the activation of the AVPNs by the nucleus tractus solitarius (NTS). Alternatively, the inhibitory influence on the NTS may occur indirectly via activation of the hypothalamus, and/or amygdala and/or periaqueductal gray and/or locus coeruleus and/or raphe nuclei. Alternatively, the inhibition may be the combined result of inhibitory and excitatory influences within the AVPNs (the + and − influences shown in FIG. 1). According to this aspect of the invention, noninvasive VNS with the disclosed devices activates pathways causing release of norepinephrine, serotonin and/or GABA (inhibitory neurotransmitters) onto the AVPNs, thereby preventing or reducing the release of acetylcholine in the airways and resulting in bronchorelaxation. According to this view, noninvasive VNS acts as a central, specific, airway anticholinergic, but without any of the side effects of systemic anticholinergic therapy. In addition, these same inhibitory neurotransmitters act on the mucous glands throughout the airway passages in the nose, mouth, throat and lungs of the patient. Therefore, the noninvasive VNS taught by the present invention also serves to inhibit mucous production in these airway passages, resulting in increased airflow throughout these passages. Thus, the present invention can provide a dual benefit: (1) an immediate reduction in acetylcholine release to the lungs, providing an immediate (within minutes or seconds) bronchodilation effect for the patient; and (2) a decrease in mucous production which provides a more gradual improvement of airflow to the patient. After providing a description of Applicant's nerve stimulating devices and methods, the present disclosure will describe animal experiments that test some of these potential mechanisms.

Description of Applicant's Magnetic and Electrode-Based Nerve Stimulating/Modulating Devices, Describing in Particular the Electrical Waveform that is Used to Stimulate a Vagus Nerve.

Figure 2A:
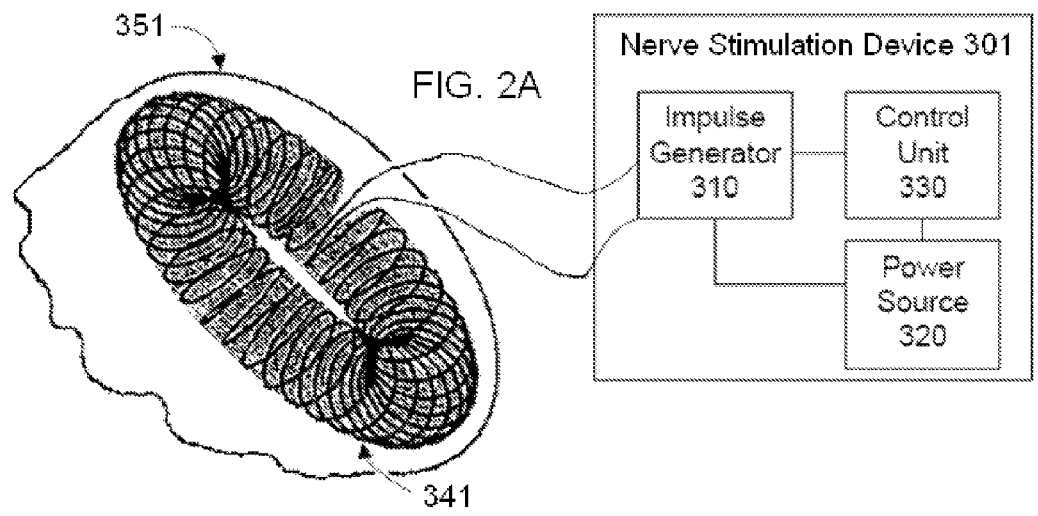
FIGS. 2A-2E show a schematic view of nerve modulating devices according to the present invention, which supply controlled pulses of electrical current to a magnetic stimulator coil (FIG. 2A) or to surface electrodes (FIG. 2B), and the figure also shows (FIGS. 2C, 2D, 2E) an exemplary electrical voltage/current profile and waveform for stimulating, blocking and/or modulating impulses that are applied to a nerve.

FIG. 2A is a schematic diagram of Applicant's magnetic nerve stimulating/modulating device 301 for delivering impulses of energy to nerves for the treatment of medical conditions, particularly treatment of broncho-constriction. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 2A to be a single coil, in practice the coil may also comprise two or more distinct coils, each of which is connected in series or in parallel to the impulse generator 310. Thus, the coil 341 that is shown in FIG. 2A represents all the magnetic stimulator coils of the device collectively. In a preferred embodiment that is discussed below, coil 341 actually contains two coils that may be connected either in series or in parallel to the impulse generator 310.

The item labeled in FIG. 2A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below, the conducting medium with which the coil 341 is in contact need not completely surround the toroid.

The design of the magnetic stimulator 301, which is also adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

Figure 2B:
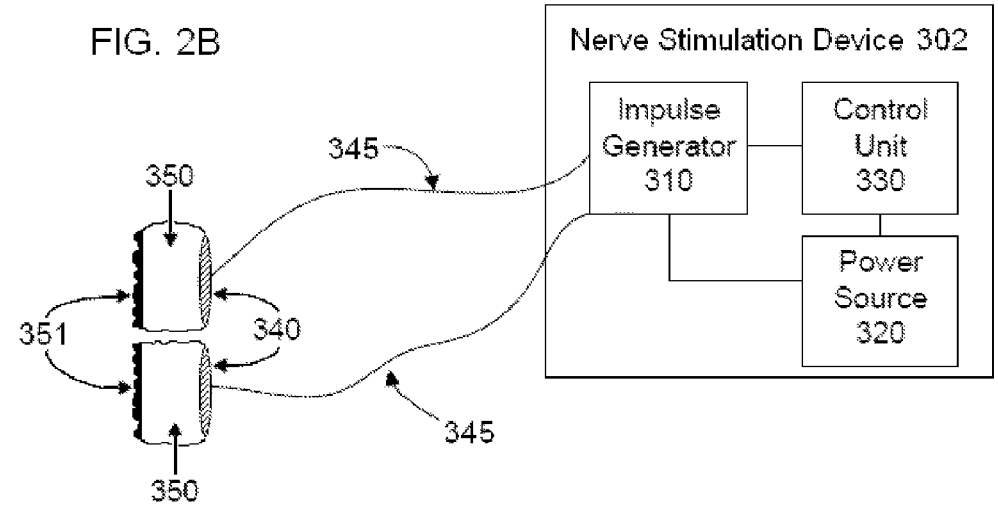

An alternate embodiment of the present invention is shown in FIG. 2B, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 2B, in practice the electrodes may also comprise three or more distinct electrode elements, each of which is connected in series or in parallel to the impulse generator 310. Thus, the electrodes 340 that are shown in FIG. 2B represent all electrodes of the device collectively.

The item labeled in FIG. 2B as 350 is a volume, contiguous with an electrode 340, that is filled with electrically conducting medium. As described below in connection with particular embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals (see FIG. 15), analog-to-digital converters for digitizing externally supplied analog signals (see FIG. 15), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurło, Przemysław Płonecki, Jacek Starzyński, Stanisław Wincenciak, Andrzej Rysz. Mathematical Modeling of Vagus Nerve Stimulation. pp. 92-97 in: Krawczyk, A. Electromagnetic Field, Health and Environment: Proceedings of EHE '07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 2C:
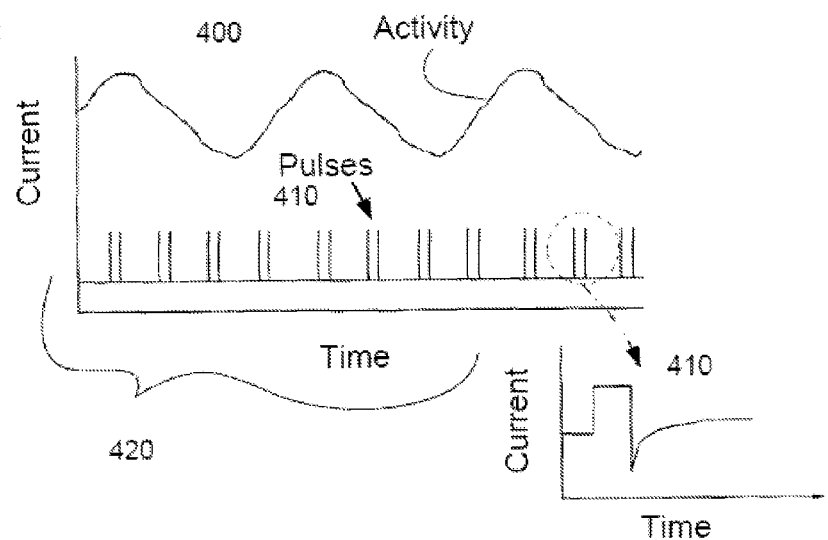

FIG. 2C illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 1 microseconds to about 1000 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51 (5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2D:
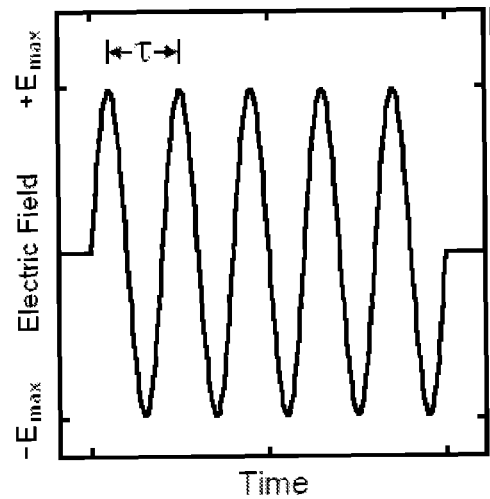
Figure 2E:
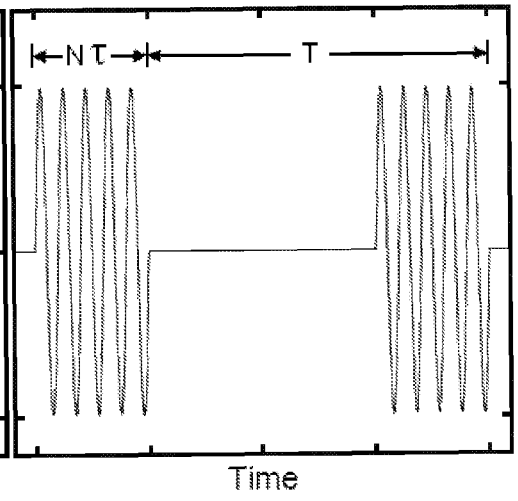

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2D and 2E. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2E to make the bursts discernable). When these exemplary values are used for T and $\tau$, the waveform contains significant Fourier components at higher frequencies (1/200 microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009): 181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No.

4,177,819, entitled Muscle stimulating apparatus, to KOF-SKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2D and 2E may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011].

Those methods involve high-frequency modulation in the range of from about 1.5 KHz to about 50 KHz, which is applied to the patient's spinal cord region. However, such methods are different from the present invention because, for example, they are invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2(2000):477-509].

Figure 15:
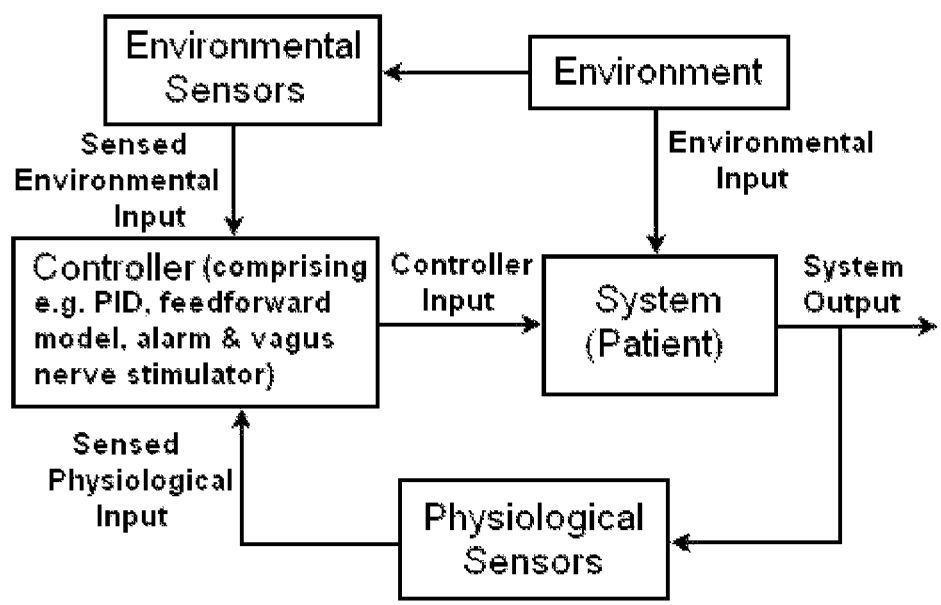
FIG. 15 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 15). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance. In normal respiratory physiology, sighing at irregular intervals is thought to bring about such a resetting of the respiratory control system. Experimentally, noisy artificial ventilation may increase respiration [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis to create in the patient a lower reactivity of the nerve.

Applicant's Animal Experiments Demonstrating that the Disclosed Stimulation Waveform and Devices Bring about Bronchodilation by Particular Physiological Mechanisms Applicant performed animal experiments using invasive methods in an attempt to (1) demonstrate that it is in fact possible to stimulate the vagus nerve to produce bronchodilation without first producing bronchoconstriction, and (2) elucidate physiological mechanisms that may explain such bronchodilation. Such animal experiments were then performed using noninvasive vagus nerve stimulation, as now described.

Of Histamine-Induced Bronchoconstriction in Guinea Pig and Swine by Pulsed Electrical Vagal Nerve Stimulation A first set of experiments was performed to determine whether applying a low-voltage electrical signal to the vagus nerve could reduce histamine-induced bronchoconstriction in swine and guinea pigs. Sixteen guinea pigs were anesthetized and had bipolar electrodes positioned on the cervical vagus nerves. Intravenous histamine was titrated to elicit a moderate increase in pulmonary inflation pressure (Ppi). Histamine was then administered with or without concurrent vagus nerve stimulation (VNS).

Figure 3A:
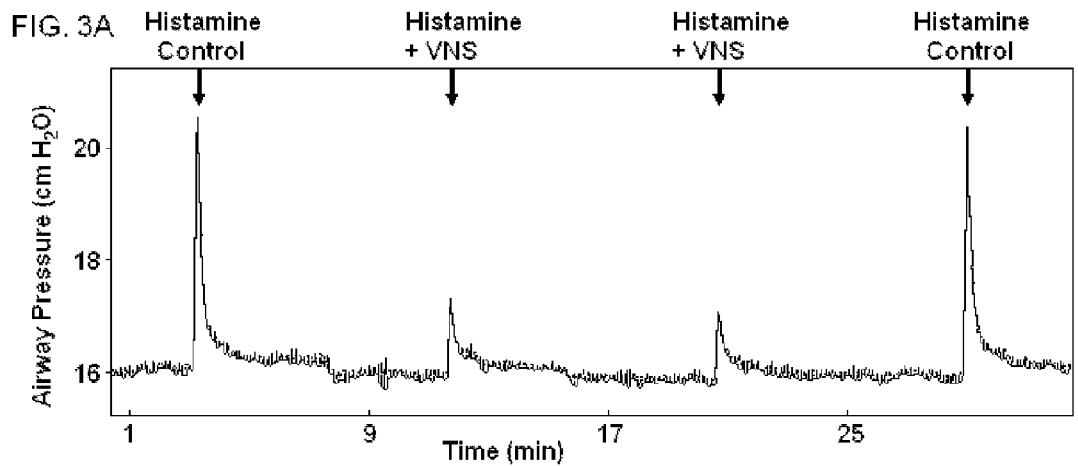
FIGS. 3A-3C show a guinea pig's airway pressure as a function of time, wherein at four time points, bronchoconstriction was induced using a brief histamine challenge, with and without vagus nerve stimulation (FIG. 3A); the results of a succession of such challenges in a single animal (FIG. 3B); and the corresponding results for 16 different animals (FIG. 3C).
Figure 3B:
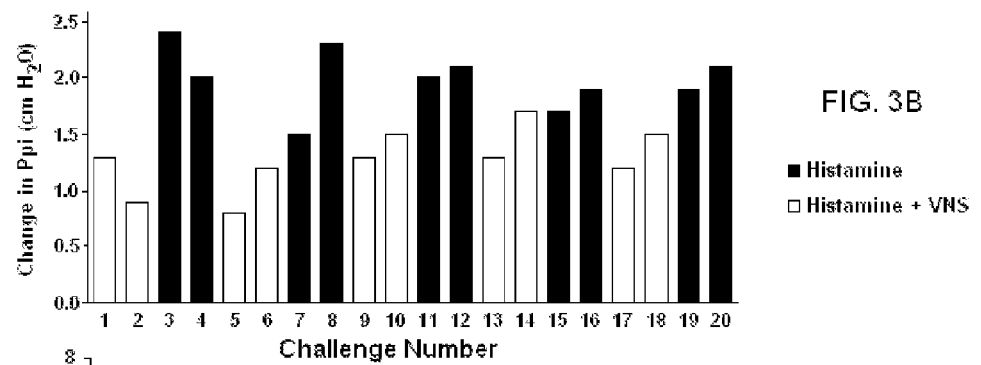
Figure 3C:
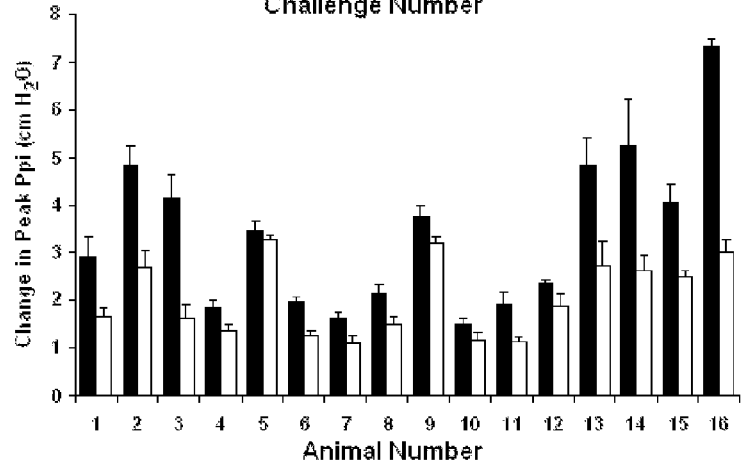

The results are illustrated in FIGS. 3A-3C. In FIG. 3A, an animal's airway pressure is shown as a function of time, and at intervals shown there, bronchoconstriction was induced using a brief histamine challenge. With histamine alone as the intervention, the challenge is seen to produce significant increases of airway pressure, but when the challenge is performed in combination with stimulation of the vagus nerve (VNS) according to the present invention, a significantly smaller increase of airway pressure is observed. FIG. 3B shows the results of a succession of such challenges in a single animal. As seen there, the magnitude of the increase is variable, but a challenge that includes VNS almost invariably results in a smaller increase in airway pressure than a challenge with histamine alone. Results like those shown in FIG. 3B are shown in FIG. 3C for sixteen animals. As seen there, the magnitude of the air pressure increase varies from animal to animal, but almost invariably, when VNS is included with the challenge, the result is a smaller increase in airway pressure than a challenge with histamine alone. In general, VNS reduced the peak change in Ppi following a histamine challenge by approximately 60%.

Similar results were confirmed in a study in swine, demonstrating that the VNS procedure is applicable to larger animals as well. These studies suggest that VNS can reduce bronchoconstriction and may prove useful as a therapy in the treatment of reactive airway disease [HOFFMANN, T. J., Mendez, S., Staats, P., Emala, C. W., Guo, P. Inhibition of histamine-induced bronchoconstriction in guinea pig and swine by pulsed electrical vagus nerve stimulation. Neuromodulation 12 (4, 2009):261-269].

Low Voltage Vagal Nerve Stimulation Reduces Bronchoconstriction in Guinea Pigs Through Catecholamine Release.

A second set of experiments was performed to evaluate the mechanism of action by which VNS reduces bronchoconstriction in guinea pigs. Under IACUC approved protocols, male Hartley guinea pigs were anesthetized with urethane and ventilated by tracheostomy. Bronchoconstriction was induced via intravenous histamine or acetylcholine with or without simultaneous, bilateral VNS at 25 Hz, 200 ms, 1-3 V. Airway pressure recordings that are similar to those shown in FIG. 3A were made. Low-voltage VNS was found to attenuate histamine-induced bronchoconstriction ($4.4 \pm 0.3$ vs. $3.2 \pm 0.2$ cm H2O, $p<0.01$). Selective antagonists (L-NAME for iNANC nerve fibers, propranolol for sympathetic nerve fibers), sympathetic nerve depletion with guanethidine, and vagal ligation were then used to elucidate neural pathways that may be responsible for the bronchodilation or anti-bronchoconstriction response. The results of these animal studies were as follows.

Blockade of nitric oxide synthesis by pretreatment with L-NAME (a primary mediator of inhibitory non-adrenergic, non-cholinergic (iNANC) bronchodilator pathways) had little or no effect on VNS-mediated attenuation of bronchoconstriction. Sympathetic nerve depletion with guanethidine also had little or no effect on VNS-mediated attenuation of bronchoconstriction. However, pretreatment with propranolol did reversibly blocked the effect. As shown in FIG. 4A, without pretreatment with propranolol, the effect of VNS at the indicated times was to reduce the magnitude of bronchoconstriction produced by histamine (H) that was administered at the indicated times. However, when propranolol was administered as a pretreatment, as shown in FIG. 4B, the VNS-mediated attenuation of bronchoconstriction was blocked.

Ligating both cephalic vagus nerves caudal to the stimulating electrodes did not block VNS-mediated attenuation of bronchoconstriction, but ligating the vagus nerves between the electrodes and head did block the attenuation of bronchoconstriction (FIG. 4D) as compared with the situation prior to ligation (FIG. 4C). These unexpected findings suggest that VNS could inhibit bronchoconstriction through a purely afferent vagus pathway, but not a purely efferent vagus pathway. We also found that low-voltage VNS increased circulating epinephrine and norepinephrine. These results indicate that low-voltage VNS attenuates histamine-induced bronchoconstriction via activation of afferent nerves, in part by producing a systemic increase in catecholamines likely arising from the adrenal medulla. Furthermore, we tested whether the attenuation by VNS of histamine-induced increases in Ppi was mediated by direct efferent stimulation of sympathetic nerve fibers traveling within the cervical vagus nerve or by stimulation of parasympathetic iNANC nerves in the guinea pig lung. Our results rule out both of these possibilities since ligation of the vagal nerve caudal to the electrodes did not eliminate the bronchoprotection afforded by low-voltage VNS. Moreover, pretreatment with guanethidine or L-NAME to block norepinephrine or nitric oxide release from sympathetic or iNANC nerves, respectively, did not block the bronchoprotection afforded by low-voltage VNS. Although we demonstrated that the VNS-mediated attenuation of bronchoconstriction involves the participation of vagal afferent nerves (and therefore the central nervous system), and that sympathetic non-vagal efferent pathways were also implicated in the mechanisms, the design of the experiments was such that efferent signals sent from the central nervous system to the lungs via the vagus nerve, other than those involving sympathetic or iNANC nerves, were not investigated separately. In that regard, we can conclude only that VNS stimulation between a ligated vagus nerve and the lung did not attenuate bronchoconstriction, with the understanding that such a ligated nerve is not conveying signals to the lung from the central nervous system.

To ensure that the dissection and placement of the stimulation leads direct to the vagus nerve had not damaged the nerve, the amplitude of the applied signal was increased significantly beyond the anticipated therapeutic level until the classic vaso-vagal responses of bradycardia and bronchoconstriction were observed. We found that in the guinea pig model, stimulation of efferent C-fibers causing both bradycardia and bronchoconstriction could only be achieved at voltages 10×-20× greater than those that were used to inhibit bronchoconstriction [HOFFMANN, T. J., Simon, B. J., Zhang, Y., Emala, C. W. Low-Voltage Vagal Nerve Stimulation Reduces Bronchoconstriction in Guinea Pigs Through Catecholamine Release. Neuromodulation. 2012 May 2. doi: 10.1111/j.1525-1403.2012.00454.x.; a preliminary version of this work was published in the following conference proceedings: Bruce J. SIMON, Charles W. Emala, Lawrence M. Lewis, Daniel Theodoro, Yanina Purim-Shem-Tov, Pedro Sepulveda, Thomas J. Hoffmann, Peter Staats. Vagal Nerve Stimulation for Relief of Bronchoconstriction: Preliminary Clinical Data and Mechanism of Action. Proceedings page 119 of Neuromodulation: 2010 and Beyond; North American Neuromodulation Society 13th Annual Meeting, Dec. 3-6, 2009].

These preliminary animal data indicate that VNS activates afferent nerves and may act through a sympathetic reflex pathway to mediate bronchodilation. Thus, we found that bronchodilation resulting from stimulation of the vagus nerve works by causing the systemic release of the natural, endogenous β-agonists, epinephrine and norepinephrine. These catecholamines can reach the constricted bronchial smooth muscle through an internal, systemic pathway, thereby overcoming any potential problems with inhaled β-agonists, for example, due to mucus congestion. The electrical field delivered to the vagus nerve was optimized to stimulate the release of these hormones into the circulation at concentrations that produce bronchial smooth muscle relaxation, but have little effect on heart rate or blood pressure. The data suggest that the release of these catecholamines is mediated by a parasympathetic, afferent vagal signal to the brain, which then triggers an efferent sympathetic signal to stimulate the release of catecholamines from the adrenal glands. These animal data show that the stimulator is effective even if the vagus nerve is tied off distal to the electrode and that the bronchodilation effect can be blocked with the β-blocker propranolol. In addition, stimulation was found to be ineffective in animals that have had their adrenal glands removed.

Evaluation of Noninvasive Vagal Nerve Stimulation in Ragweed Sensitized Beagle Dogs: Methacholine Induced Bronchoconstriction.

Figure 5:
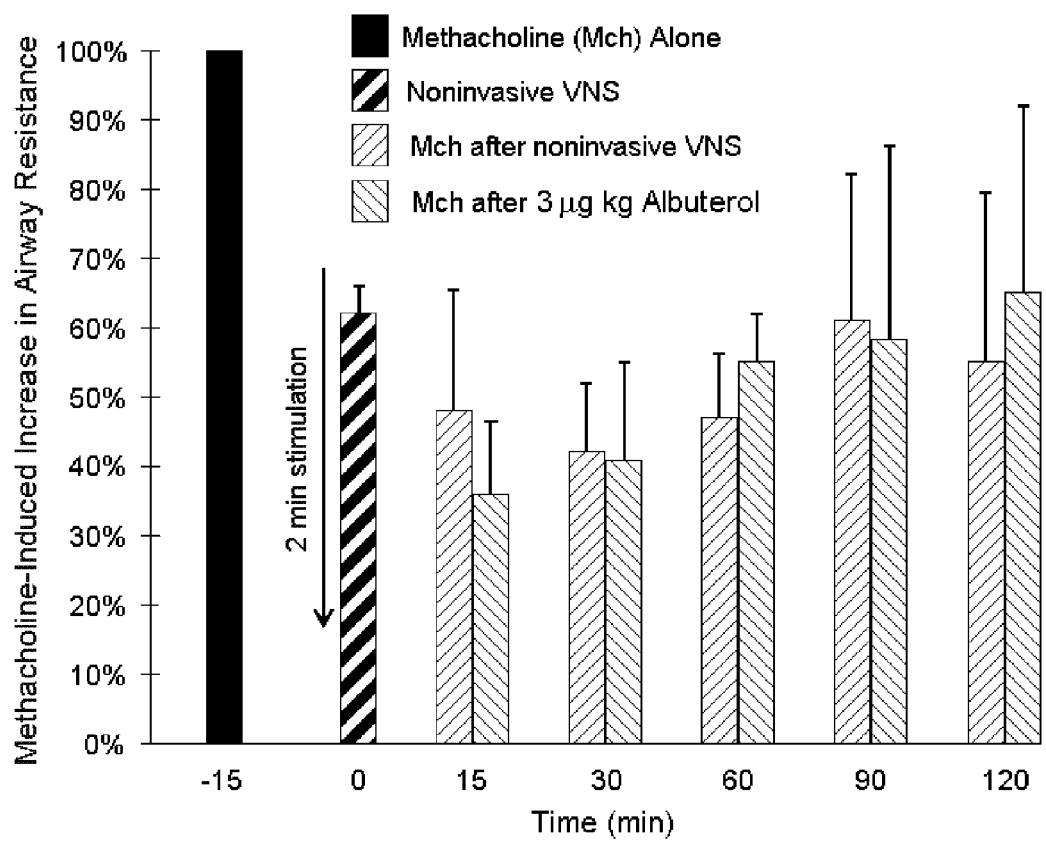
FIG. 5 shows data from a dog experiment demonstrating that noninvasive vagus nerve stimulation results in a significant reduction in methacholine-induced bronchoconstriction at a succession of time points, which is comparable to results obtained with a high-dose of the bronchodilator drug albuterol.

Noninvasive VNS was developed and tested in an established hypersensitive beagle asthma model to confirm that the noninvasive VNS had a safety and efficacy profile similar to percutaneous VNS. The stimulating device was similar to one shown in FIGS. 2A and 6 (known by the inventors as the AlphaCore® device). Dogs were subjected to methacholine (Mch) challenges inducing ~100% increase in airway resistance (FIG. 5, black bar). Dogs were then treated with noninvasive VNS for 90 to 120 seconds (2 min). Treatment with noninvasive VNS resulted in a significant reduction in Mch-induced bronchoconstriction, which occurred within 1 minute of the VNS (FIG. 5, barber-pole bar).

Subsequent to the noninvasive VNS stimulation, the dogs were repeatedly challenged with the same dose of Mch at 15, 30, 60, 90, and 120 minutes. Noninvasive VNS effects lasted for up to 2 hours, through 5 additional challenges without additional VNS stimulations required, with no significant changes in blood pressure or heart rate. These results are comparable at the same time points to results obtained with high-dose albuterol (a bronchodilator medication, instead of VNS) in the same beagle model (FIG. 5, at the indicated time points). In a second experiment propranolol was given intravenously prior to either albuterol or noninvasive VNS, resulting in a significant reduction in methacholine-induced bronchoconstriction. We conclude from these experiments that the foregoing results that we had obtained in experiments involving invasive VNS may be extrapolated to the present invention involving noninvasive VNS.

Consider now which nerve fibers may be stimulated by the non-invasive vagus nerve stimulation. The waveform disclosed in FIGS. 2C-2E contains significant Fourier components at high frequencies (e.g., 1/200 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22 (Supplement 8, 1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9 (1, 1988): 44-59]. According to REILLY's analysis, the minimum threshold for excitation of myelinated A fibers is 6.2 V/m for a 20 μm diameter fiber, 12.3 V/m for a 10 μm fiber, and 24.6 V/m for a 5 μm diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110(2004): 232-238].

It is understood that although devices of the present invention may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282(1978): 353-364]. Because proper stimulation with the disclosed devices does not result in bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, the jugular A-delta fibers are RAR-like afferents that behave physiologically like C fibers. Because stimulation with the disclosed devices does not produce nociceptive effects that would be produced by jugular A-delta fibers or C fibers, evidently the A-delta fibers may not be stimulated when the amplitude is properly set.

To summarize the foregoing discussion, the delivery, in a patient suffering from severe asthma, COPD, anaphylactic shock, or other bronchoconstrictive exacerbation, of an impulse of energy sufficient to stimulate, block and/or modulate transmission of signals of vagus nerve fibers will result in relaxation of the bronchial smooth muscle, dilating airways. The most likely mechanisms do not involve the stimulation of C fibers; bronchodilation resulting from stimulation of the vagus nerve works in part by causing the systemic release of the natural, endogenous β-agonists from the adrenal medulla; and the stimulation of afferent A and B nerve fibers of the vagus nerve activates neural pathways causing the release of norepinephrine, and/or serotonin and/or GABA onto airway-related vagal preganglionic neurons (AVPNs), thereby antagonizing bronchoconstriction that is mediated by cholinergic nerve fibers. In addition, the release of these inhibitory neurotransmitters causes an inhibition of mucous production in the mucous glands within the airway passages.

Stimulating, blocking and/or modulating the signal in selected nerves to reduce parasympathetic tone provides an immediate emergency response, much like a defibrillator, in situations of severe asthma or COPD attacks or anaphylactic shock, providing immediate temporary dilation of the airways and optionally an increase of heart function until subsequent measures, such as administration of epinephrine, rescue breathing and intubation can be employed. Treatment in accordance with the present invention provides bronchodilation and possibly increased heart function for a long enough period of time so that administered medication such as epinephrine has time to take effect before the patient suffocates.

Preferred Embodiment of the Magnetic Stimulator

A preferred embodiment of magnetic stimulator coil 341 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface. [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, (UMI Microform Number: 9940153, UMI Company, Ann Arbor Mich.)].

Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e., z and are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein.

Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions. The shaping of the electric field is described in terms of the corresponding field equations in commonly assigned application US20110125203 (application Ser. No. 12/964,050), entitled Magnetic stimulation devices and methods of therapy, to SIMON et al., which is hereby incorporated by reference.

Thus, the present invention differs from the device disclosed by CARBUNARU and Durand by deliberately shaping an electric field that is used to transcutaneously stimulate the patient. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

In the dissertation cited above, Carbunaru—FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity of the conducting material and select boundary conditions, thereby shaping the electric fields and currents as described above, but also to create devices that can be applied practically to any surface of the body. The volume of the container containing electrically conducting medium is labeled in FIGS. 2A-2B as 351. Use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. This allows for minimal heating of the coil(s) and deeper tissue stimulation. However, application of the conducting medium to the surface of the patient is difficult to perform in practice because the tissue contours (head, arms, legs, neck, etc.) are not planar. To solve this problem, in the preferred embodiment of the present invention, the toroidal coil is embedded in a structure which is filled with a conducting medium having approximately the same conductivity as muscle tissue, as now described.

In one embodiment of the invention, the container contains holes so that the conducting material (e.g., a conducting gel) can make physical contact with the patient's skin through the holes. For example, the conducting medium 351 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNA-GEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 341 in FIG. 2A reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain other peripheral nerves.

Figure 6A:
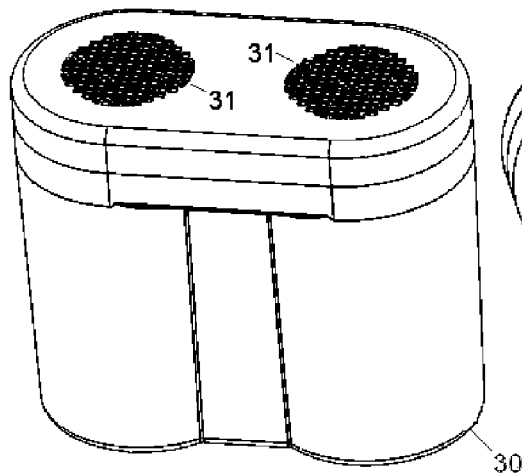
FIGS. 6A-6E illustrate a dual-toroid magnetic stimulator coil according to an embodiment of the present invention, which is shown to be situated within a housing that contains electrically conducting material (FIGS. 6A-6D), and it also shows the housing and cap of the dual-toroid magnetic stimulator attached via cable to a box containing the device's impulse generator, control unit, and power source (FIG. 6E).
Figure 6B:
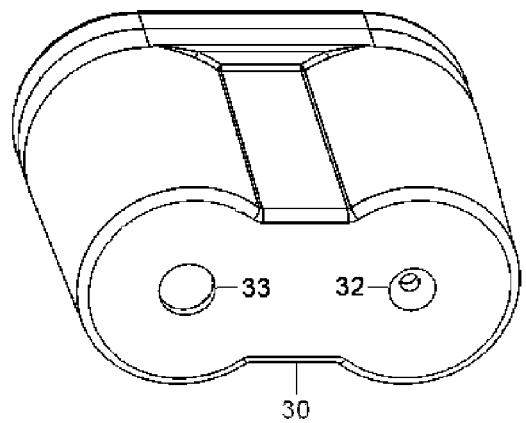
Figure 6C:
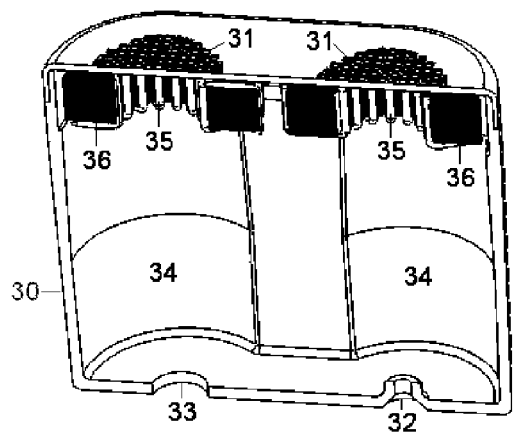
Figure 6D:
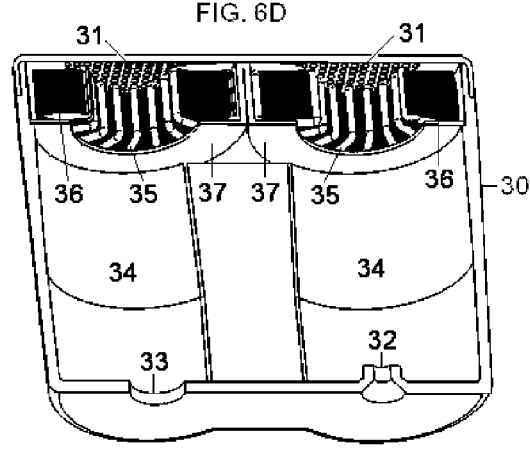

This preferred embodiment of the invention is shown in FIGS. 6A-6D. FIGS. 6A and 6B respectively provide top and bottom views of the outer surface of the toroidal magnetic stimulator 30. FIGS. 6C and 6D respectively provide top and bottom views of the toroidal magnetic stimulator 30, after sectioning along its long axis to reveal the inside of the stimulator.

FIGS. 6A-6D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

FIGS. 6B-6D show openings at the opposite end of the stimulator 30. One of the openings is an electronics port 32 through which wires pass from the stimulator coil(s) to the impulse generator (310 in FIG. 2A). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 6C and 6D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (4, 2001): 434-441].

FIGS. 6C and 6D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 6C and 6D, the coils 35 and cores 36 around which they are wound are mounted as close as practical to the corresponding mesh 31 with openings through which conducting gel passes to the surface of the patient's skin. As seen in FIG. 6D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

Signal generators for magnetic stimulators have been described for commercial systems [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006], as well as for custom designs for a control unit 330, impulse generator 310 and power source 320 [Eric BASHAM, Zhi Yang, Natalia Tchemodanov, and Wentai Liu. Magnetic Stimulation of Neural Tissue: Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to Charles M. Epstein; U.S. Pat. No. 5,718,662, entitled Apparatus for the magnetic stimulation of cells or tissue, to Reza Jalinous; U.S. Pat. No. 5,766,124, entitled Magnetic stimulator for neuro-muscular tissue, to Polson]. Conventional magnetic nerve stimulators use a high current impulse generator that may produce discharge currents of 5,000 amps or more, which is passed through the stimulator coil, and which thereby produces a magnetic pulse. Typically, a transformer charges a capacitor in the impulse generator 310, which also contains circuit elements that limit the effect of undesirable electrical transients. Charging of the capacitor is under the control of a control unit 330, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus.

Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology. vol 85, pp. 253-264, 1992; Nafia AL-MUTAWALY, Hubert de Bruin, and Gary Hasey. The Effects of Pulse Configuration on Magnetic Stimulation. Journal of Clinical Neurophysiology 20(5):361-370, 2003].

Furthermore, a potential practical disadvantage of using magnetic stimulator coils is that they may overheat when used over an extended period of time. Use of the above-mentioned toroidal coil and container of electrically conducting medium addresses this potential disadvantage. However, because of the poor coupling between the stimulating coils and the nerve tissue, large currents are nevertheless required to reach threshold electric fields. At high repetition rates, these currents can heat the coils to unacceptable levels in seconds to minutes depending on the power levels and pulse durations and rates. Two approaches to overcome heating are to cool the coils with flowing water or air or to increase the magnetic fields using ferrite cores (thus allowing smaller currents). For some applications where relatively long treatment times at high stimulation frequencies may be required, e.g. treating acute asthma attacks by stimulating the vagus nerve, neither of these two approaches are adequate. Water-cooled coils overheat in a few minutes. Ferrite core coils heat more slowly due to the lower currents and heat capacity of the ferrite core, but also cool off more slowly and do not allow for water-cooling since the ferrite core takes up the volume where the cooling water would flow.

A solution to this problem is to use a fluid which contains ferromagnetic particles in suspension like a ferrofluid, or magnetorheological fluid as the cooling material. Ferrofluids are colloidal mixtures composed of nanoscale ferromagnetic, or ferrimagnetic, particles suspended in a carrier fluid, usually an organic solvent or water. The ferromagnetic nanoparticles are coated with a surfactant to prevent their agglomeration (due to van der Waals forces and magnetic forces). Ferrofluids have a higher heat capacity than water and will thus act as better coolants. In addition, the fluid will act as a ferrite core to increase the magnetic field strength. Also, since ferrofluids are paramagnetic, they obey Curie's law, and thus become less magnetic at higher temperatures. The strong magnetic field created by the magnetic stimulator coil will attract cold ferrofluid more than hot ferrofluid thus forcing the heated ferrofluid away from the coil. Thus, cooling may not require pumping of the ferrofluid through the coil, but only a simple convective system for cooling. This is an efficient cooling method which may require no additional energy input [U.S. Pat. No. 7,396,326 and published applications US2008/0114199, US2008/0177128, and US2008/0224808, all entitled Ferrofluid cooling and acoustical noise reduction in magnetic stimulators, respectively to Ghiron et al., Riehl et al., Riehl et al. and Ghiron et al.].

Magnetorheological fluids are similar to ferrofluids but contain larger magnetic particles which have multiple magnetic domains rather than the single domains of ferrofluids. [U.S. Pat. No. 6,743,371, Magneto sensitive fluid composition and a process for preparation thereof, to John et al.]. They can have a significantly higher magnetic permeability than ferrofluids and a higher volume fraction of iron to carrier. Combinations of magnetorheological and ferrofluids may also be used [M T LOPEZ-LOPEZ, P Kuzhir, S Lacis, G Bossis, F Gonzalez-Caballero and J D G Duran. Magnetorheology for suspensions of solid particles dispersed in ferrofluids. J. Phys.: Condens. Matter 18 (2006) S2803-S2813; Ladislau VEKAS. Ferrofluids and Magnetorheological Fluids. Advances in Science and Technology Vol. 54 (2008) pp 127-136.].

Commercially available magnetic stimulators include circular, parabolic, figure-of-eight (butterfly), and custom designs that are available commercially [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006]. Additional embodiments of the magnetic stimulator coil 341 have been described [U.S. Pat. No. 6,179,770, entitled Coil assemblies for magnetic stimulators, to Stephen Mould; Kent DAVEY. Magnetic Stimulation Coil and Circuit Design. IEEE Transactions on Biomedical Engineering, Vol. 47 (No. 11, November 2000): 1493-1499]. Many of the problems that are associated with such conventional magnetic stimulators, e.g., the complexity of the impulse-generator circuitry and the problem with overheating, are largely avoided by the toroidal design shown in FIGS. 6C-6D.

Figure 6E:
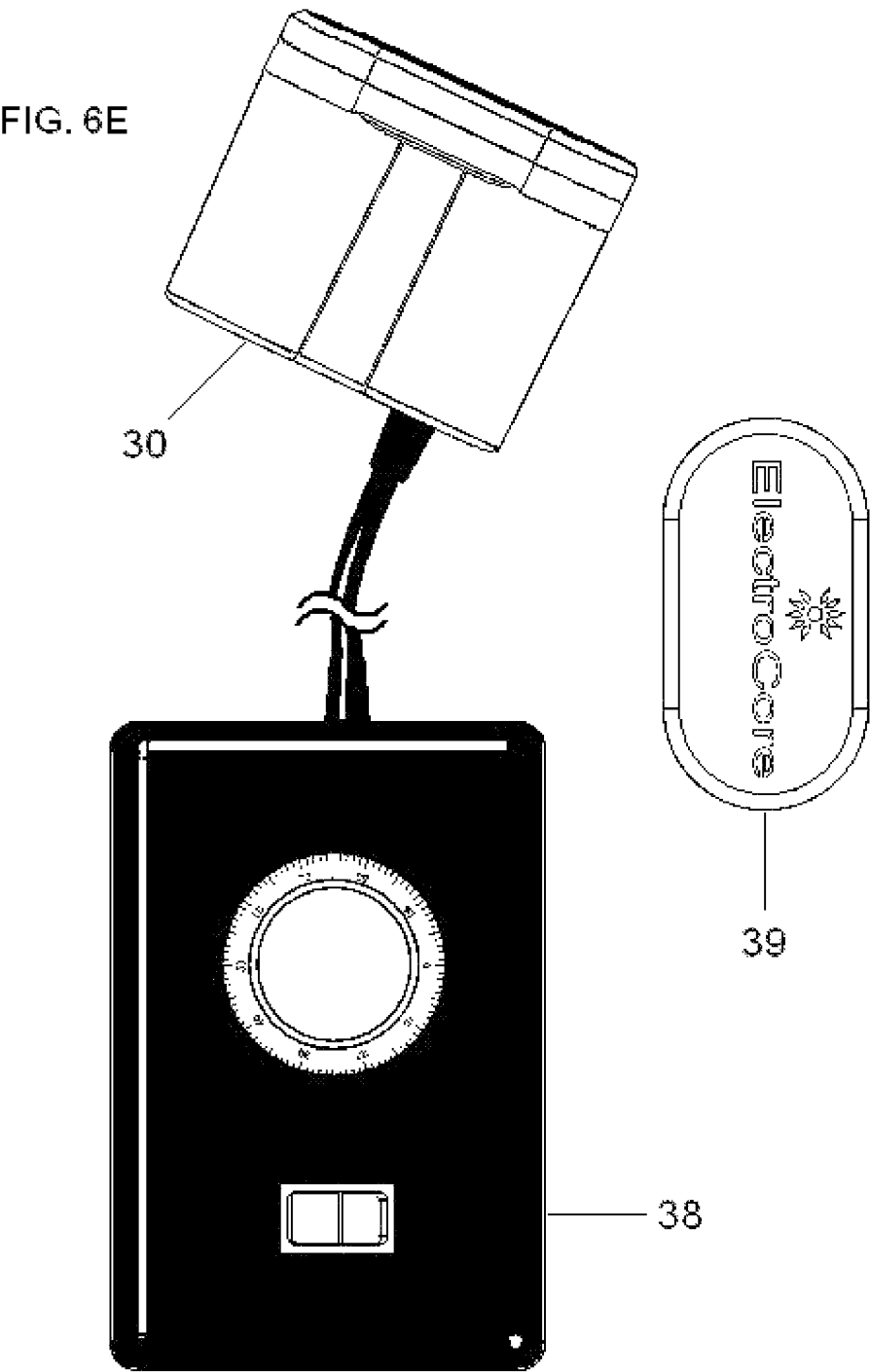

Thus, use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. Therefore, with the present invention, it is possible to generate waveforms shown in FIGS. 2C-2E with relatively simple, low-power circuits that are powered by batteries. The circuits may be enclosed within a box 38 as shown in FIG. 6E, or the circuits may be attached to the stimulator itself (FIGS. 6A-6D) to be used as a hand-held device. In either case, control over the unit may be made using only an on/off switch and power knob. The only other component that may be needed might be a cover 39 to keep the conducting fluid from leaking or drying out between uses. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIGS. 2D and 2E, shaping an elongated electrical field of effect.

Preferred Embodiment of the Electrode-Based Stimulator

In another embodiment of the invention, electrodes applied to the surface of the neck, or to some other surface of the body, are used to non-invasively deliver electrical energy to a nerve, instead of delivering the energy to the nerve via a magnetic coil. The vagus nerve has been stimulated previously non-invasively using electrodes applied via leads to the surface of the skin. For example, U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of bronchoconstriction. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of bronchoconstriction.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. However, none of the disclosures in these patents or patent applications for electrical stimulation of the vagus nerve at the ear are used to treat bronchoconstriction.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

Considering that the nerve stimulating device 301 in FIG. 2A and the nerve stimulating device 302 in FIG. 2B both control the shape of electrical impulses, their functions are analogous, except that one stimulates nerves via a pulse of a magnetic field, and the other stimulates nerves via an electrical pulse applied through surface electrodes. Accordingly, general features recited for the nerve stimulating device 301 apply as well to the latter stimulating device 302 and will not be repeated here. The preferred parameters for each nerve stimulating device are those that produce the desired therapeutic effects.

A preferred embodiment of an electrode-based stimulator is shown in FIG. 7A. A cross-sectional view of the stimulator along its long axis is shown in FIG. 7B. As shown, the stimulator (730) comprises two heads (731) and a body (732) that joins them. Each head (731) contains a stimulating electrode. The body of the stimulator (732) contains the electronic components and battery (not shown) that are used to generate the signals that drive the electrodes, which are located behind the insulating board (733) that is shown in FIG. 7B. However, in other embodiments of the invention, the electronic components that generate the signals that are applied to the electrodes may be separate, but connected to the electrode head (731) using wires. Furthermore, other embodiments of the invention may contain a single such head or more than two heads.

Heads of the stimulator (731) are applied to a surface of the patient's body, during which time the stimulator may be held in place by straps or frames (not shown), or the stimulator may be held against the patient's body by hand. In either case, the level of stimulation power may be adjusted with a wheel (734) that also serves as an on/off switch. A light (735) is illuminated when power is being supplied to the stimulator. An optional cap may be provided to cover each of the stimulator heads (731), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Figure 7C:
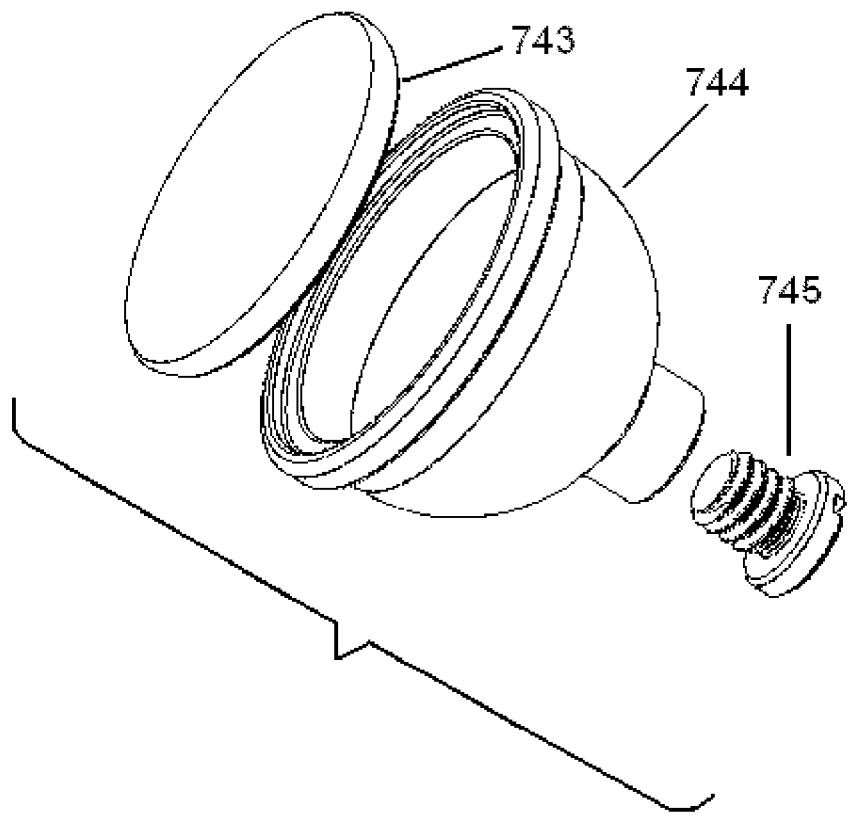
Figure 7D:
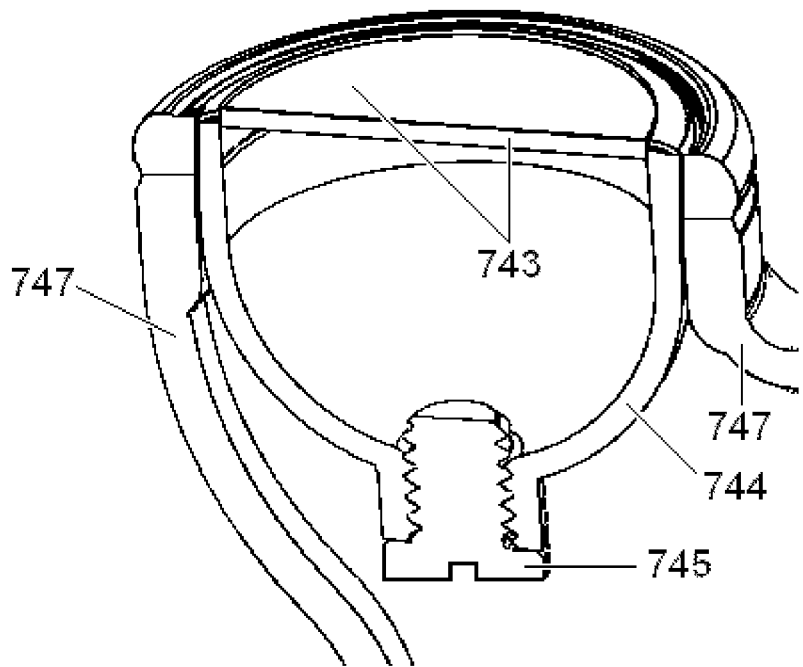

Details of one embodiment of the stimulator head are shown in FIGS. 7C and 7D. The electrode head may be assembled from a disc without fenestration (743), or alternatively from a snap-on cap that serves as a tambour for a dielectric or conducting membrane, or alternatively the head may have a solid fenestrated head-cup. The electrode may also be a screw (745). The preferred embodiment of the disc (743) is a solid, ordinarily uniformly conducting disc (e.g., metal such as stainless steel), which is possibly flexible in some embodiments. An alternate embodiment of the disc is a non-conducting (e.g., plastic) aperture screen that permits electrical current to pass through its apertures, e.g., through an array of apertures (fenestration). The electrode (745, also 340 in FIG. 2B) seen in each stimulator head may have the shape of a screw that is flattened on its tip. Pointing of the tip would make the electrode more of a point source, such that the equations for the electrical potential may have a solution corresponding more closely to a far-field approximation. Rounding of the electrode surface or making the surface with another shape will likewise affect the boundary conditions that determine the electric field. Completed assembly of the stimulator head is shown in FIG. 7D, which also shows how the head is attached to the body of the stimulator (747).

If a membrane is used, it ordinarily serves as the interface shown as 351 in FIG. 2B. For example, the membrane may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment, apertures of the disc may be open, or they may be plugged with conducting material, for example, KM10T hydrogel from Katecho Inc., 4020 Gannett Ave., Des Moines Iowa 50321. If the apertures are so-plugged, and the membrane is made of conducting material, the membrane becomes optional, and the plug serves as the interface 351 shown in FIG. 2B.

The head-cup (744) is filled with conducting material (350 in FIG. 2B), for example, SIGNAGEL Electrode Gel from Parker Laboratories, Inc., 286 Eldridge Rd., Fairfield N.J. 07004. The head-cup (744) and body of the stimulator are made of a non-conducting material, such as acrylonitrile butadiene styrene. The depth of the head-cup from its top surface to the electrode may be between one and six centimeters. The head-cup may have a different curvature than what is shown in FIGS. 7C-7D, or it may be tubular or conical or have some other inner surface geometry that will affect the Neumann boundary conditions that determine the electric field strength.

If an outer membrane is used and is made of conducting materials, and the disc (743) in FIG. 7C is made of solid conducting materials such as stainless steel, then the membrane becomes optional, in which case the disc may serve as the interface 351 shown in FIG. 2B. Thus, an embodiment without the membrane is shown in FIGS. 7C and 7D. FIG. 7E shows that this version of the device comprises a solid (but possibly flexible in some embodiments) conducting disc that cannot absorb fluid, the non-conducting stimulator head (744) into or onto which the disc is placed, and the electrode (745), which is also a screw. It is understood that the disc (743) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 7D, these items are assembled to become a sealed stimulator head that is attached to the body of the stimulator (747). The disc (743) may screw into the stimulator head (744), it may be attached to the head with adhesive, or it may be attached by other methods that are known in the art. The chamber of the stimulator head-cup is filled with a conducting gel, fluid, or paste, and because the disc (743) and electrode (745) are tightly sealed against the stimulator head-cup (744), the conducting material within the stimulator head cannot leak out.

In some embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface (351 in FIG. 2B) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a non-invasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIGS. 2C-2E). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolyte material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113(1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25 (1987): 359-360; Thierry KELLER and Andreas Kuhn. Electrodes for transcutaneous (surface) electrical stimulation. Journal of Automatic Control, University of Belgrade 18 (2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRISEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIGS. 2C-2E). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25(1987): 359-360; Yongmin K I M, H. Gunter Zieber, and Frank A. Yang. Uniformity of current density under stimulating electrodes. Critical Reviews in Biomedical Engineering 17 (1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 8, showing a device in which electrically conducting material is dispensed from the device to the patient's skin. In this embodiment, the interface (351 in FIG. 2B) is the conducting material itself. FIGS. 8A and 8B respectively provide top and bottom views of the outer surface of the electrical stimulator 50. FIG. 8C provides a bottom view of the stimulator 50, after sectioning along its long axis to reveal the inside of the stimulator.

Figure 8A:
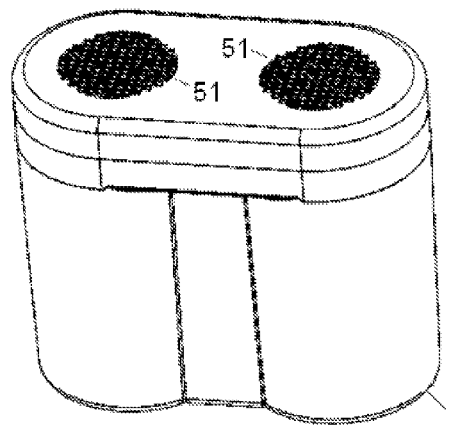
FIGS. 8A-8D illustrate an alternate embodiment of the dual-electrode stimulator (FIGS. 8A-8C), also comparing it with an embodiment of the magnetic stimulator according to the present invention (FIG. 8D).
Figure 8B:
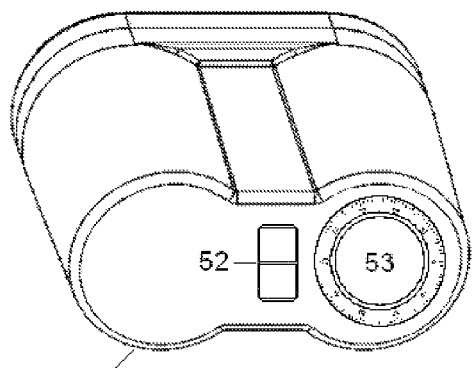
Figure 8C:
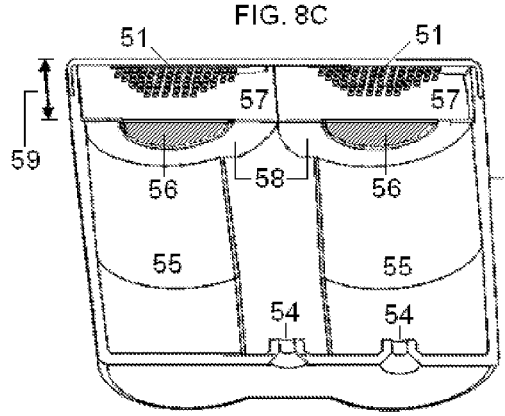

FIGS. 8A and 8C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 8A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 8B and 8C show the bottom of the self-contained stimulator 50. An on/off switch 52 is attached through a port 54, and a power-level controller 53 is attached through another port 54. The switch is connected to a battery power source (320 in FIG. 2B), and the power-level controller is attached to the control unit (330 in FIG. 2B) of the device. The power source battery and power-level controller, as well as the impulse generator (310 in FIG. 2B) are located (but not shown) in the rear compartment 55 of the housing of the stimulator 50.

Individual wires (not shown) connect the impulse generator (310 in FIG. 2B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 2B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 8 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In preferred embodiments of the electrode-based stimulator shown in FIG. 2A-2B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18 (2, 2008):35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20 (1, 1994):29-35].

For example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

Although the electrode may consist of arrays of conducting material, the embodiments shown in FIGS. 7 and 8 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 7 and 8 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21 (1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71(1999): 4944-4950]. In fact, patients found the design shown in FIGS. 7A-7D and FIGS. 8A-8D to be less painful in a direct comparison with a commercially available grid-pattern electrode [UltraStim grid-pattern electrode, Axelggard Manufacturing Company, 520 Industrial Way, Fallbrook CA, 2011]. The embodiment of the electrode that uses capacitive coupling is particularly suited to the generation of uniform stimulation currents [Yongmin K I M, H. Gunter Zieber, and Frank A. Yang. Uniformity of current density under stimulating electrodes. Critical Reviews in Biomedical Engineering 17 (1990, 6): 585-619].

The electrode-based stimulator designs shown in FIGS. 7 and 8 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 7 and 8 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 7 and 8 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in commonly assigned application US20110230938 (application Ser. No. 13/075,746) entitled Devices and methods for non-invasive electrical stimulation and their use for vagal nerve stimulation on the neck of a patient, to SIMON et al., which is hereby incorporated by reference.

In one embodiment, the magnetic stimulator coil 341 in FIG. 2A has a body that is similar to the electrode-based stimulator shown in FIG. 8C. To compare the electrode-based stimulator with the magnetic stimulator, refer to FIG. 8D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 8D:
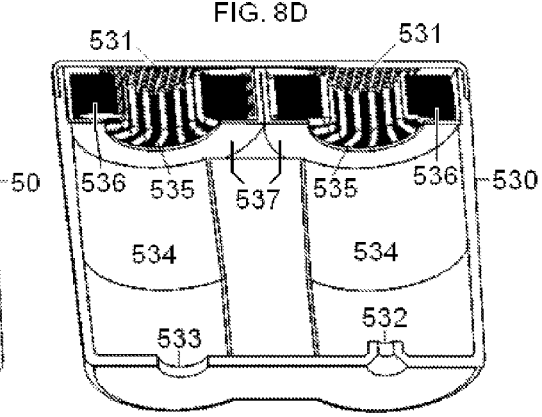

As seen in FIG. 8D, a mesh 531 has openings that permit a conducting gel (within 351 in FIG. 2A) to pass from the inside of the stimulator to the surface of the patient's skin at the location of nerve or tissue stimulation. Thus, the mesh with openings 531 is the part of the magnetic stimulator that is applied to the skin of the patient.

FIG. 8D also shows openings at the opposite end of the magnetic stimulator 530. One of the openings is an electronics port 532 through which wires pass from the stimulator coil(s) to the impulse generator (310 in FIG. 2A). The second opening is a conducting gel port 533 through which conducting gel (351 in FIG. 2A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 8D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 8D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 2A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 8D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 8C and the magnetic stimulator shown in FIG. 8D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Application of the Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 9:
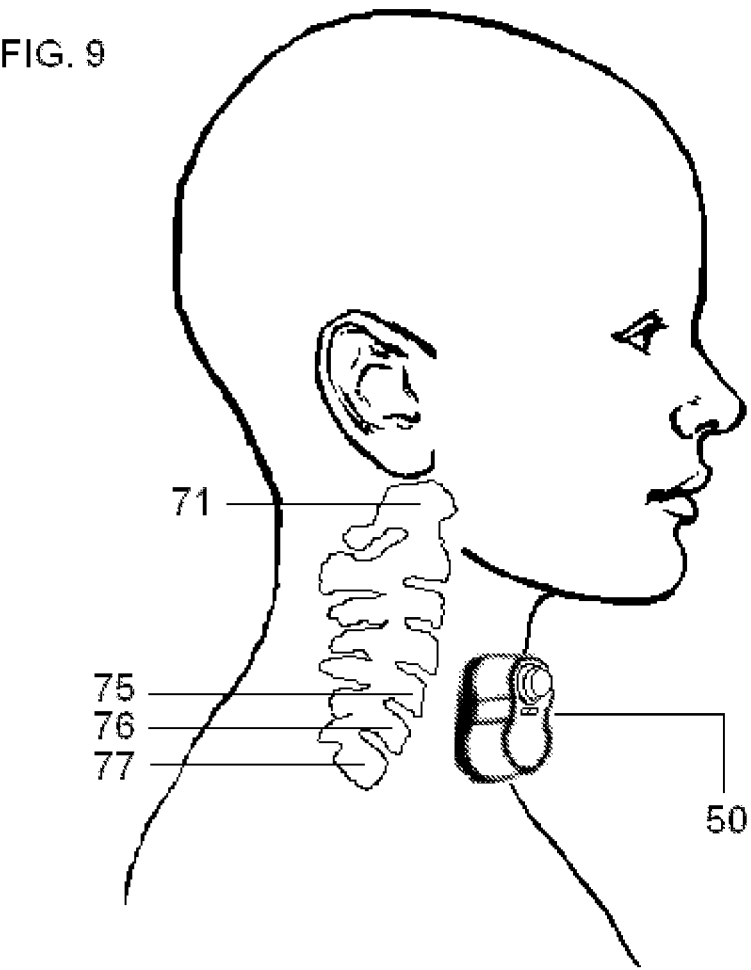
FIG. 9 illustrates the approximate position of the housing of the stimulator according one embodiment of the present invention, when used to stimulate the right vagus nerve in the neck of a patient.

FIG. 9 illustrates use of the devices shown in FIGS. 2, 6, 7, and 8 to stimulate the vagus nerve at that location in the neck, in which the stimulator device 50 or 530 in FIGS. 8C-8D is shown to be applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 10:
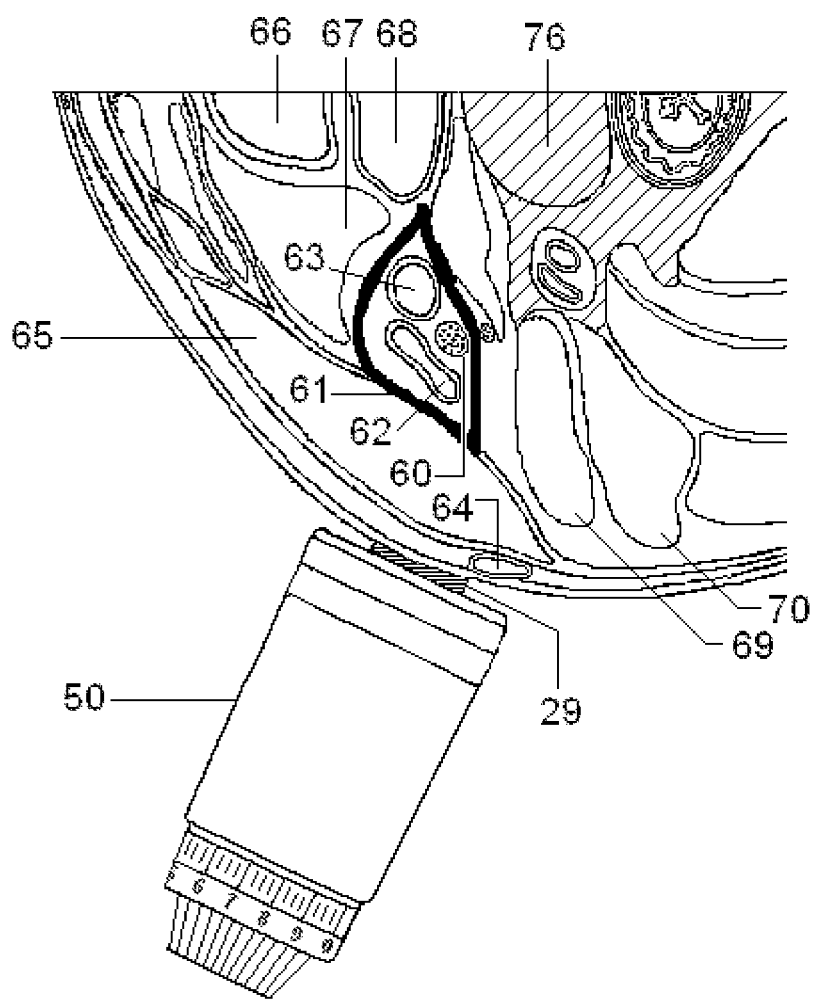
FIG. 10 illustrates the housing of the stimulator according to one embodiment of the present invention, when positioned to stimulate a vagus nerve in the patient's neck, wherein the stimulator is applied to the surface of the neck in the vicinity of the identified anatomical structures.

FIG. 10 provides a more detailed view of use of the electrical stimulator, when positioned to stimulate the vagus nerve at the neck location that is indicated in FIG. 9. As shown, the stimulator 50 in FIGS. 8A-8C touches the neck indirectly, by making electrical contact through conducting gel 29 (or other conducting material) which may be is dispensed through mesh openings (identified as 51 in FIGS. 8A, 8C) of the stimulator or applied as an electrode gel or paste. The layer of conducting gel 29 in FIG. 10 is shown to connect the device to the patient's skin, but it is understood that the actual location of the gel layer(s) may be generally determined by the location of mesh 51 shown in FIG. 8A, 8C. Furthermore, it is understood that for other embodiments of the invention, the conductive head of the device may not necessitate the use of additional conductive material being applied to the skin.

The vagus nerve 60 is identified in FIG. 10, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 10, with bony structure indicated by hatching marks.

Methods of treating a patient comprise stimulating the vagus nerve as indicated in FIGS. 9 and 10, using the electrical stimulation devices that are disclosed herein. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 9 or 10). The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2C-2E. The pattern of a burst followed by silent inter-burst period repeats itself with a period of T. For example, the sinusoidal period may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 1 to 1000 microseconds, preferably 200 microseconds. A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. For some patients, a single stimulation session of 90 to 120 seconds may be performed (acute situation). For other patients, the stimulation may be performed for 30 minutes and the treatment is performed once a week for 12 weeks or longer (chronic situation). However, it is understood that parameters of the stimulation protocol may be varied in response to heterogeneity in the pathophysiology of patients.

In other embodiments of the invention, pairing of vagus nerve stimulation may be with a time-varying sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Such paired stimulation does not necessarily rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470 (7332, 2011):101-4].

The individualized selection of parameters for the nerve stimulation protocol may based on trial and error in order to obtain a beneficial response without the sensation of pain or muscle twitches. Ordinarily, the amplitude of the stimulation signal is set to the maximum that is comfortable for the patient, and then the other stimulation parameters are adjusted. Alternatively, the selection of parameter values may involve tuning as understood in control theory, and as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10 (5, 2004):378-82].

Measurements that are Used to Assess the Extent of a Patient's Bronchoconstriction Before presenting data in which the disclosed vagus nerve stimulation devices and methods are applied to patients, as a preliminary, we describe measurements that are used to measure bronchoconstriction or bronchodilation. The magnitude of bronchial constriction in a patient is typically evaluated with a measurement referred to as the Forced Expiratory Volume in one second (FEV1). FEV1 represents the amount of air that a patient exhales (expressed in liters) in the first second of a pulmonary function test, which is typically performed with a spirometer. The spirometer compares the FEV1 result to a standard for the patient, which is based on the predicted value for the patient's weight, height, sex, age and race. This comparison is then expressed as a percentage of the FEV1 as predicted. Thus, if the volume of air exhaled by a patient in the first second is 60% of the predicted value based on the standard, the FEV1 will be expressed in both the actual liters exhaled and as a percentage of predicted (i.e., 60% of predicted). In practice, a baseline value of FEV1 is measured, and after a therapeutic intervention, a second value of FEV1 is measured in order to ascertain the efficacy of the intervention.

Certain other non-invasive measurements may act as surrogates for the measurement of FEV1. Those other measurements are particularly useful for patients who cannot cooperate to perform measurements made by spirometry, or for situations in which it is not possible to perform spirometry. Because those other measurements may be used to generate a non-invasive, continuous signal that indicates the efficacy of stimulating the selected nerves, they will be discussed below in connection with their use to provide a feedback signal in the present invention, for adjusting the power of the applied impulse, as well as for adjustment of other stimulation parameters. It should be noted here that one of them, the interrupter technique (Rint) measures airway resistance, which according to Poiseuille's Law for laminar air flow, is inversely proportional to the fourth power of the caliber of dilation of the bronchi.

The measurement of FEV1 entails first measuring forced expiration volume as a function of time (the maximum expiratory flow-volume curve, or MEFV, which may be depicted in different ways, e.g., normalized to percentage of vital capacity), then reading the value of the MEFV curve at the one second point. Because a single parameter such as FEV1 cannot characterize the entire MEFV curve, it is understood that the MEFV curve itself (or a set of parameters derived from it) more accurately represents the patient's respiratory status than the FEV1 value alone [Francois HAAS, Kenneth Axen, and John Salazar Schicchi. Use of Maximum Expiratory Flow-Volume Curve Parameters in the Assessment of Exercise-induced Bronchospasm. Chest 1993; 103:64-68]. For example, applicants also report Peak Expiratory Flow (PEF), which is the maximal flow achieved during the maximally forced expiration initiated at full inspiration, measured in liters per minute. Furthermore, it is understood that in order to understand the functional relationship between the magnitude of bronchoconstriction (literally, a reduction in the average caliber of bronchial lumen) and FEV1, one does so by first considering the relation of each of them to the MEFV curve [Rodney K. LAMBERT and Theodore A. Wilson. Smooth muscle dynamics and maximal expiratory flow in asthma. J Appl Physiol 99: 1885-1890, 2005].

FEV1 is used as an objective index of airway obstruction in a patient, but for a given value of FEV1, different patients may subjectively perceive different amounts of breathlessness corresponding to the work and effort associated with breathing (Work of Breathing, or WOB). Therefore, it is also useful to quantify the patient's subjective sensation of breathlessness, which is often made as a visual analogue scale (VAS) value [BIJL-HOFLAND I D, Cloosterman S G, Folgering H T, Akkermans R P, van den Hoogen H, van Schayck C P. Measuring breathlessness during histamine challenge: a simple standardized procedure in asthmatic patients. Eur Respir J. 13(1999):955-60; Donald A. MAHLER. Mechanisms and measurement of dyspnea in chronic obstructive pulmonary disease. Proc Am Thorac Soc 3(2006): 234-238].

As discussed below in connection with a description of Applicant's clinical data, the present application discloses systems and methods for increasing a patient's FEV1 in a relatively short period of time. Preferably, an impulse of energy in the form of non-invasive vagus nerve stimulation is applied to the patient, which is sufficient to increase the FEV1 of the patient by a clinically significant amount in a period of time less than about 6 hours, preferably less than 3 hours and more preferably less than 90 minutes. In an exemplary embodiment, the clinically significant increase in FEV1 occurs in less than 15 minutes, following ninety seconds of vagus nerve stimulation. A clinically significant amount is defined herein as at least a 12% increase in the patient's FEV1, versus the FEV1 prior to application of the electrical impulse.

Method and devices of the present invention are therefore particularly useful for providing substantially immediate relief of acute symptoms associated with bronchial constriction such as asthma attacks, COPD exacerbations and/or anaphylactic reactions. One of the key advantages of the present invention is the ability to provide almost immediate dilation of the bronchial smooth muscle in patients suffering from acute bronchoconstriction, opening the patient's airways and allowing them to breathe and more quickly recover from an acute episode (i.e., a relatively rapid onset of symptoms that are typically not prolonged or chronic).

Clinical Data Demonstrating that the Disclosed Stimulation Waveform and Devices Bring about Bronchodilation As with the animal data that were described above, we first tested the feasibility of the invention using invasive procedures (percutaneous vagus nerve stimulation), then proceeded to demonstrate the invention using totally noninvasive clinical measurements, as follows.

Feasibility of Percutaneous Vagal Nerve Stimulation for the Treatment of Acute Asthma Exacerbations.

The purpose of this follow-up study was to investigate both the safety and efficacy of VNS, in humans, delivered through a percutaneous electrode (pVNS) for the treatment of acute asthma exacerbations. The study subjects were limited to consenting adult emergency department (ED) patients with no further respiratory problems or other pre-existing medical conditions. Twenty-four ED patients (ages 18-65 years) who failed to respond to one hour of standard of care (SOC) were treated with the percutaneous placement of an electrode near the right carotid sheath (under ultrasound guidance) and then administered 60 minutes of pVNS and SOC. They were compared with a non-randomized control group of 76 subjects who received only SOC.

Figure 11A:
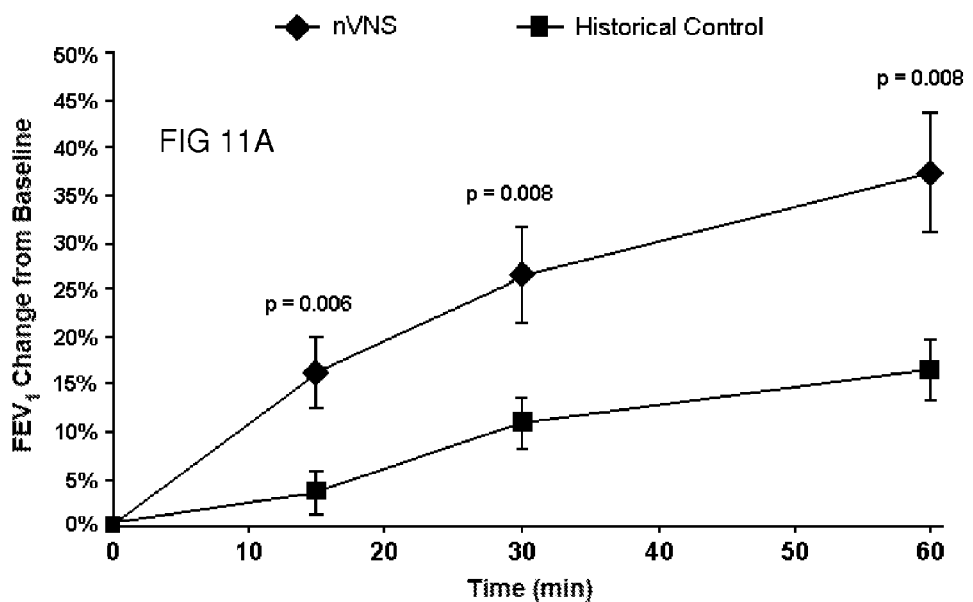
FIGS. 11A-11B show that vagus nerve stimulation improved both FEV1 (FIG. 11A) and work of breathing among twenty-four bronchoconstricted asthma patients who failed to respond to one hour of standard medication (FIG. 11B).
Figure 11B:
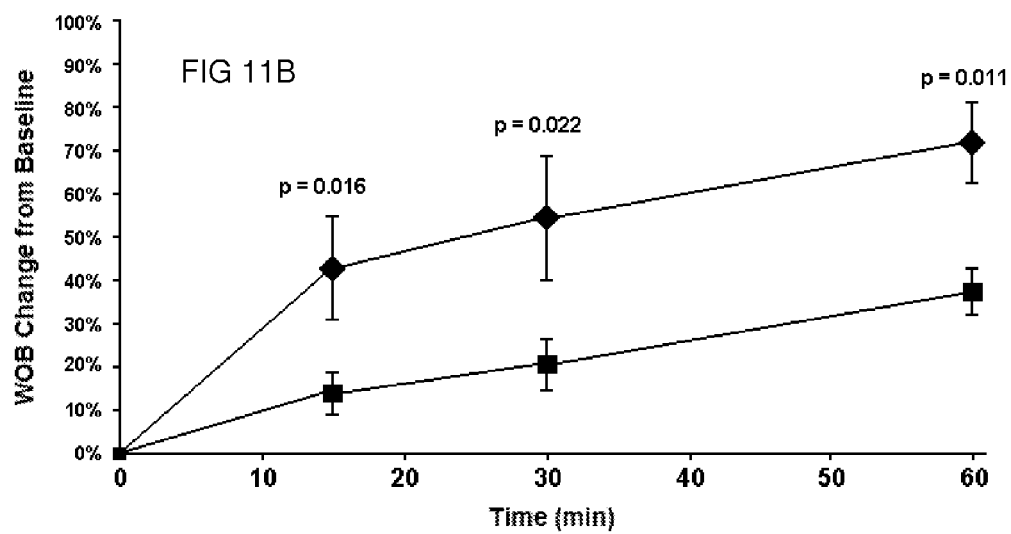

The primary study outcome measures included adverse events, Force Expiratory Volume in 1 sec (FEV1), and improvement in perceived Work of Breathing (WOB) measured on a visual analogue scale. Stimulation for 60 minutes showed remarkable improvement in both FEV1 (FIG. 11A) and WOB (FIG. 11B) without serious adverse events, with superiority in these values over SOC at 15, 30, and 60 minutes with p-values of less than 0.05 [MINER, J. R., Lewis, L. M., Mosnaim, G. S., Varon, J., Theodoro, D. Hoffman, T. J. Feasibility of percutaneous vagus nerve stimulation for the treatment of acute asthma exacerbations." Acad Emerg Med 2012; 19: 421-429].

Clinical Studies with Noninvasive Vagus Nerve Stimulation:

Thirty asthma patients were enrolled in an FDA IDE, prospective, multi-centered pilot study to assess safety and efficacy of the disclosed noninvasive VNS device (the AlphaCore® device). The subjects had a documented reversible component of bronchoconstriction and were instructed to withhold use of an inhaled rescue medication (SABA) until they experienced mild to moderate bronchoconstriction. They then reported to the physician's office for treatment with the AlphaCore, and monitoring of vital signs, dyspnea and spirometry before, during, and for 90 min after a single, 90-second treatment.

Figure 12A:
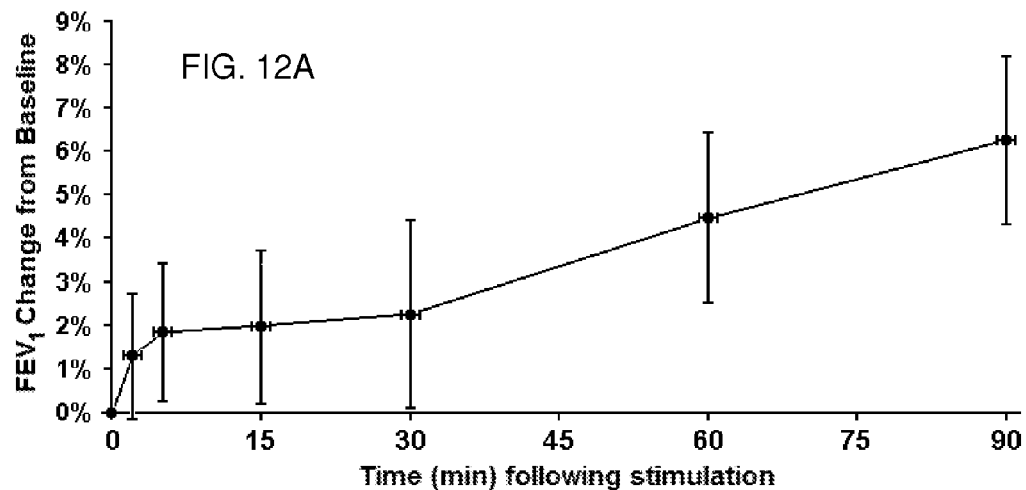
FIGS. 12A-12E show that after 90 seconds of noninvasive vagus nerve stimulation, thirty asthma patients showed an increase in FEV1 (FIG. 12A), improvement in Peak Expiratory Flow (FIG. 12B), reduction in work of breathing VAS score (FIG. 12C), and no significant changes in heart rate (FIG. 12D) or systolic or diastolic blood pressure (FIG. 12E).
Figure 12B:
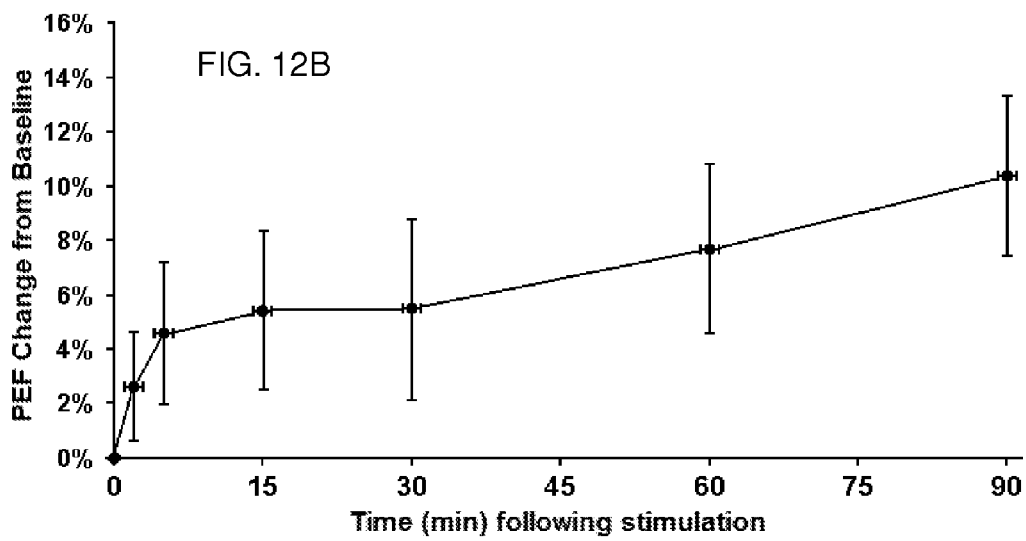
Figure 12C:
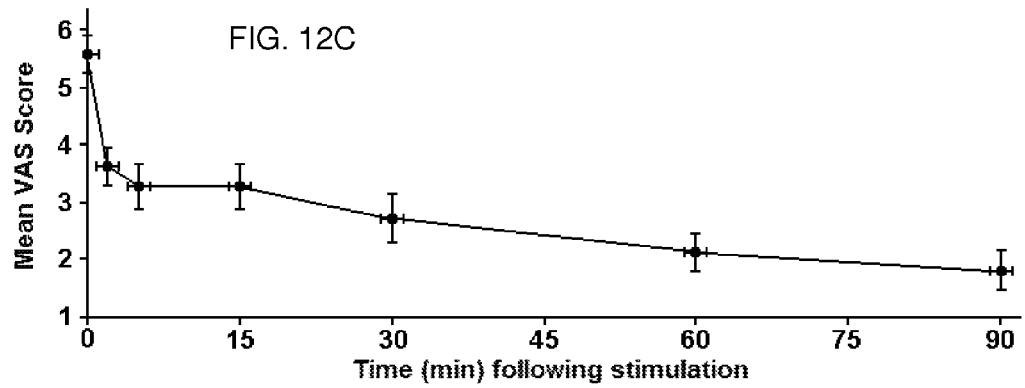
Figure 12D:
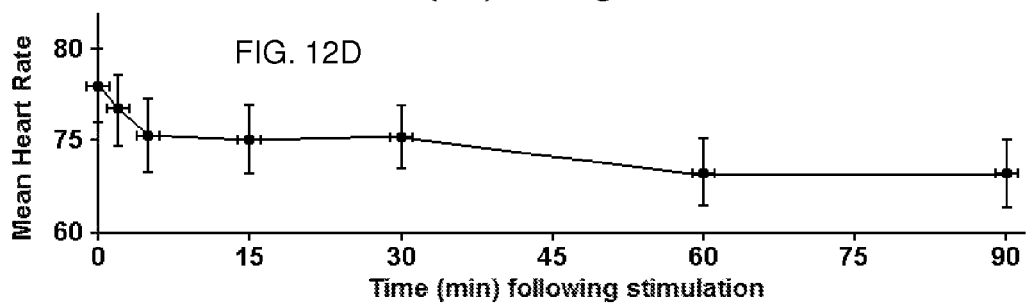
Figure 12E:
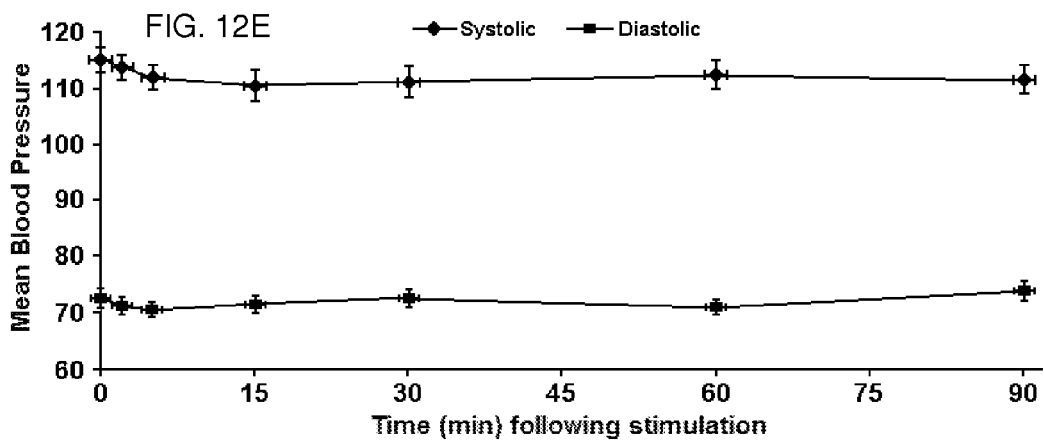

During the 90-seconds of stimulation most patients reported an immediate improvement in breathing. This was reflected in a rapid increase in FEV1 within one minute of stimulation. FEV1 continued to improve over the following 90 minutes (FIG. 12A). Similar improvements were seen in Peak Expiratory Flow (PEF) with greater than a 10% improvement by 90 min (FIG. 12B). Subjectively, patients reported a significant improvement in breathing, as reflected in work of breathing (VAS score) improvement of nearly half in the first few minutes after stimulation, followed by continued reduction in the VAS score (FIG. 12C). No adverse events were reported during or after stimulation. There were no significant changes in ECG, heart rate or systolic or diastolic blood pressure (FIGS. 12D and 12E).

Pilot Clinical Trial in which Patients Take Various Pre- and Post-nVNS Medications.

Figure 14A:
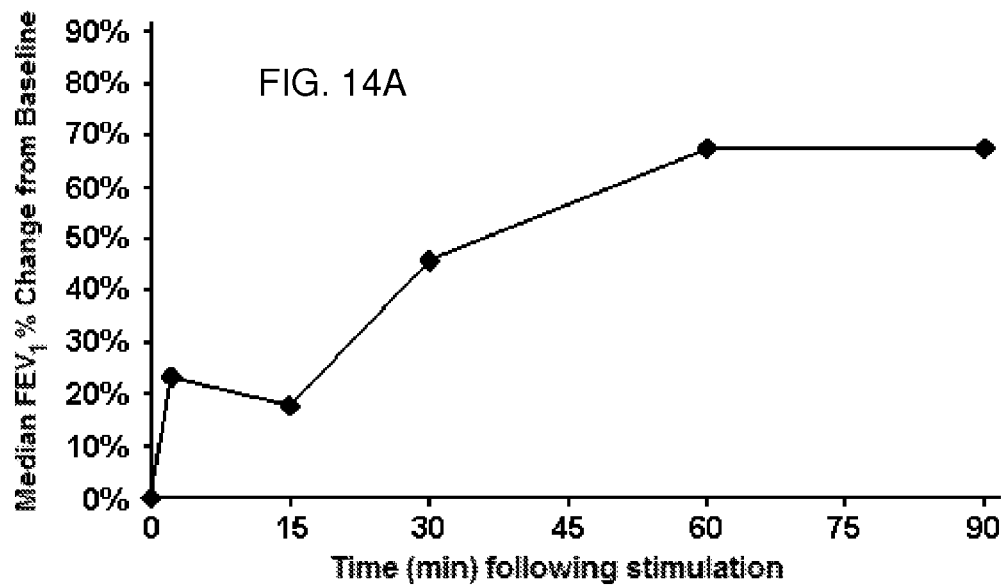
FIGS. 14A-14B show FEV1 (FIG. 14A) and Work of Breathing VAS (FIG. 14B) data as a function of time, for six bronchoconstricted patients who appeared in an emergency department and whose vagus nerves were stimulated two times, 30 minutes apart, for 90 seconds each.
Figure 14B:
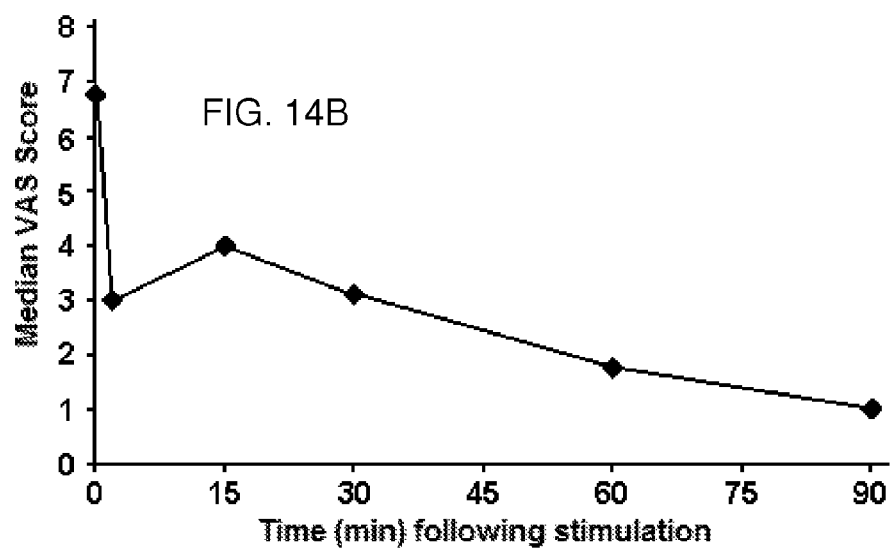

In practice, the patients who are administered noninvasive vagus nerve stimulation (nVNS) in the setting of an emergency department will also be administered a variety of medications prior to and after the nVNS. To ascertain whether the use of nVNS as an adjunctive treatment to standard of medicinal care for the relief of acute bronchoconstriction is safe and effective, and whether the results are influenced by the variety of standard medications that are taken, the following pilot clinical trial was performed. After consent was obtained and screening completed, six subjects were stimulated two times, 30 minutes apart, for 90 seconds each, using the AlphaCore device as described above. The subjects were assessed prior to and immediately post the first stimulation and at 15, 30, 60, and 90 minutes. Follow-up was also conducted at day 7 and day 30. The medications take prior to and after the nVNS are shown as a table in FIG. 13. FIG. 14A summarizes the FEV1 data for these patients as a function of time following the initial stimulation. The 30 minute measurement was taken immediately after the second stimulation. FIG. 14B summarizes the Work of Breathing VAS data for these patients as a function of time. They demonstrate an improvement in lung function and a decrease in the work of breathing, respectively. No clinically significant adverse events requiring unusual treatment were reported, although one patient had a treatable respiratory tract infection upon enrollment, and another patient reported chest tightness at day 4 from the date of the stimulation treatment and continued to be treated with medications.

We therefore conclude from the foregoing preliminary clinical data that noninvasive VNS can safely induce significant bronchodilation during an exacerbation of asthma, even in patients with a poor response to standard pharmacological treatment.

Use of Feedback and Feedforward to Improve Bronchodilation in Individual Patients Individualized treatment may be based on the methods that will now be described in connection with the use of control theory to select stimulation parameters. In brief, the patient's physiological and medical state are modeled a set of differential equations, for example, as coupled nonlinear oscillators; measurements concerning the patient's function are made preferably using ambulatory measurement sensors; parameters of the equations are estimated using the measurements, including measurement of the patient's function following stimulation with different parameters that may be used for the stimulation protocol; and a treatment protocol (set of stimulation parameters) is selected in nearly real-time that will provide the best outcome and avoid or ameliorate the effects of undesired events.

If it is desired to maintain a constant stimulation in the vicinity of the vagus nerve (or any other nerve or tissue that is being stimulated), control theory methods may also be employed to modulate the power of the stimulator in order to compensate for patient motion or other mechanisms that would otherwise give rise to variability in the power of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 10). Such modulation may be accomplished using controllers (e.g. PID controllers) that are known in the art of control theory, as now described.

FIG. 15 is a control theory representation of the disclosed vagus nerve stimulation methods, used not only to maintain a constant stimulation, but also used in connection with the selection of stimulation parameters and stimulation protocols as described below. As shown in FIG. 15, the patient, or the relevant physiological component of the patient, is considered to be the "System" that is to be controlled. The "System" (patient) receives input from the "Environment." For example, in the case of an asthmatic, the environment would include breathed irritants. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may include the control unit 330 in FIGS. 2A-2B. Feedback in the schema shown in FIG. 15 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring, selected to characterize the heart and lung and the modulation of their function by the autonomic nervous system. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. Although some events such as the onset of atrial fibrillation can be detected from the ECG alone or other sensor output, an event marker may also be included in order for the patient to mark relevant circumstances and sensations.

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov PCh, Mark R G, Mietus J E, Moody G B, Peng C K, Stanley H E. PhysioBank, PhysioToolkit, and PhysioNet: Components of a New Research Resource for Complex Physiologic Signals. Circulation 101 (23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration.

It may be therapeutically advantageous to program the control unit 330 to control the impulse generator 310 in such a way as to temporally modulate stimulation by the magnetic stimulator coils or electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the problem of bronchoconstriction that is addressed herein, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants did not experience this problem in the experiments reported here, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual. Patent application publication US2009/0177252, entitled Synchronization of vagus nerve stimulation with the cardiac cycle of a patient, to Arthur D. Craig, discloses a method of treating a medical condition in which the vagus nerve is stimulated during a portion of the cardiac cycle and the respiratory cycle. That disclosure pertains to the treatment of a generic medical condition, so it is not specifically directed to the treatment of bronchoconstriction.

In the present application, stimulation of selected nerve fibers during particular phases of respiration for the treatment of bronchoconstriction may be motivated by two additional physiological considerations. The first is that contraction of bronchial smooth muscle appears to be intrinsically rhythmic. It has been reported that bronchial smooth muscle contracts preferentially over two phases, during mid-inspiration and early expiration. When the vagus efferent nerves are repetitively stimulated with electric pulses, the bronchus constricted periodically; tonic constriction is almost absent in the bronchus in response to the vagally mediated descending commands [KONDO, Tetsuri, Ichiro Kobayashi, Naoki Hayama, Gen Tazaki, and Yasuyo Ohta. Respiratory-related bronchial rhythmic constrictions in the dog with extracorporeal circulation. J Appl Physiol 88(2000): 2031-2036]. Accordingly, a rationale for stimulating the vagus nerve during particular phases of the respiratory cycle is that such stimulation may be used to counteract or inhibit the constriction that occurs naturally during those specific phases of respiration. If the counteracting or inhibiting effects occur only after a delay, then the timing of the stimulation pulses must precede the phases of respiration during which the contraction would occur, by an interval corresponding to the delay.

Another motivation for stimulating the vagus nerve during particular phases of respiration is that an increase or decrease in the duration of subsequent phases of respiration may be produced by applying the stimulation during particular phases of respiration [M. SAMMON, J. R. Romaniuk and E. N. Bruce. Bifurcations of the respiratory pattern produced with phasic vagal stimulation in the rat. J Appl Physiol 75(1993): 912-926]. In particular, a narrow window may exist at the expiratory-inspiratory transition in which it may be possible to induce bursts of inspiratory activity followed by a prolonged breath. Accordingly, if it is therapeutically beneficial to induce deep breaths, those breaths might be induced by stimulating during that time-window. In fact, the physiologically meaningful cycle of stimulation in this case is not a single respiratory cycle, but is instead a collective sequence of respiratory cycles, wherein it makes sense only to speak of stimulation during particular parts of the sequence.

In some embodiments of the invention, overheating of the magnetic stimulator coil may also be minimized by optionally restricting the magnetic stimulation to particular phases of the respiratory cycle, allowing the coil to cool during the other phases of the respiratory cycle. Alternatively, greater peak power may be achieved per respiratory cycle by concentrating all the energy of the magnetic pulses into selected phases of the respiratory cycle.

In our clinical experiments that were summarized above, the electrical impulses delivered to the vagus nerve were optimized to have little effect on heart rate or blood pressure. However, during asthma or COPD attacks or anaphylactic shock, it is sometimes the case that a significant increase or decrease in heart rate accompanies airway constriction. In cases of unsafe or suboptimal heart rates, the teachings of the present invention permit not only prompt airway dilation, but also an improved heart rate, to enable subsequent life saving measures that otherwise would be ineffective or impossible due to severe constriction or other physiological effects. Treatment in accordance with the present invention provides not only bronchodilation, but also optionally improved heart function for a long enough period of time that administered medication such as epinephrine has time to take effect before the patient suffocates. This is because the stimulating, blocking and/or modulating signal can also improve the heart function, by potentially elevating or decreasing heart rate.

Furthermore, as an option in the present invention, parameters of the stimulation may be modulated by the control unit 330 to control the impulse generator 310 in such a way as to temporally modulate stimulation by the magnetic stimulator coil or electrodes, in such a way as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the magnetic stimulator coil or electrodes, in such a way as to achieve and maintain the blood pressure within predetermined safe or desired limits, by the same method that was indicated above for the heart rate. Thus, even if one does not intend to treat bronchoconstriction, embodiments of the invention described above may be used to achieve and maintain the heart rate and blood pressure within desired ranges.

Let the measured output variables of the system in FIG. 15 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i = r_i - y_i$ is small, even if there is environmental input or noise to the system. Consider the error function $e_i = r_i - y_i$ to be the sensed physiological input to the controller in FIG. 15 (i.e., the reference signals are integral to the controller, which subtracts the measured system values from them to construct the control error signal). The controller will also receive a set of measured environmental signals $v_k$ (k=1 to R), which also act upon the system as shown in FIG. 15.

The functional form of the system's input u(t) is constrained to be as shown in FIGS. 2D and 2E. Ordinarily, a parameter that needs adjusting is the one associated with the amplitude of the signal shown in FIGS. 2C-2E. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. One or more accelerometer is attached to the patient's neck, and one or more accelerometer is attached to the head of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118 (1, 1998):82-5]. The ultrasound probe is configured to have the same shape as the stimulator, including the attachment of one or more accelerometer. As part of the preliminary protocol, the patient with accelerometers attached is then instructed to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurło, Przemysław Płonecki, Jacek Starzyński, Stanisław Wincenciak, Andrzej Rysz. Mathematical Modelling of Vagus Nerve Stimulation. pp. 92-97 in: Krawczyk, A. Electromagnetic Field, Health and Environment: Proceedings of EHE '07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form $d y_i/dt = F_i(t, \{y_i\}, \{u_j\}, \{v_k\}; \{r_l\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau)d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative).

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu X U E, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

Commercial versions of PID controllers are available, and they are used in 90% of all control applications. However, performance of system control can be improved by combining the feedback closed-loop control of a PID controller with feed-forward control, wherein knowledge about the system's future behavior can be fed forward and combined with the PID output to improve the overall system performance. For example, if the sensed environmental input in FIG. 15 is such the environmental input to the system will have a deleterious effect on the system after a delay, the controller may use this information to provide anticipatory control input to the system, so as to avert or mitigate the deleterious effects that would have been sensed only after-the-fact with a feedback-only controller. Because the present invention is concerned with anticipating and averting acute medical events, the controller shown in FIG. 15 will generally make use of feedforward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 15 may be a type of predictive controller, methods for which have been developed in other contexts as well, such as when a model of the system is used to calculate future outputs of the system, with the objective of choosing among possible inputs so as to optimize a criterion that is based on future values of the system's output variables.

A mathematical model of the system is needed in order to perform the predictions of system behavior. Models that are completely based upon physical first principles (white-box) are rare, especially in the case of physiological systems. Instead, most models that make use of prior structural and mechanistic understanding of the system are so-called grey-box models, one of which is described below in connection with the forecasting of asthma attacks. If the mechanisms of the systems are not sufficiently understood in order to construct a white or grey box model, a black-box model may be used instead. Such models comprise autoregressive models [Tim BOLLERSLEV. Generalized autoregressive conditional heteroskedasticity. Journal of Econometrics 31(1986): 307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B.V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11 (2, 1999): 305-345], or artificial neural networks [Guoqiang ZHANG, B. Eddy Patuwo, Michael Y. Hu. Forecasting with artificial neural networks: the state of the art. International Journal of Forecasting 14(1998): 35-62].

For the present invention, a grey-box model is preferred, but if a black-box model must be used instead, the preferred model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs. In the present context, a training set of physiological data will have been acquired that includes whether or not the patient is experiencing some type of acute attack. Thus, the classification of the patient's state is whether or not an attack is in progress, and the data used to make the classification consist of the remaining acquired physiological data, evaluated at $\Delta$ time units prior to the time at which the attack data are acquired. Thus, the SVM is trained to forecast the imminence of an attack $\Delta$ time units into the future. After training the SVM, it is implemented as part of the controller to sound an alarm and advise the use of vagal nerve stimulation, whenever there is a forecast of an imminent attack [Christopher J. C. BURGES. A tutorial on support vector machines for pattern recognition. Data Mining and Knowledge Discovery 2(1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4 (2, 2009): 24-38; PRESS, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

Although classical control theory works well for linear systems having one or only a few system variables, special methods have been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the controller shown in FIG. 15 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

Turning now to the use of feedback to control the system, consider the problem of adjusting the input u(t) from the vagus nerve stimulator (i.e., output from the controller) in order to maintain the forced expiratory volume in one second ($FEV_1$) or an alternate lung function index $FEV_1\%$ VC at a predetermined value, using vagus nerve stimulation. Instead of using actual measurement of $FEV_1$, surrogate measurements of $FEV_1$ can also be made, namely, pulsus paradoxus, accessory muscle use or airway resistance (Rint), as now described.

Three types of non-invasive measurements are currently recognized as being surrogates for the measurement of FEV1: pulsus paradoxus, accessory muscle use, and airway resistance. In the preferred embodiment, pulsus paradoxus is measured, which is based on the observation that in asthmatic patients (as well as other patients experiencing bronchoconstriction), the patient's blood pressure waveform will rise and fall as a function of the phase of respiration. In the preferred embodiment, the blood pressure waveform (and the magnitude of any accompanying pulsus paradoxus) is measured non-invasively with an arterial tonometer that is placed, for example, on the patient's wrist [James RAYNER, Flor Trespalacios, Jason Machan, Vijaya Potluri, George Brown, Linda M. Quattrucci, and Gregory D. Jay. Continuous Noninvasive Measurement of Pulsus Paradoxus Complements Medical Decision Making in Assessment of Acute Asthma Severity. CHEST 130 (2006):754-765]. Digitization and analysis of the blood pressure waveform may be performed in a computer dedicated to that purpose, in which case, the numerical value of the continuously varying pulsus paradoxus signal would be transferred to the control unit 330 through a digital interface connecting the control unit 330 and dedicated computer. Alternatively, the control unit 330 may contain an analog-to-digital converter to receive the analog tonometric signal, and the analysis of the blood pressure waveform would be performed within the control unit 330. Instead of using an arterial tonometer to measure the blood pressure wave form and any accompanying pulsus paradoxus, it is also possible to use a pulse oximeter, attached for example, to the patient's finger tip [Donald H ARNOLD, Cathy A Jenkins, Tina V Hartert. Noninvasive assessment of asthma severity using pulse oximeter plethysmograph estimate of pulsus paradoxus physiology. BMC Pulmonary Medicine 10(2010):17; U.S. Pat. No. 7,044,917 and U.S. Pat. No. 6,869,402, entitled Method and apparatus for measuring pulsus paradoxus, to Arnold]. A dedicated computer may be used to acquire and analyze the blood pressure waveform and the magnitude of pulsus paradoxus, which would be transferred to the control unit 330 as indicated above for the tonometrically acquired signal, or the analog pulse oximetry signal may be digitized and processed within the control unit 330, as indicated above.

Accessory muscle use may also be used as a surrogate for the measurement of FEV1 [ARNOLD D H, Gebretsadik T, Minton P A, Higgins S, Hartert T V: Clinical measures associated with FEV1 in persons with asthma requiring hospital admission. Am J Emerg Med 25(2007): 425-429]. The accessory muscles are not used during restful, tidal breathing of a normal patient, but are used during labored breathing. The sternocleidomastoid muscles are the most important accessory muscles of inspiration. They run from the mastoid processes to insert along the medial third of the clavicle. To measure their use, a standard electromyogram may be performed, the signal from which may be digitized and transferred to the control unit 330 as indicated above [T. DE MAYO, R. Miralles, D. Barrero, A. Bulboa, D. Carvajal, S. Valenzuela, and G. Ormeno. Breathing type and body position effects on sternocleidomastoid and suprahyoid EMG activity. Journal of Oral Rehabilitation 32 (7, 2005): 487-494; Roberto MERLETTI, Alberto Botter, Amedeo Troiano, Enrico Merlo, Marco Alessandro Minetto. Technology and instrumentation for detection and conditioning of the surface electromyographic signal: State of the art. Clinical Biomechanics 24 (2009): 122-134]. Alternatively, non-invasive plethysmography may be used to measure accessory muscle use, because as ventilatory demands increase, these muscles contract to lift the sternum and increase the anteroposterior diameter of the upper rib cage during inspiration. The anteroposterior diameter may be measured, for example, by respiratory inductance plethysmography (RIP) and electrical impedance tomography (EIT). RIP uses elastic bands around the chest (and abdomen) to assess changes in lung volume. EIT measures regional impedance changes with electrodes around the patient's chest, each of them injecting and receiving small currents. Such impedance changes have been correlated with dimensional changes of the lung. The plethysmography signal may be digitized and transferred to the control unit 330 as indicated above, as a measure of the extent to which rib cage geometry is changing as the result of accessory muscle use.

Another surrogate for the measurement of FEV1 is the measurement of airway resistance [P. D. BRIDGE, H. Lee, M. Silverman. A portable device based on the interrupter technique to measure bronchodilator response in schoolchildren. Eur Respir J 9(1996): 1368-1373]. Airway resistance is defined as the ratio of the difference between mean alveolar pressure and airway opening pressure to flow measured at the mouth, and it may be measured using devices that are commercially available [e.g., MicroRint, Catalog No. MR5000 from Micromedical Ltd. and Cardinal Health UK 232 Ltd, The Crescent, Jays Close, Basingstoke, RG22 4BS, U.K.]. Such devices have a serial or USB port that permits the control unit 330 to instruct the device to perform the airway resistance measurement and receive the airway resistance data in return, via a serial or USB port in the control unit 330. Because the measurement is necessarily intermittent rather than continuous, and because it requires the patient to breathe passively through a mouthpiece or face mask, this surrogate for the measurement of FEV1 is not the preferred one. For those measurements that give intermittent readings, interpolation may be used to construct a continuous surrogate signal of FEV1 (or other measured signals), which may be designated as the system output y(t).

The functional form of the system's input u(t) is constrained to be as shown in FIG. 2. Ordinarily, the parameter that needs adjusting is the one associated with the amplitude of the signal shown in FIGS. 2C-2E, which should be increased or decreased to accommodate motion-related changes and drift. Rather than adjust the amplitude manually, one may use the PID that was described above, wherein the gains of the PID are tuned according to the Ziegler-Nichols or other rules. Thereafter, the PID adjusts the amplitude automatically so as to best maintain the patient's $FEV_1$ or surrogate value at a preferred value. The default amplitude parameter is then reset according to its average value over time, as the PID continuously adjusts the value of the input u(t) thorough adjustment of the stimulator signal's amplitude (and any other parameters that may have been tuned).

If feedforward rather than (or in addition to) feedback is to be used to control the system, a feedforward model must be specified. The paragraphs that follow describe such a feedforward model, which is based on the observation that bronchial smooth muscle may be oscillating. The properties of oscillators are currently understood through the analysis of differential equation prototypes, such as Duffing's oscillator:

$$\frac{d^2 y}{dt^2} + m\frac{dy}{dt} + \frac{dP}{dy} = f(t),$$

where y is the displacement of the oscillator (e.g., subtracted from a value representing a time-averaged radius under normal conditions, $y_0$), m is a damping parameter, P is a potential function of y, and $f(t)$ is a driving function. In the case of respiration, the driving function would correspond to the flow of air as the respiratory muscles generate inspiration or relax for expiration, as well as the effects of local nerve fibers and circulating hormones on smooth muscle. The potential function P(y) is often assumed to satisfy $$\frac{dP}{dy} = by + ay^3,$$

where a and b are constants $$\left(\text{i.e., } P = \frac{b}{2}y^2 + \frac{a}{4}y^4\right),$$

which for a>0 and b<0 corresponds to a symmetric double-well potential. The potential may also be made asymmetric so that it is easier for the oscillator to reach one well than another, as in:

$$P = \frac{b}{2}y^2 + \frac{a}{4}y^4 + y[c + df(t)],$$

where c and d are parameters for asymmetry that is respectively independent of, or dependent on, the driving function $f(t)$. In any case, two types of motion may be seen with such a double-well model: the motion can be confined to one of the wells when a weak driving function ƒ(t) is applied; or the oscillator can escape a well and visit the other well, and vice versa, when a stronger driving function ƒ(t) is applied [O. I. OLUSOLA, U. E. Vincent, A. N. Njah, and J. A. Olowofela. Bistability in coupled oscillators exhibiting synchronized dynamics. Commun. Theor. Phys. 53 (2010), pp. 815-824]. If noise is added to the system it is possible to convert the former type of motion into the latter, through a mechanism known as stochastic resonance [Luca Gammaitoni, Peter Hanggi, Peter Jung, and Fabio Marchesoni. Stochastic resonance. Rev. Mod. Phys. 70(1998), 223-287].

Duffing's equation describes oscillations in the displacement y that are qualitatively different than those exhibited by a linear, harmonic driven oscillator. Because it embodies a double-well potential, it is appropriate when a system is preferentially in one of two states, such as a constricted state versus a dilated state, as in the case of a bronchiole oscillator. If there were more than two preferential states, a potential having three or more wells may be assumed, as would be the case if the bronchiole oscillator had relaxed, dilated, and intermediate states. A network of coupled oscillators is constructed by making the displacement of one oscillator be a function of one or more of the other oscillators' displacements, i.e., by coupling each oscillator to other oscillators. Each oscillator in the network can in general have different parameter values, and the network can have different forms of local or non-local coupling.

Other well-studied non-linear oscillators include Van der Pol, FitzHugh-Nagumo, Morris-Lecar, Ellias-Grossberg, and Stuart-Landau. Although the detailed oscillations described by such prototypical equations are dependent on the detailed form of the equations and their initial conditions, the qualitative behaviors of such non-linear coupled oscillator equations may often be understood independently of the particular form of the non-linear equation. For example, it is well understood in general that non-linear oscillators, including a set of coupled non-linear oscillators, may exhibit qualitatively different behaviors when the parameters of their equations lie within certain bounds. When graphs are drawn showing the value of one parameter on one axis, and the value of another parameter on another axis, regions of this parameter space may be circumscribed to show what sets of parameter values correspond to each type of qualitatively different dynamics, i.e., a phase diagram. Examples of such phase diagrams are given by MATTHEWS and STROGATZ, which circumscribe different regions of phase space having qualitatively different dynamics, and which are also described below in connection with FIGS. 16A-16B [Paul C. MATTHEWS and Steven H. Strogatz. Phase diagram for the collective behavior of limit-cycle oscillators. Phys. Rev. Lett. 65(1990): 1701-1704].

When dealing with coupled nonlinear oscillators, such as coupled Duffing oscillators, the two or more oscillators may eventually all oscillate with the same phase or they may prefer to oscillate with unrelated phases, again depending on the range in which the parameter values lie. In the case of a two-well oscillator, the relation between the phase of different oscillators refers not only to simultaneously occurring peaks and valleys of displacement, but also whether oscillators are simultaneously trapped in the same potential well. Chimera states, in which part of the system is phase locked and simultaneously another part of the system exhibits oscillators with unrelated phases, are also possible. Chimera states may be particularly significant in regards to the regional inhomogeneity of the lung, when one portion of the lung exhibits unrelated phases, and another region exhibits phase locking. These qualitatively different types of dynamic behavior are influenced by the presence of noise, and they are exhibited by nonlinear oscillators generally, of which the Duffing oscillator is only one example [GUEVARA M. R. Bifurcations involving fixed points and limit cycles in biological systems. In: Nonlinear Dynamics in Physiology and Medicine, edited by Beuter A., Glass L., Mackey M. C., Titcombe M. S. Springer-Verlag, New York, pp. 41-85 (2003); LEE, Wai Shing; Restrepo, Juan G.; Ott, Edward; Antonsen, Thomas M. Dynamics and pattern formation in large systems of spatially-coupled oscillators with finite response times. Chaos 21 (2, 2011), pp. 023122-023122-14; Hiroshi KORI and Alexander S. Mikhailov. Entrainment of Randomly Coupled Oscillator Networks by a Pacemaker. Phys. Rev. Lett. 93(2004), 254101, pp 1-4; M. CISZAK, A. Montina, and F. T. Arecchi. Sharp versus smooth synchronization transition of locally coupled oscillators. Phys. Rev. E 78(2008), 016202, pp 1-4; Daniel M. ABRAMS and Steven H. Strogatz. Chimera States for Coupled Oscillators. Phys. Rev. Lett. 93(2004), 174102, pp 1-4; KONISHI K. Experimental evidence for amplitude death induced by dynamic coupling: van der Pol oscillators. Proc. ISCAS (4, 2004) 792-795; Shinji D O I, Yohei Isotani, Ken-ichiro Sugimoto and Sadatoshi Kumagai. Noise-induced critical breakdown of phase lockings in a forced van der Pol oscillator. Physics Letters A 310 (5-6, 2003): 407-414].

When one or more of the parameters of the set of coupled nonlinear oscillators may be varied under external influences to produce qualitative changes of phase in the system, the parameter is said to be an order parameter. According to the present invention, bronchioles of the lung may be represented mathematically as nonlinear oscillators that are coupled to one another, and an order parameter for the system is the concentration of an environmental lung irritant, as shown in FIG. 16A. Another order parameter is related to the magnitude and duration of vagus nerve stimulation, which will be described below. Consider first only the changes in phase that occur as the concentration of the irritant increases. Moving along the lower axis in FIG. 16A at increasing irritant concentration, the successive phases that are encountered as the concentration is increased are called successively: phase drift, irregular region, and phase locked. The dynamics of the system in each of those phases is represented in FIG. 16B, in which the average, over multiple bronchioles, of bronchiole constriction is shown as a function of time. For present purposes, bronchial constriction may be defined as the average of $y_0/y$, over many bronchioles, where $y_0$ is a time-averaged radius in a normal bronchiole and y is a bronchiole displacement from that radius, such that as y becomes smaller, the constriction becomes larger.

Within the phase drift phase, there are only small fluctuations of constriction amplitude averaged over many bronchioles. This corresponds to a situation in which the bronchioles are oscillating more or less independently of one another. Within the irregular phase, there are small fluctuations along with occasional irregularly-timed large amplitude constrictions. The dynamics are not periodic, but may instead exhibit aperiodic dynamics such as deterministic chaos, Hopf oscillation, quasiperiodicity, and large oscillation [Paul C. MATTHEWS and Steven H. Strogatz. Phase diagram for the collective behavior of limit-cycle oscillators. Phys. Rev. Lett. 65(1990): 1701-1704; Paul C. MATTHEWS, Renato E. Mirollo, and Steven H. Strogatz. Dynamics of a large system of coupled nonlinear oscillators. Physica D: Nonlinear Phenomena 52 (2-3, 1991): 293-331]. During the phase-locked phase, there are large amplitude constrictions, as evidenced by the average of the displacement y over many bronchioles. In that phase, the constrictions correspond to almost all bronchioles in some region(s) of the lung being trapped in one well of the double-well potential, namely, the well corresponding to a constricted bronchiole, as would occur in an asthma attack. However, the lung as a whole may also be in a chimera state, wherein some regions of the lung are in one phase such as the phase-locked phase, while other regions of the lung may be in some other phase such as the phase-drift phase, so that not all bronchioles of the lung need be constricted during an asthma attack.

Irritant concentrations may be measured non-invasively in real time for an ambulatory patient [Kirk J. ENGLEHARDT and John Toon. Asthma attack: Vest-based sensors monitor environmental exposure to help understand causes: web page (www) at the Georgia Tech Research Institute (.gtri) of Georgia Tech (.gatech) educational domain (.edu) in subdomain: /casestudy/asthma-vest-helps-id-asthma-causes; patent application US20110144515, entitled Systems and methods for providing environmental monitoring, to BAYER et al.; and U.S. Pat. No. 7,119,900, entitled Pollen sensor and method, to OKUMURA et al]. For physical external irritants, the unit of irritation should be selected accordingly, such as temperature for cold air as an irritant.

It is understood, however, that in some patients, external irritant triggers are hard to identify, and some irritant triggers may well be endogenous substances. In that case, according to the invention, a surrogate for an unknown or endogenous trigger concentration may be the concentration of exhaled nitric oxide, which can be measured noninvasively using miniature gas sensors placed in the vicinity of the patient's mouth [GILL M, Walker S, Khan A, Green S M, Kim L, Gray S, Krauss B. Exhaled nitric oxide levels during acute asthma exacerbation. Acad Emerg Med 12 (7, 2005):579-86; Oleksandr KUZMYCH, Brett L Allen and Alexander Star. Carbon nanotube sensors for exhaled breath components. Nanotechnology 18 (2007) 375502, pp 1-7]. Accordingly, what is labeled as "Concentration of Environmental Irritants" in FIG. 16A may be replaced by the concentration of any other exogenous or endogenous trigger, or by a surrogate for an asthma trigger.

Referring again to the phase diagram in FIG. 16A, note that the vertical axis is labeled as "Accumulated Vagus Nerve Stimulation Effects." According to the present invention, the effectiveness of vagus nerve stimulation in inhibiting bronchiole constriction is a function of the electric field produced by the stimulation and its waveform, the duration of the stimulation, and if stimulation has ceased, the time since cessation of the last stimulation. Let the numerical value of the accumulated "Accumulated Vagus Nerve Stimulation Effects" with a particular stimulation waveform be denoted as S(t). It may for present purposes be represented as a function that increases at a rate proportional to the stimulation electric field V at the site of the nerve and decays with a time constant $\tau_P$, such that after prolonged stimulation, the accumulated stimulation effectiveness will saturate at a value equal to the product of V and $\tau_P$. Thus, if $T_P$ is the duration of a vagal nerve stimulation, then for time $t<T_P$, $S(t)=V\tau_P[1-\exp(-t/\tau_P)]+S_0\exp(-t/\tau_P)$, and for $t>T_P$, $S(t)=S(T_P)\exp(-[t-T_P]/\tau_P)$, where the time t is measured from the start of a stimulus, and $S_0$ is the value of S when $t=0$. Then, according to FIGS. 16A-16B, as electrical stimuli to the vagus nerve are applied, it is possible for the lung system as a whole to switch from one phase of bronchial constriction to another, even if the lung is exposed to a constant irritant environment.

For example, if the system begins in the phase locked phase shown in FIG. 16A (asthma attack), it can be simulated up and out of that phase into the phase drift phase, and after stimulus ceases, the system will eventually decay back into the phase locked phase (assuming that the patient's physiology remains stationary). The situation with any given individual would depend upon that individual's particular phase diagram, but if the individual has a diagram like the one shown in FIG. 16A, then the best strategy for preventing or terminating unwanted bronchoconstriction would be to stimulate the vagus nerve for as long as possible with as high an electric field as possible, so as to drive the system out of its current phase and into the phase drift phase (or maintain it in the drift phase) for as long as possible. However, that strategy may not be practical, because at some electric field, the stimulus would be too painful and would produce side-effects. In any event the vagus nerve stimulation is not intended to be continuous, as could have been the case with an implanted stimulator. Furthermore, because of decay of the accumulated stimulus effect, additional stimulation may be increasingly ineffective as the effect saturates at a level determined by the stimulation electric field V and decay time constant $\tau_P$.

Implementation of this model of an asthma attack requires a more detailed mathematical embodiment of the invention. For example, in one embodiment, the bronchiole oscillators are represented as coupled Duffing oscillators, as in the following equations with two oscillators. Such a representation can be expanded to any number of oscillators by making all oscillators coupled to all other oscillators so as to emphasize neural or humoral feedback loops, or only to oscillators (bronchioles) in proximity to one another so as to emphasize local nearest-neighbor effects, or some intermediate coupling configuration.

$$\frac{d^2 y_1}{dt^2} + m_1 \frac{dy_1}{dt} + \frac{dP_1}{dy_1} = f_1(t) \text{ and}$$

$$\frac{d^2 y_2}{dt^2} + m_2 \frac{dy_2}{dt} + \frac{dP_2}{dy_2} = f_2(t),$$

where $y_1$ and $y_2$ are the radii of sister branches of bronchioles relative to an offset $y_0$. For example, the bronchioles may be between the fourth and eighth bronchial bifurcations. One form of coupling is through the fact that a flow $f(t)$ through the parent bronchiole of bronchioles 1 and 2 is $f(t)=f_1(t)+f_2(t)$, so that if one sister bronchiole constricts and the other sister bronchiole does not, the flow $f(t)$ will be preferentially distributed to the latter bronchiole. For purposes of estimating the flows, it is assumed that nasal and/or oral airflow is measured (e.g., with thermistors) in conjunction with respiratory inductive plethysmography, mercury in silastic strain gauges or impedance pneumography so as to measure total respiratory air flow, which can be calibration with a spirometer. Assuming that the lengths of the bronchi and bronchioles are the same at any corresponding level of branching, assuming the validity of Ohm's law and Poiseuille's law, and given the measured total air flow, the values of the driving flows $f_1(t)$ and $f_2(t)$ can be estimated for the current values of $y_1$ and $y_2$. Similar equations are written for the multiple levels of bronchiole bifurcations. Because flow at one level of bronchiole branching can influence flow that is connected to it at another level, the equations for the bronchiole oscillators are therefore coupled to one another at least by virtue of the anatomy of the lung and flow within the branching bronchioles.

According to the invention, the presence of irritant in the airstream of any bronchiole (or other trigger surrogate) is accounted for by making parameters describing the potential P be a function of the flow and concentration of environmental irritant. For example, with the asymmetric potential $$P = \frac{b}{2}y^2 + \frac{a}{4}y^4 + y[c + df(t)],$$

where d is a parameter that is a function of irritant concentration, the system would preferentially constrict the bronchiole on inspiration (positive $f$, preventing the irritant from reaching the alveoli) and preferentially dilate the bronchiole on expiration (negative $f$, allowing the irritant to be expelled from the alveoli). If K is the irritant concentration, then for example, the dependence of parameter d on K may be expressed as $d = d_0 + d_1 K + d_2 K^2 + \ldots$.

An increase in the parameter c would increase the stability of the potential well corresponding to bronchoconstriction, independently of any changes in the flow. Accordingly, stimulation of the bronchioles by histamine, the parasympathetic nervous system, or any other factor that promotes bronchoconstriction should be accompanied by an increase in the parameter c. Conversely, a decrease in the parameter c would increase the stability of the potential well corresponding to bronchodilation. Accordingly, stimulation of the bronchioles by epinephrine, the sympathetic nervous system, or any other factor that promotes bronchodilation should be accompanied by a decrease in the parameter c. For example, one may write c as $c = c_c - c_d$, where an increase in $c_c$ caused bronchoconstriction and an increase in $c_d$ causes bronchodilation. Then, the vagal nerve stimulation S(t), which was defined above, may be introduced through the parameter $c_d$. For example, $\alpha = \alpha_{00} + \alpha_{10} U + \alpha_{01} S + \alpha_{11} US + \alpha_{20} U^2 + \alpha_{02} S^2 + \ldots = c_{d0} + c_{d1} S + c_{d2} S^2 + \ldots$.

Breathing is to some extent under voluntary control, so that an individual can deliberately vary the driving function $f(t)$. On the other hand, breathing is also to some extent involuntary and controlled by the nervous system. Accordingly, one may expand the above model to account for respiratory reflexes [H. T. MILHORN Jr., R. Benton, R. Ross, and A. C. Guyton. A mathematical model of the human respiratory control system. Biophys J. 5(1965):27-46]. To do so, the coupling parameter(s) may also be made to be a function of multiple oscillator values, possibly at a previous time t–?, so as to account for the time delay ? in neural reflexes between afferent signals and efferent effects that couple oscillators to one another. Such an expanded neural control model may be used to forecast $f(t)$, or alternatively, non-physiological models may be used to forecast future values of $f(t)$ based on previous values of $f(t)$ [CAMINAL P, Domingo L, Giraldo B F, Vallverdú M, Benito S, Vázquez G, Kaplan D. Variability analysis of the respiratory volume based on non-linear prediction methods. Med Biol Eng Comput 42 (1, 2004):86-91]. It is understood that additional extensions of the above dynamical model may make the anatomy and physiology more complete, accurate or detailed; for example, one may wish to create a more realistic model of the patient's lung anatomy than what was described above [LEE, S. L. A.; Kouzani, A. Z.; Hu, E. J.; From lung images to lung models: A review. IEEE International Joint Conference on Neural Networks 2008: 2377-2383].

Usefulness of this method is dependent on the extent to which the patient is willing to undergo measurement to allow estimation of an embodiment of the equations' parameters. It is understood that the measurement will consist of a period of baseline monitoring, followed by a period during which the vagus nerve is stimulated using a default stimulation protocol or during which vagal nerve stimulation parameters are varied. The most useful measurements would be ones in which nearby groups of bronchioles are measured separately, so as to be able to estimate parameters separately for those localized groups of oscillators. This will require imaging of the lung in order to evaluate the spatial heterogeneity of bronchiolar constriction.

Many methods exist for the noninvasive imaging of the lung. However, the noninvasive imaging methods that are preferred here are those that may be performed by continuous noninvasive ambulatory monitoring. At the present time, the preferred imaging methods comprise electrical impedance tomography and acoustic imaging. Electrical impedance tomography (EIT) is an imaging technique in which an image of the conductivity of the chest is inferred from surface electrical measurements. To perform EIT, conducting electrodes are attached to the skin of the patient and small alternating currents are applied to some or all of the electrodes. The resulting electrical potentials are measured, and the process may be repeated for numerous different configurations of applied current. A calculation is then performed to infer the lung structure that could have given rise to the measured electrical potentials [David HOLDER. Electrical impedance tomography: methods, history, and applications. Institute of Physics Publishing, Bristol and Philadelphia, 2005; WENG T R, Spence J A, Polgar G, Nyboer J. Measurement of regional lung function by tetrapolar electrical impedance plethysmography. Chest 76 (1, 1979):64-9; FRERICHS I. Electrical impedance tomography (EIT) in applications related to lung and ventilation: a review of experimental and clinical activities. Physiol Meas. 21 (2, 2002):R1-21; FRERICHS I, Hinz J, Herrmann P, Weisser G, Hahn G, Dudykevych T, Quintel M, Hellige G. Detection of local lung air content by electrical impedance tomography compared with electron beam CT. J Appl Physiol 93 (2, 2002):660-6; J. KARSTEN, T. Meier, H. Heinze. Bedside-measurements of electrical impedance tomography and functional residual capacity during positioning therapy in a case of acute respiratory failure Applied Cardiopulmonary Pathophysiology, 15(2011): 81-86; FAGERBERG A, Söndergaard S, Karason S, Aneman A. Electrical impedance tomography and heterogeneity of pulmonary perfusion and ventilation in porcine acute lung injury. Acta Anaesthesiol Scand. 2009 November; 53(10):1300-9].

The other noninvasive ambulatory imaging method, acoustic imaging, involves the placement of multiple microphones on the patient's chest and back. It is particularly useful to detect and localize groups of bronchioles that have abruptly opened and made a corresponding sound [KOMPIS M, Pasterkamp H, Wodicka G R. Acoustic imaging of the human chest. Chest 120 (4, 2001):1309-21; PASTERKAMP H, Kraman S S, Wodicka G R. Respiratory sounds. Advances beyond the stethoscope. Am J Respir Crit Care Med 156 (3 Pt 1, 1997):974-87; Adriano M. ALCENAR, Arnab Majumdar, Zoltan Hantos, Sergey V. Buldyrev, H. Eugene Stanley, Béla Suki. Crackles and instabilities during lung inflation. Physica A: Statistical Mechanics and its Applications 357 (1, 2005): 18-26].

In addition to these noninvasive measurements, as well as conventional ambulatory measurements for breathing, heart rate, and the like, one would preferably use an accelerometer and/or inclinometer so as to account for changes in lung anatomy and physiology as the patient changes posture or moves about [GALVIN I, Drummond G B, Nirmalan M. Distribution of blood flow and ventilation in the lung: gravity is not the only factor. Br J Anaesth 98 (4, 2007):420-8]. The sensors may be embedded in garments or placed in sports wristwatches, as currently used in programs that monitor the physiological status of soldiers [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141].

Estimation of parameters of the equations from continuously acquired data may be made using existing methods such as the multiple shooting and recursive (e.g., Kalman filter) approaches [Henning U. VOSS and Jens Timmer. Nonlinear dynamical system identification from uncertain and indirect measurements. International Journal of Bifurcation and Chaos 14 (6, 2004):1905-1933], or synchronization methods [HDI ABARBANEL, D R Creveling, and J M Jeanne. Estimation of parameters in nonlinear systems using balanced synchronization. Physical Review E 77 (2008):016208, pp 1-14]. As the patient's ambulatory data evolve in time, the estimated parameters may also evolve in time and must be updated.

After parameter estimation, numerical simulation with the coupled-oscillator equations into the future may forecast the imminent onset of an asthma attack, i.e., an abrupt transition wherein groups of bronchioles constrict (see FIGS. 16A-16B). It is understood that the simulation must occur at a rate that is significantly faster than actual time, otherwise there would be little warning for the patient. When such a warning is given, the patient or a caregiver would perform vagus nerve stimulation as described above in order to avert the asthma attack.

For situations in which it is impractical to use the above gray-box model of asthma, for example, if the patient is unwilling to wear the electrical impedance tomography and acoustic imaging sensors for measuring respiratory heterogeneity, then one may instead use the black-box approach that was described above, using the remaining sensors (respiration, environmental sensors, etc.). In that case, the patient would mark the onset of an asthma attack with an event button, and the set of ambulatory measurements would be used to train a support vector machine classifier model. After training, that model could be used to forecast the asthma attack and advise the patient to perform vagus nerve stimulation, or to select stimulation parameters so as to most rapidly terminate an ongoing bronchoconstrictive exacerbation.

In another aspect of the invention, the applicant has discovered that many seemingly disparate disorders may, in fact, have common causes that manifest into different symptoms or disorders in different individuals. Specifically, the applicant has discovered that in certain individuals who may suffer from disorders, such as depression, asthma, COPD, migraine, cluster headache, anxiety, fibromyalgia, epilepsy and the like, certain areas of the brain are prone to periodic or continuous excessive excitatory neurotransmitter levels. These periodic excessive excitatory neurotransmitter levels can be caused by certain "triggers", such as noxious substances entering the lungs that cause airway reactivity or other triggers, such as chocolate or seafood that can cause migraines in certain individuals. In other cases, the patient may have pathologically high excitatory neurotransmitter levels on a continuous basis without any particular trigger. One example, of an excitatory neurotransmitter is glutamate, which is known to be associated with migraines.

The excessive excitatory neurotransmitter levels in a patient's brain can be caused by inaccurate signals from the body transmitted through the vagus nerve or other nerves or these excessive levels can be caused by the brain overreacting to normal signals coming from the body. In some cases, these excessive excitatory neurotransmitter levels may be caused by inappropriate inactivity in the production and/or release of inhibitory neurotransmitters, such as GABA, serotonin and/or norepinephrine. A reduced level of these inhibitory neurotransmitter levels can result in excessive levels of the excitatory neurotransmitters that they are meant to balance.

The present invention seeks to address this inbalance in neurotransmitters in the brain that can result in many of the disorders mentioned above. Specifically, afferent nerve fibers in the vagus nerve are stimulated with the devices, signals and methods described above to heighten activity in areas of the brain (e.g., the periaqueducatal gray, locus ceruleus and/or raphe nuclei) resulting in the release of inhibitory neurotransmitter levels, such as GABA, norepinephrine and/or serotonin). For example, as discussed above, heightened activity in the locus coeruleus will result in a release of norephinephrine or an increase the release of norephinephrine. This release of inhibitory neurotransmitters suppresses the excessive excitatory neurotransmitters and creates balance in the brain such that the brain either does not overreact to certain stimuli and/or to modulate the pathologically high level of excitatory neurotransmitters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for treating a disorder in a patient comprising:
a housing having an electrically permeable or conducting contact surface for contacting an outer skin surface of the patient; and
an energy source within the housing configured to transmit an electric current through the outer skin surface of the patient to a vagus nerve within the patient,
an electrode directly coupled to the energy source and not directly coupled to the electrically permeable contact surface;
a conducting medium within the housing filling a space created between the electrode and the electrically permeable contact surface,
wherein the electric current is sufficient to generate an electric field between about 10 to 600 V/m at the vagus nerve above a threshold for generating action potentials within fibers of the vagus nerve responsible for activating neural pathways causing suppression of excitatory neurotransmitters within a brain of the patient.

2. The device of claim 1 wherein the excitatory neurotransmitters comprise catecholamines.

3. The device of claim 1 wherein the excitatory neurotransmitters comprise glutamate.

4. The device of claim 1 wherein the excitatory neurotransmitters comprise acetycholine.

5. The device of claim 1 wherein the electric field is below a threshold for generating action potentials within fibers of the vagus nerve responsible for bronchoconstriction.

6. The device of claim 1 wherein the electric field is below the threshold for generating action potentials within fibers of the vagus nerve responsible for modulating heart rate or blood pressure.

7. The device of claim 1 wherein the electric current is sufficient to generate an electrical field gradient at the vagus nerve greater than 2 V/m/mm.

8. The device of claim 1 wherein the electric field is less than 100 V/m.

9. The device of claim 1 wherein the electric current is sufficient to generate an electric field greater than 100 V/m but less then about 600 V/m at the vagus nerve.

10. The device of claim 1 wherein the energy source comprises a battery.

11. The device of claim 1 wherein the electric current comprises bursts of pulses with a frequency of about 3 to about 100 bursts per second.

12. The device of claim 11 wherein the electric current comprises bursts of between 1 and 20 pulses per burst, with each pulse being about 50 to 1000 microseconds in duration.

13. The device of claim 1 wherein the housing is a handheld device configured for contacting a surface of the skin of a patient.

14. A device for treating a disorder in a patient comprising:
a housing having an electrically permeable or conducting contact surface for contacting an outer skin surface of the patient; and
an energy source within the housing configured to transmit an electric current through the outer skin surface of the patient to a vagus nerve within the patient,
an electrode directly coupled to the energy source and not directly coupled to the electrically permeable contact surface;
a conducting medium within the housing filling a space created between the electrode and the electrically permeable contact surface
wherein the electric current is sufficient to generate an electrical field gradient at the vagus nerve greater than 2 V/m/mm above a threshold for generating action potentials within fibers of the vagus nerve responsible for activating neural pathways causing suppression of excitatory neurotransmitters within a brain of the patient.

15. The device of claim 14 wherein the excitatory neurotransmitters comprise catecholamines.

16. The device of claim 14 wherein the excitatory neurotransmitters comprise glutamate.

17. The device of claim 14 wherein the excitatory neurotransmitters comprise acetycholine.

18. The device of claim 14 wherein the electric field is below a threshold for generating action potentials within fibers of the vagus nerve responsible for bronchoconstriction.

19. The device of claim 14 wherein the electric field is below the threshold for generating action potentials within fibers of the vagus nerve responsible for modulating heart rate or blood pressure.

20. The device of claim 14 wherein the electric field is between about 10 to 600 V/m.

21. The device of claim 14 wherein the electric field is less than 100 V/m.

22. The device of claim 14 wherein the energy source comprises a signal generator and one or more electrodes coupled to the signal generator within the housing.

23. The device of claim 14 wherein the energy source comprises a battery.

24. The device of claim 14 wherein the electric current comprises bursts of pulses with a frequency of about 3 to about 100 bursts per second.

25. The device of claim 24 wherein the electric current comprises bursts of between 1 and 20 pulses per burst, with each pulse being about 50 to 1000 microseconds in duration.

26. The device of claim 14 wherein the housing is a handheld device configured for contacting a surface of the skin of a patient.

* * * * *